(12) United States Patent
Manchester

(10) Patent No.: US 11,549,096 B2
(45) Date of Patent: Jan. 10, 2023

(54) GENETIC PERTURBATION OF THE RNA DEGRADOSOME PROTEIN COMPLEX

(71) Applicant: Zymergen Inc., Emeryville, CA (US)

(72) Inventor: Shawn Manchester, Oakland, CA (US)

(73) Assignee: Zymergen Inc., Emeryville, CA (US)

( * ) Notice: Subject to any disclaimer, the term of this patent is extended or adjusted under 35 U.S.C. 154(b) by 961 days.

(21) Appl. No.: 16/314,953

(22) PCT Filed: Jun. 27, 2017

(86) PCT No.: PCT/US2017/039452
§ 371 (c)(1),
(2) Date: Jan. 3, 2019

(87) PCT Pub. No.: WO2018/009372
PCT Pub. Date: Jan. 11, 2018

(65) Prior Publication Data
US 2019/0194769 A1    Jun. 27, 2019

Related U.S. Application Data

(60) Provisional application No. 62/358,201, filed on Jul. 5, 2016.

(51) Int. Cl.
| | | |
|---|---|---|
| C12N 15/77 | (2006.01) |
| C12P 7/04 | (2006.01) |
| C12P 7/06 | (2006.01) |
| C12N 1/20 | (2006.01) |
| C07K 14/34 | (2006.01) |
| C12P 13/04 | (2006.01) |
| C12P 1/04 | (2006.01) |
| C12P 7/40 | (2006.01) |
| C12P 7/46 | (2006.01) |
| C12P 7/56 | (2006.01) |
| C12P 7/58 | (2006.01) |
| C12P 13/06 | (2006.01) |
| C12P 13/08 | (2006.01) |
| C12P 13/12 | (2006.01) |
| C12P 13/20 | (2006.01) |
| C12P 13/22 | (2006.01) |
| C12R 1/15 | (2006.01) |

(52) U.S. Cl.
CPC .............. *C12N 1/205* (2021.05); *C07K 14/34* (2013.01); *C12N 15/77* (2013.01); *C12P 1/04* (2013.01); *C12P 7/04* (2013.01); *C12P 7/06* (2013.01); *C12P 7/40* (2013.01); *C12P 7/46* (2013.01); *C12P 7/56* (2013.01); *C12P 7/58* (2013.01); *C12P 13/04* (2013.01); *C12P 13/06* (2013.01); *C12P 13/08* (2013.01); *C12P 13/12* (2013.01); *C12P 13/20* (2013.01); *C12P 13/222* (2013.01); *C12P 13/225* (2013.01); *C12P 13/227* (2013.01); *C12R 2001/15* (2021.05)

(58) Field of Classification Search
CPC .......... C12N 1/205; C12N 15/77; C07K 14/34
See application file for complete search history.

(56) References Cited

U.S. PATENT DOCUMENTS

| | | |
|---|---|---|
| 7,118,904 B2 | 10/2006 | Möckel et al. |
| 2002/0082403 A1* | 6/2002 | Mockel .................... C12N 9/88 |
| | | 536/23.1 |
| 2002/0197605 A1 | 12/2002 | Nakagawa et al. |
| 2004/0126842 A1 | 7/2004 | Dreyfus et al. |
| 2005/0003494 A1* | 1/2005 | Zelder .................... C07K 14/34 |
| | | 435/488 |
| 2006/0269975 A1 | 11/2006 | Pompejus et al. |
| 2007/0042474 A1 | 2/2007 | Pompejus et al. |
| 2007/0274972 A1 | 11/2007 | Muller et al. |
| 2014/0356921 A1 | 12/2014 | Deng et al. |
| 2015/0140626 A1 | 5/2015 | Song et al. |

FOREIGN PATENT DOCUMENTS

| | | |
|---|---|---|
| WO | WO 2006/028063 A1 | 3/2006 |
| WO | WO 2007/141580 A2 | 12/2007 |
| WO | WO 2011/154147 A1 | 12/2011 |
| WO | WO 2015/175793 A1 | 11/2015 |
| WO | WO 2017/100376 A2 | 6/2017 |
| WO | WO 2018/009372 A1 | 1/2018 |

OTHER PUBLICATIONS

Pátek, Miroslav, et al., "Promoters of Corynebacterium glutamicum", Journal of Biotechnology (Sep. 4, 2003); 104(Issues 1-3): 311-323.
Carpousis, A.J., et al., "MRNA degradation. A tale of poly(A) and multiprotein machines." Trends Genet. (Jan. 1999); 15(1): 24-28.
Carpousis, A.J., et al., "Copurification of *E. coli* RNAase E and PNPase: evidence for a specific association between two enzymes important in RNA processing and degradation." Cell (Mar. 1994); 76(5): 889-900.
Coburn, G.A., et al., "Reconstitution of a minimal RNA degradosome demonstrates functional coordination between a 3' exonuclease and a DEAD-box RNA helicase." Genes Dev. (Oct. 1999); 13(19): 2594-2603.
Goloubinoff, P., et al., "Reconstitution of active dimeric ribulose bisphosphate carboxylase from an unfoleded state depends on two chaperonin proteins and Mg-ATP." Nature (Dec. 1989); 342(6252): 884-889.
Gray and Fersht, "Refolding of barnase in the presence of GroE." J Mol Biol. (Aug. 1993); 232(4): 1197-1207.

(Continued)

*Primary Examiner* — Antonio Galisteo Gonzalez
(74) *Attorney, Agent, or Firm* — Cooley LLP

(57) ABSTRACT

The present disclosure provides novel bacterial strains with altered expression or start codon modification of one or more RNA degradation/processing genes. The RNA degradation genes of the present disclosure are controlled by heterologous promoters. The present disclosure further describes methods for generating microbial strains comprising heterologous promoter sequences operably linked to RNA degradation/processing genes.

40 Claims, 6 Drawing Sheets

Specification includes a Sequence Listing.

(56) References Cited

OTHER PUBLICATIONS

Hunger, K., et al., "Cold-induced putative DEAD box RNA helicases CshA and CshB are essential for cold adaptation and interact with cold shock protein B in Bacillus subtilis." J Bacteriol. (Jan. 2006); 188(1): 240-248.
Jain, C., "The E. coli RhlE RNA helicase regulates the function of related RNA helicases during ribosome assembly." RNA (Feb. 2008); 14(2): 381-389.
Jones, G.H., "Guanosine pentaphosphate synthetase from Streptomyces antibioticus is also a polynucleotide phosphorylase." J Bacteriol. (Jul. 1996); 178(14): 4281-4288.
Li, Z., et al., "RNase G (CafA protein) and RNase E are both required for the 5' maturation of 16S ribosomal RNA." EMBO J. (May 1999); 18(10): 2878-2885.
Miczak, et al., "Proteins associated with RNase E in a multicomponent ribonucleolytic complex." Proc Natl Acad Sci U S A. (Apr. 1996); 93(9): 3865-3869.
Oun, S., et al., "The CshA DEAD-box RNA helicase is important for quorum sensing control in *Staphylococcus aureus*." RNA Biol. (Jan. 2013); 10(1): 157-165.
PCT/US2017/039452, International Preliminary Report on Patentability, dated Jan. 8, 2019, 20 pages.
PCT/US2017/039452, International Search Report and Written Opinion, dated Sep. 29, 2017, 24 pages.
Py, B., "A DEAD-box RNA helicase in the *Escherichia coli* RNA degradosome." Nature (May 1996); 381(6578): 169-172.
Régnier and Arraiano, "Degradation of mRNA in bacteria: emergence of ubiquitous features." Bioessays (Mar. 2000); 22(3): 235-244.
Schmid and Linder, "D-E-A-D protein family of putative RNA helicases." Mol Microbiol. (Feb. 1992); 6(3): 283-291.
Zahn and Pluckthun, "GroE Prevents the Accumulation of Early Folding Intermediates of Pre-ß-lactamase without Changing the Folding Pathway." Biochemistry (Mar. 1992); 31(12): 3249-3255.
Zahn, R., et al., "Catalysis of amide proton exchange by the molecular chaperones GroEL and SecB." Science (Feb. 1996); 271(5249): 642-645.
Extended European Search Report in EP Application No. 17824711.0 dated Dec. 13, 2019, 11 pages.
Jain, et al., "Consequences of RNase E scarcity in *Escherichia coli*". Mol Microbiol. (Feb. 2002); 43(4): 1053-1064.
Lopez, et al., "The C-terminal half of RNase E, which organizes the *Escherichia coli* degradosome, participates in mRNA degradation but not rRNA processing in vivo". Mol Microbiol. (Jul. 1999); 33(1): 188-199.
Nouaille, et al., "The stability of an mRNA is influenced by its concentration: a potential physical mechanism to regulate gene expression". Nucleic Acids Res. (Nov. 16, 2017); 45(20): 11711-11724. Epub Sep. 7, 2017.
Rauhut and Klug, "mRNA degradation in bacteria". FEMS Microbiol Rev. (Jun. 1999); 23(3): 353-370.
Sakai, et al., "Increased production of pyruvic acid by *Escherichia coli* RNase G mutants in combination with cra mutations". Appl Microbiol Biotechnol. (Aug. 2007); 76(1): 183-192. Epub May 5, 2007.
Viegas, et al., "Effect of the increased stability of the penicillin amidase mRNA on the protein expression levels". FEBS Lett. (Sep. 12, 2005); 579(22): 5069-5073.

* cited by examiner

GENETIC PERTURBATION OF THE RNA DEGRADOSOME PROTEIN COMPLEX

CROSS-REFERENCE TO RELATED APPLICATIONS

This application is a national phase filing under 35 U.S.C. § 371 of International Application No. PCT/US2017/039452, filed Jun. 27, 2017, which claims priority to U.S. Provisional Application No. 62/358,201 filed Jul. 5, 2016. The contents of each of the aforementioned applications is incorporated by reference in its entirety, including all descriptions, references, figures, and claims for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ZYMR_007_01WO_SeqList_ST25.txt, date recorded: Jun. 21, 2017, file size 115,272 bytes).

FIELD

The present disclosure is directed to microbial genomic engineering. The disclosed methods, compositions, and kits for RNA degradosome perturbations facilitate steady state modulation of selected mRNAs, and assist researchers in improving bacterial strain production efficiencies.

BACKGROUND

The regulation of bacterial gene expression occurs at many levels, including transcriptional control, or control of the synthesis of mRNA from a given gene; translational control, or the regulation of the efficiency by which the mRNA is translated into polypeptide sequence by the ribosome; and mRNA stability, or the efficiency at which a given mRNA population within the cell is processed and rendered inactive.

While methods for altering the transcription levels of mRNA have been widely studied, other techniques for optimizing the post-translational steady state of mRNA have remained more elusive.

In some embodiments, the present disclosure teaches methods for improving industrial strain efficiency, for example by modulating RNA stability through altering genetic sequences and reaction conditions.

SUMMARY OF THE DISCLOSURE

The present disclosure provides novel methods for improving the performance of industrial host organisms. In some embodiments, the methods of the present disclosure modulate mRNA steady states, and lead to improvements in biomass or product performance of the host strain.

In some embodiments, the present disclosure teaches a genetically engineered host cell with enhanced industrial performance, said host cell comprising: a) heterologous promoter polynucleotide, and b) a polynucleotide encoding an RNA degradation gene; wherein the heterologous promoter polynucleotide is operably linked to the polynucleotide.

In some embodiments, the RNA degradation gene of the present disclosure is an endogenous gene. In other embodiments, of the present disclosure, the host cell comprises a heterologous promoter polynucleotide operably linked to an exogenous RNA degradation enzyme.

In some embodiments, the exogenous coding polynucleotide is a gene derived from a different species. In other embodiments, the exogenous coding polynucleotide is an endogenous gene that has been mutated.

In some embodiments, the present disclosure teaches mutating the start codons of one or more of the host cell's RNA degradation enzymes, wherein the non-mutated start codon of the RNA degradation gene is changed from 'ATG' or 'GTG' to 'TTG.' For example, in some embodiments, the present disclosure teaches replacing ATG start codons with TTG. In some embodiments, the present disclosure teaches replacing ATG start codons with GTG. In some embodiments, the present disclosure teaches replacing GTG start codons with ATG. In some embodiments, the present disclosure teaches replacing GTG start codons with TTG. In some embodiments, the present disclosure teaches replacing TTG start codons with ATG. In some embodiments, the present disclosure teaches replacing TTG start codons with GTG.

In some embodiments the present disclosure teaches a genetically engineered host cell comprising a heterologous promoter operably linked to an RNA degradation gene, wherein the heterologous promoter is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

In some embodiments, the heterologous promoter of the present disclosure comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

In some embodiments the heterologous promoter polynucleotide sequence is selected from the group consisting of SEQ ID NO: 1, SEQ ID NO: 2, SEQ ID NO: 3, and SEQ ID NO: 6. In some embodiments the heterologous promoter polynucleotide sequence is SEQ ID NO: 1. In some embodiments the heterologous promoter polynucleotide sequence is SEQ ID NO: 2. In some embodiments the heterologous promoter polynucleotide sequence is SEQ ID NO: 3. In some embodiments the heterologous promoter polynucleotide sequence is SEQ ID NO:6.

In some embodiments the present disclosure teaches a genetically engineered host cell comprising a heterologous promoter operably linked to a polynucleotide encoding an RNA degradation gene, wherein the RNA degradation gene is selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22.

In some embodiments the present disclosure teaches a genetically engineered host cell comprising a heterologous promoter operably linked to a polynucleotide encoding an RNA degradation gene, wherein the polynucleotide encodes for an RNA degradation protein is selected from the group consisting of SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO:47.

In some embodiments, the polynucleotide encoding the RNA degradation gene is selected from the group consisting of SEQ ID NO: 11, SEQ ID NO: 12, SEQ ID NO: 13, SEQ ID NO: 14, SEQ ID NO: 17, and SEQ ID NO: 20.

In some embodiments the polynucleotide encodes for an RNA degradation gene is selected from the group consisting of SEQ ID NO: 36, SEQ ID NO: 37, SEQ ID NO: 38, SEQ ID NO: 39, SEQ ID NO: 41, SEQ ID NO: 42, and SEQ ID NO:45.

In some embodiments the present disclosure teaches a genetically engineered host cell comprising wherein the genetically engineered host cell comprises a combination of a heterologous promoter operably linked to a polynucleotide encoding an RNA degradation gene, said combination selected from the group consisting of: a—(SEQ ID NO: 1::SEQ ID NO: 10), b—(SEQ ID NO: 1::SEQ ID NO: 14), c—(SEQ ID NO: 1::SEQ ID NO: 18), d—(SEQ ID NO: 1::SEQ ID NO: 20), e—(SEQ ID NO: 2::SEQ ID NO: 11), f—(SEQ ID NO: 2::SEQ ID NO: 18), g—(SEQ ID NO: 2::SEQ ID NO: 13), h—(SEQ ID NO: 2::SEQ ID NO: 18), i—(SEQ ID NO: 2::SEQ ID NO: 17), j—(SEQ ID NO: 2::SEQ ID NO: 19), k—(SEQ ID NO: 3::SEQ ID NO: 11), l—(SEQ ID NO: 3::SEQ ID NO: 14), m—(SEQ ID NO: 3::SEQ ID NO: 12), n—(SEQ ID NO: 3::SEQ ID NO: 15), o—(SEQ ID NO: 3::SEQ ID NO: 17), p—(SEQ ID NO: 3::SEQ ID NO: 19), q—(SEQ ID NO: 5::SEQ ID NO: 14), r—(SEQ ID NO: 5::SEQ ID NO: 11) (SEQ ID NO: 6::SEQ ID NO: 13), s—(SEQ ID NO: 6::SEQ ID NO: 19), t—(SEQ ID NO: 8::SEQ ID NO: 21), u—(SEQ ID NO: 8::SEQ ID NO: 14), v—(SEQ ID NO: 6::SEQ ID NO: 20), w—(SEQ ID NO: 6::SEQ ID NO: 11), x—(SEQ ID NO: 8::SEQ ID NO: 9), and y—(SEQ ID NO: 8::SEQ ID NO: 18).

In some embodiments, the RNA degradation gene is SEQ ID NO: 11. In some embodiments, the RNA degradation gene is SEQ ID NO: 12. In some embodiments, the RNA degradation gene is SEQ ID NO: 13. In some embodiments, the RNA degradation gene is SEQ ID NO: 14. In some embodiments, the RNA degradation gene is SEQ ID NO: 17. In some embodiments, the RNA degradation gene is SEQ ID NO: 20.

In some embodiments, the methods and compositions of the present disclosure are compatible with any species of host cell organism. In some embodiments, the methods of the present disclosure are applied to prokaryotic host cell. In some embodiments, the methods of the present disclosure are applied to bacteria host cells. In some embodiments, the methods of the present disclosure are applied to eukaryotic host cells.

In some embodiments, the methods of the present disclosure teach engineered host cell belongs to genus *Corynebacterium*. In some embodiments, the methods of the present disclosure teach genetically engineered host cell is *Corynebacterium glutamicum*.

In some embodiments, the present disclosure further teaches methods of producing a biomolecule comprising culturing a host cell of the disclosure under conditions suitable for producing the biomolecule.

In some embodiments, the biomolecule of the present disclosure is an amino acid, an organic acid, or an alcohol.

In some embodiments, the present disclosure teaches methods of producing amino acids selected from the group consisting of tyrosine, phenylalanine, tryptophan, aspartic acid, asparagine, threonine, isoleucine, methionine, and lysine.

In some embodiments, the present disclosure teaches methods of producing an organic acid selected from the group consisting of succinate, lactate and pyruvate.

In some embodiments, the present disclosure teaches methods of producing an alcohol, such as ethanol or isobutanol.

In some embodiments, the genetically engineered host cells of the present disclosure are capable of producing at least a 2% higher titer of the biomolecule than a genetically identical host cell lacking said heterologous promoter polynucleotide, when cultured under identical conditions.

In some embodiments, the genetically engineered host cells of the present disclosure are capable of producing at least a 3% higher titer of the biomolecule than a genetically identical host cell lacking said heterologous promoter polynucleotide, when cultured under identical conditions.

In some embodiments, the genetically engineered host cells of the present disclosure are capable of producing at least a 6% higher titer of the biomolecule than a genetically identical host cell lacking said heterologous promoter polynucleotide, when cultured under identical conditions.

In some embodiments, the present disclosure measures titer at carbon exhaustion to determine yield for a genetically engineered host. Thus in some embodiments, the genetically engineered host strains of the present disclosure produces at least about 2%-10% higher yield of the biomolecule than a genetically identical host cell lacking said heterologous promoter polynucleotide, when cultured in identical conditions.

In some embodiments, the genetically engineered host cells of the present disclosure exhibit at least about 5% higher saturation biomass than a genetically identical host cell lacking said heterologous promoter polynucleotide, when cultured in identical conditions. In some embodiments, the genetically engineered host cells of the present disclosure exhibit at least about 10% higher saturation biomass than a genetically identical host cell lacking said heterologous promoter polynucleotide, when cultured in identical conditions.

In some embodiments, the genetically engineered host cells of the present disclosure exhibit at least about 20% higher saturation biomass than a genetically identical host cell lacking said heterologous promoter polynucleotide, when cultured in identical conditions.

In some embodiments, the present disclosure teaches a method for generating a host cell capable of increased production of a biomolecule, the method comprising: introducing a heterologous promoter polynucleotide into the genome of the host cell, wherein the heterologous promoter polynucleotide is operably linked to a polynucleotide encoding an RNA degradation gene, thereby creating a genetically engineered host cell; wherein the genetically engineered host cell produces a higher biomolecule yield compared to the biomolecule yield of a control host cell cultured under identical conditions, wherein the control host cell does not comprise the heterologous promoter polynucleotide.

In some embodiments, the present disclosure teaches a method for generating a host cell capable of increased saturation biomass, the method comprising: introducing a heterologous promoter polynucleotide into the genome of the host cell, wherein the heterologous promoter polynucleotide is operably linked to a polynucleotide encoding an RNA degradation gene, thereby creating a genetically engineered host cell; wherein the genetically engineered host cell exhibits increased saturation biomass compared to the saturation biomass of a control host cell cultured under identical conditions, wherein the control host cell does not comprise the heterologous promoter polynucleotide.

In some embodiments, the RNA degradation gene of the present disclosure is an endogenous gene. In other embodiments, of the present disclosure, the host cell comprises a heterologous promoter polynucleotide operably linked to an exogenous coding polynucleotide encoding and RNA degradation enzyme.

In yet other embodiments, the present disclosure teaches a genetically engineered prokaryotic host cell with enhanced industrial performance, said host cell comprising: a) a coding polynucleotide encoding an RNA degradation gene; and b) a mutation in the start codon of the coding polynucleotide of (a); wherein the mutation results in the replacement of the start codon of the coding polynucleotide with a different start codon.

Thus, in some embodiments, the present disclosure teaches a method for generating a host cell capable of increased production of a biomolecule, the method comprising: genetically modifying the host cell, wherein the modifying comprises mutating the start codon of an endogenous RNA degradation gene, wherein the modification generates a genetically engineered host cell expressing RNA degradation gene, wherein the genetically engineered host cell produces an increased amount of a biomolecule as compared to the amount of the biomolecule produced from a control host cell, wherein the control host cell does not comprise the mutated start codon.

In some embodiments, the present disclosure teaches a method for generating a host cell capable of increased yield of a biomolecule or increased saturation biomass, the method comprising: genetically modifying the host cell, wherein the modifying comprises mutating the start codon of an endogenous RNA degradation gene, wherein the modification generates a genetically engineered host cell; wherein the genetically engineered host cell has increased biomolecule yield as compared to the biomolecule yield of a control host cell, or wherein the genetically engineered host cell achieves higher saturation biomass as compared to the saturation biomass of the control host cell, wherein the control host cell does not comprise the start codon mutation of the genetically engineered host cell, and wherein the genetically engineered host cell and the control host cell are cultured under identical conditions.

In some embodiments, the present disclosure teaches mutating an RNA degradation gene selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22. In some embodiments, the present disclosure mutates SEQ ID NO: 19.

In some embodiments, the present disclosure teaches particular heterologous promoter::RNA degradation gene combinations designed to improve the biomass of host cell cultures. For example, in some embodiments, the present disclosure teaches a heterologous promoter:RNA degradation gene combination selected from the group consisting of: SEQ ID No: 1::SEQ ID No: 20, SEQ ID No: 1::SEQ ID No: 14, SEQ ID No: 2::SEQ ID No: 13, SEQ ID No: 2::SEQ ID No: 18, SEQ ID No: 2::SEQ ID No: 17, SEQ ID No: 2::SEQ ID No: 19, SEQ ID No: 3::SEQ ID No: 11, SEQ ID No: 3::SEQ ID No: 19, SEQ ID No: 3::SEQ ID No: 14, SEQ ID No: 5::SEQ ID No: 18, SEQ ID No: 5::SEQ ID No: 14, SEQ ID No: 6::SEQ ID No: 13, SEQ ID No: 6::SEQ ID No: 19, SEQ ID No: 8::SEQ ID No: 21, and SEQ ID No: 8::SEQ ID No: 14.

In some embodiments, the present disclosure teaches particular heterologous promoter::RNA degradation gene combinations designed to improve the product production in host cell cultures. For example, in some embodiments, the present disclosure teaches a heterologous promoter::RNA degradation gene combination selected from the group consisting of: SEQ ID No: 2::SEQ ID No: 17, SEQ ID No: 3::SEQ ID No: 17, SEQ ID No: 6::SEQ ID No: 20, SEQ ID No: 6::SEQ ID No: 11, and SEQ ID No: 8::SEQ ID No: 9.

In some embodiments, the present disclosure teaches particular start codon replacements of RNA degradation genes designed to improve the biomass of host cell cultures. For example, in some embodiments, the present disclosure teaches a start codon replacement of an RNA degradation gene selected from the group consisting of GTG to TTG of SEQ ID No: 21, ATG to TTG of SEQ ID No: 14, GTG to TTG of SEQ ID No: 19, and ATG to TTG of SEQ ID No: 17.

In some embodiments, the present disclosure teaches particular start codon replacements of RNA degradation genes designed to improve product production of host cell cultures. For example, in some embodiments, the present disclosure teaches a start codon replacement of an RNA degradation gene selected from the group consisting of: GTG to TTG of SEQ ID No: 21, ATG to TTG of SEQ ID No: 10.

DETAILED DESCRIPTION

Definitions

Figure 1:
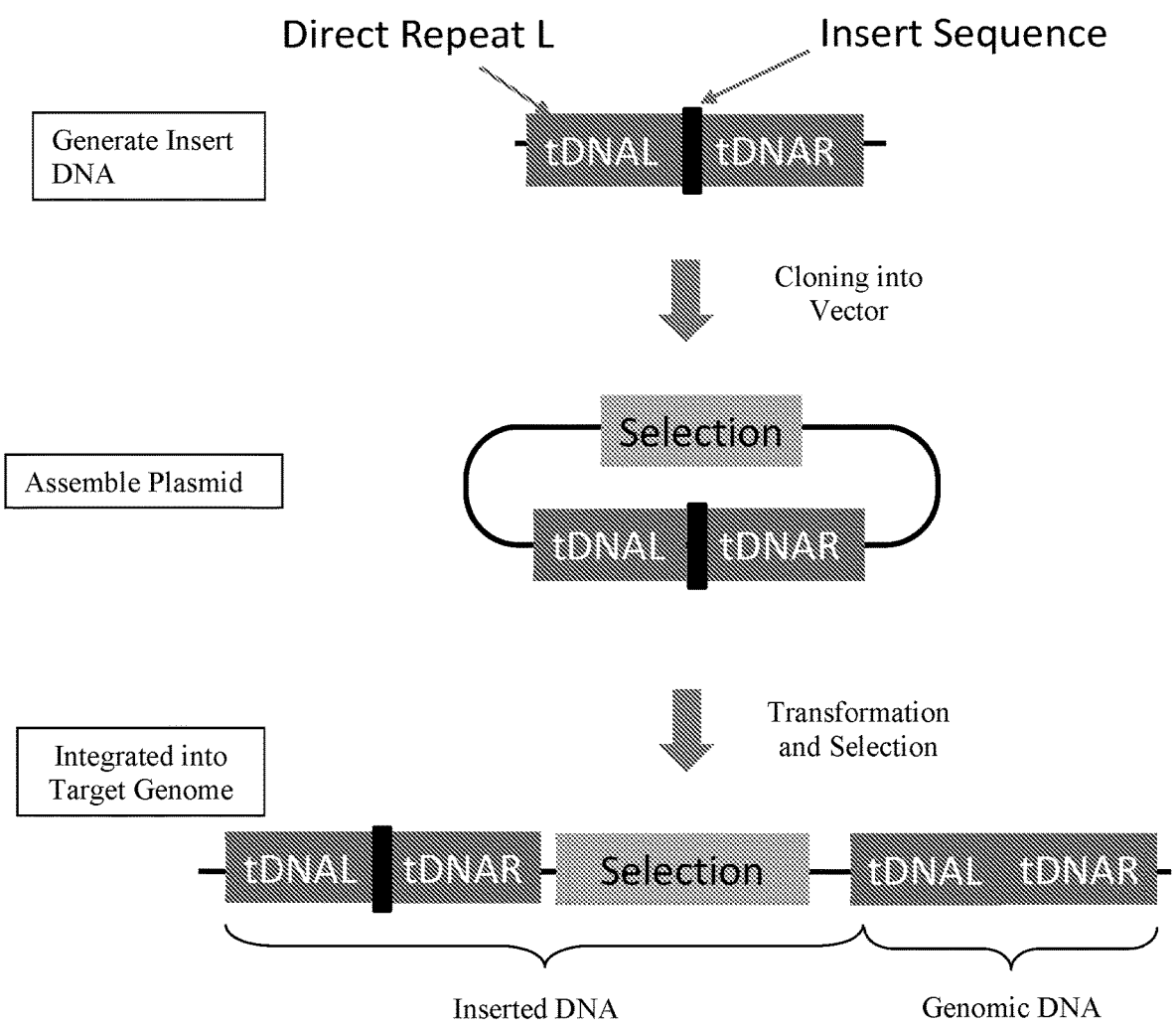
FIG. 1 depicts assembly of transformation plasmids of the present disclosure, and their integration into host organisms. The insert DNA is generated by combining one or more synthesized oligos in an assembly reaction. DNA inserts containing the desired sequence are flanked by regions of DNA homologous to the targeted region of the genome. These homologous regions facilitate genomic integration, and, once integrated, form direct repeat regions designed for looping out vector backbone DNA in subsequent steps. Assembled plasmids contain the insert DNA, and optionally, one or more selection markers.

While the following terms are believed to be well understood by one of ordinary skill in the art, the following definitions are set forth to facilitate explanation of the presently disclosed subject matter.

The term "a" or "an" refers to one or more of that entity, i.e., can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "cellular organism" "microorganism" or "microbe" should be taken broadly. These terms are used interchangeably and include, but are not limited to, the two prokaryotic domains, Bacteria and Archaea. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in said tables or figures. The same characterization holds true for the recitation of these terms in other parts of the Specification, such as in the Examples.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper)thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others)(2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

The terms "genetically modified host cell," "recombinant host cell," and "recombinant strain" are used interchangeably herein and refer to microorganisms that have been genetically modified by the cloning and transformation methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring microorganism from which it was derived. It is understood that the terms refer not only to the particular recombinant microorganism in question, but also to the progeny or potential progeny of such a microorganism.

The term "genetically engineered" may refer to any manipulation of a host cell's genome (e.g. by insertion or deletion of nucleic acids).

The term "strain improvement program" refers to any methods for improving host cell cultures. For example, the present disclosure teaches methods for genetically engineering host cells to exhibit improved performance.

The term "wild-type" describes a cell or multicellular organism that occurs in nature, i.e. a cell that has not been genetically modified.

The term "control" or "control host cdl" refers to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification differentiating the treatment host cell. Thus, the control for a genetically modified organism of the present disclosure, comprising a heterologous promoter sequence operably linked to an RNA degradation gene could be a genetically identical organism without the heterologous promoter.

The term "RNA degradation gene" or "RNA degradosome" should be taken broadly. These terms are used interchangeably and include, but are not limited to, any prokaryotic or eukaryotic gene associated with in-vivo RNA degradation, mRNA transcript processing, or other functions resulting in modulation of mRNA stability. In some embodiments, the RNA degradation genes of the present disclosure comprise any polynucleotide encoding for the polypeptide sequences encoded by the protein sequences disclosed in Table 1.

In some embodiments, the disclosure refers to the "RNA degradosome gene" or "RNA degradation genes" of lists/tables and figures present in the disclosure. This characterization can refer to not only the specific gene of the tables and figures, but also to homologs, orthologs, paralogs, or variants thereof. The same characterization holds true for the recitation of these terms in other parts of the Specification, such as in the Examples. For example, in some embodiments the present disclosure also encompasses RNA degradation polynucleotides and polypeptides disclosed in Table 12.

As used herein, the term "phenotype" refers to the observable characteristics of an individual cell, cell culture, organism, or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure, homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd. Oxford, U.K.), ALIGN Plus (Scientific and Educational Software, Pennsylvania) and AlignX (Vector NTI, Invitrogen, Carilsbad, Calif.). Another alignment program is Sequencher (Gene Codes, Ann Arbor, Mich.), using default parameters.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to. e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual (3rd ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press. New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001. In some embodiments, stringent conditions are hybridization in 0.25 M Na2HPO4 buffer (pH 7.2) containing 1 mM Na2EDTA, 0.5-20% sodium dodecyl sulfate at 45° C., such as 0.5%, 1% 2%, 3%, 4%, 5%, 6%, 7%, 8%, 9%, 10%, 11%, 12%, 13%, 14%, 15%, 16%, 17%, 18%, 19% or 20%, followed by a wash in 5×SSC, containing 0.1% (w/v) sodium dodecyl sulfate, at 55° C. to 65° C.

As used herein, "promoter" refers to a DNA sequence capable of controlling the expression of a coding sequence or functional RNA. In some embodiments, the promoter sequence may consist of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. In some embodiments, the disclosure refers to the promoter of lists/tables and figures present in the disclosure. This characterization can refer to not only the specific promoter, but also to variants thereof. The same characterization holds true for the recitation of these terms in other parts of the Specification, such as in the Examples. In some embodiments, the present disclosure teaches use of specific promoter::gene combinations.

As used herein, the term "heterologous" or"heterologous promoter" refers to a nucleic acid sequence which is not naturally found in the particular organism. A sequence may also be heterologous if it is placed outside of its normal sequence context. Thus, a "heterologous promoter" as used in the present disclosure may be a promoter sourced from a different species or strain, or may also be a promoter sequence sourced from the same species, but inserted into a different locus within the genetically engineered host cell.

As used herein, the term "endogenous," "endogenous gene," or "endogenous RNA degradation gene" refers to the naturally occurring copy of a gene, in the location in which it is found within the host cell genome. In the context of the present disclosure, operably linking a heterologous promoter to an endogenous RNA degradation gene means genetically inserting a heterologous promoter sequence in front of the RNA degradation gene, in the location where that gene is naturally present.

As used herein, the term "exogenous" is used interchangeably with the term "heterologous," and refers to a substance coming from some source other than its native source. For example, the terms "exogenous protein," or "exogenous gene" refer to a protein or gene from a non-native source or location, and that have been artificially supplied to a biological system. Artificially mutated variants of endogenous genes are considered "exogenous" for the purposes of this disclosure.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

The term "operably linked" means in this context, the sequential arrangement of the promoter polynucleotide according to the disclosure with a further oligo- or polynucleotide, resulting in transcription of said further polynucleotide. In some embodiments, the promoter sequences of the present disclosure are inserted just prior to a gene's 5'UTR, or open reading frame. In other embodiments, the operably linked promoter sequences and gene sequences of the present disclosure are separated by one or more linker nucleotides.

The term "carbon source" generally refers to a substance suitable to be used as a source of carbon for cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a product of interest (e.g. small molecule, peptide, synthetic compound, fuel, alcohol, etc.) in a fermentation process. However, a feedstock may contain nutrients other than a carbon source.

The term "product of interest" or "biomolecule" as used herein refers to any product produced by microbes from feedstock. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a microbe, such as, a microbial enzyme, including: catalase, amylase, protease, pectinase, glucose isomerase, cellulase, hemicellulase, lipase, lactase, streptokinase, and many others. The intracellular component may also include recombinant proteins, such as: insulin, hepatitis B vaccine, interferon, granulocyte colony-stimulating factor, streptokinase and others.

The term "volumetric productivity" or "production rate" is defined as the amount of product formed per volume of medium per unit of time. Volumetric productivity can be reported in gram per liter per hour (g/L/h).

The term "specific productivity" is defined as the rate of formation of the product. To describe productivity as an inherent parameter of the microorganism and not of the fermentation process, productivity is herein further defined as the specific productivity in gram product per gram of cell dry weight (CDW) per hour (g/g CDW/h). Using the relation of CDW to OD600 for the given microorganism specific productivity can also be expressed as gram product per liter culture medium per optical density of the culture broth at 600 nm (OD) per hour (g/L/h/OD).

The term "yield" is defined as the amount of product obtained per unit weight of raw material and may be expressed as g product per g substrate (g/g)("Product Yield"). Yield may be expressed as a percentage of actual yield over theoretical yield ("Percent Yield"). "Theoretical yield" is defined as the maximum amount of product that can be generated per a given amount of substrate as dictated by the stoichiometry of the metabolic pathway used to make the product.

The term "titre" or "titer" is defined as the strength of a solution or the concentration of a substance in solution. For example, the titre of a product of interest (e.g. small molecule, peptide, synthetic compound, fuel, alcohol, etc.) in a fermentation broth is described as g of product of interest in solution per liter of fermentation broth (g/L). In some embodiments, the present disclosure teaches that biomass of a culture can be measured at any time (e.g., titer measurements after a predetermined culture time, or at carbon exhaustion). Titer measured at carbon exhaustion is also considered reflective of the yield of the culture in those conditions.

The term "total titer" is defined as the sum of all product of interest produced in a process, including but not limited to the product of interest in solution, the product of interest in gas phase if applicable, and any product of interest removed from the process and recovered relative to the initial volume in the process or the operating volume in the process.

The term "biomass" refers to the cell density of a culture. In some embodiments the biomass of the of the cultures of the present disclosure are determined by the optical density of their cultures at 600 nm spectrum minus the optical density of a corresponding control media without the organism. In other embodiments, "biomass" can be measured by other metrics, such as cell density (e.g., via a hemocytometer) or by culture weight after separating cells from their culture media. In some embodiments, the present disclosure teaches that biomass of a culture can be measured at any time.

The term "saturation biomass" refers to the peak biomass achieved by the host cell under a given set of conditions. For example, in some embodiments, saturation mass can refer to the maximum biomass achieved by a culture in a specific growth media, at a specific temperature and light conditions. In some embodiments, the present disclosure compares the saturation biomass of various modified microbes under identical growth conditions, such that any differences in saturation biomass are due to the underlying genetic differences between the tested microbes.

Optimizing Gene Expression

In some embodiments, the present disclosure teaches methods of improving host cell productivity through modulation of cellular gene expression. Gene expression is the measurable output of a multi-level regulatory process comprising transcriptional control of RNA synthesis, mRNA stability, mRNA translation into protein, and protein stability. Although much attention has been devoted to the control of gene expression through the transcriptional modulation of genes (e.g., by changing promoters, or inducing regulatory transcription factors), comparatively few efforts have been made towards understanding the post-transcriptional regulation of desirable genes.

In some embodiments, the present disclosure teaches methods of improving cellular expression of desirable genes by perturbing an organism's RNA degradation genes (e.g., the RNA degradosome). The RNA degradosome is responsible for the degradation of intracellular RNA, including mRNA, and as such plays an important role in the steady state concentration of RNA in the cell.

In some embodiments, the present invention is based, in part, on the inventor's recognition that increasing the transcription rate of desirable genes does not always lead to increased expression of the desired protein. In prokaryotes, the tight coupling between transcription and translation is important for mRNA stability. For example, when a prokaryotic mRNA is over expressed through increased transcription by a fast T7 RNAP, long stretches of ribosome-free message occur, rendering the untranslated mRNAs unstable. (Makarova, O. V. et al. (1995) "Transcribing of Escherichia coli genes with mutant T7 RNA polymerases: stability of lacZ mRNA inversely correlates with polymerase speed" Proc Natl Acad Sci USA 92:12250-12254).

Without wishing to be bound to any one theory, the present inventors believe that modulation of a cell's RNA degradation genes can improve cellular efficiency by optimizing the mRNA stability of selected genes of interest. Steady state RNA concentrations affect a number of cellular phenotypes through a variety of mechanisms, including serving as the template for protein production in the case of mRNA or regulation of mRNA production through non-coding (nc) RNA. Because the degradosome acts as a hub for RNA degradation, and is composed of a variety of different proteins which operate on different types of RNA to various extents, systematic perturbation of the genes in the degradosome can have complex transcriptome wide effects, and thus complex effects on phenotype. Coupled with a method to determine the effect of each perturbation on the phenotype of interest in high throughput, this invention allows for the discovery and stacking of perturbations that lead to improved microbial performance across a variety of phenotypes.

RNA Degradosome and RNA Degradation Genes

In some embodiments, the present disclosure teaches RNA degradation and processing genes. In some embodiments, the RNA degradation genes of the present disclosure are part of the RNA degradosome. The RNA degradosome of Escherichia coli is a multienzyme complex that was discovered during efforts to purify and characterize RNase E (Carpousis, A. J. et al. (1994) "Copurification of E. coli RNAase E and PNPase: evidence for a specific association between two enzymes important in RNA processing and degradation" Cell 76: 889-900; Carpousis, A. J. et al. (1999) "mRNA degradation A tale of poly(A) and multiprotein machines" Trends Genet 15: 24-28; Miczak, A. et al. (1996) "Proteins associated with RNase E in a multicomponent ribonucleolytic complex" Proc Natl Acad Sci USA 93: 3865-3869).

RNase E is a single-strand-specific endonuclease, and is believed to be the principal endonuclease in E. coli messenger RNA decay (Regnier, P. and Arraiano, C. M. (2000) "Degradation of mRNA in bacteria: emergence of ubiquitous features" Bioessays 22: 235-244). RNase E is a large, 1061 residue protein, with its nucleolytic activity resides in the N-terminal half of the protein. The C-terminal half of the protein contains a proline rich linker, an arginine rich RNA binding domain (RBD) and a region that is the scaffold for protein-protein interactions with the other components of the degradosome (Carpousis, A. J. 2007 "The RNA Degradosome of Escherichia coli: An mRNA-Degrading Machine Assembled on RNase E" Annu. Rev. Microbiol. 61:7147).

Proteins related to RNase E are found throughout the eubacterial kingdom and in some plants (Condon, C. et al. (2001) "Identification of the gene encoding the 5S ribosomal RNA maturase in Bacillus subtilis: mature 5S rRNA is dispensable for ribosome function" RNA 7: 242-253). The plant homologues are presumably in the chloroplast, which is an organelle of eubacterial origin. An RNase E-based degradosome was recently identified in Rhodobacter capsulatus (Jager, S. et al. (2001) "An mRNA degrading complex in Rhodobacter capsulatus" Nucleic Acids Res 29: 4581-4588).

The RNAse E complex is believed to contain two DEAD proteins and the transcription termination factor Rho, and PNPase and enolase (Carpousis. A. J. 2007 "The RNA Degradosome of Escherichia coli: An mRNA-Degrading Machine Assembled on RNase E" Annu. Rev. Microbiol. 61:71-87). E. coli also encodes a paralogue of RNase E now known as RNase G (Li, Z. et al. (1999) "RNase G (CafA protein) and RNase E are both required for the 5' maturation of 16S ribosomal RNA" Embo J 18: 2878-2885.). It has significant homology to the N-terminal catalytic domain of RNase E but is smaller because it lacks a c-terminal half. The 'RNase E/G' family of proteins can thus be divided into two groups: the large RNase E-like enzymes that can form degradosomes and the small RNase G-like enzymes that apparently act alone.

The other integral components of the degradosome are enolase, an RNA helicase (RhlB) and polynucleotide phosphorylase (PNPase). RhlB is a member of the DEAD-box family of RNA helicases (Schmid, S. R., and Linder, P. (1992) "D-E-A-D protein family of putative RNA helicases Mol Microbiol 6: 283-291). PNPase, a single-strand-specific exonuclease, is a member of the RNase PH family of 3'→5' RNA degrading enzymes (Deutscher, M. P., and Li, Z. (2001) "Exoribonucleases and their multiple roles in RNA metabolism" Prog Nucleic Acid Res Mol Biol 66: 67-105; Symmons, M., Williams et al. (2002) "Running rings around RNA: a superfamily of phosphate-dependent RNases" Trends Biochem. Sci., 27: 11-18). Members of both families are found in a wide range of prokaryotic and eukaryotic organisms.

Experiments in vitro demonstrated that RhlB in the degradosome facilitates the degradation of structured RNA by PNPase (Coburn, G. A. et al. (1999) "Reconstitution of a minimal RNA degradosome demonstrates functional coordination between a 3' exonuclease and a DEAD-box RNA helicase" Genes Dev 13: 2594-2603; Py, B. et al. (1996) "A DEAD-box RNA helicase in the *Escherichia coli* RNA degradosome" Nature 381: 169-172).

The Rho I enzyme (Rho factor) is another important regulator of mRNA expression, and Rho-dependent transcriptional termination. Thus in some embodiments, the present disclosure teaches methods of perturbing Rho L Rho-dependent transcriptional termination is responsible for regulating about half of all of Ecol's transcribed genes. Other termination factors discovered in *E. coli* include Tau and nusA (See Sandy B. Primrose and Richard Twyman (2006) "Principles of Gene Manipulation and Genomics" John Wiley & Sons ISBN 1-4051-3544-1). Rho is a member of the family of ATP-dependent hexameric helicases that function by wrapping nucleic acids around a single cleft extending around the entire hexamer. Rho binds to RNA and then uses its ATPase activity to provide the energy to translocate along the RNA until it reaches the RNA-DNA helical region, where it unwinds the hybrid duplex structure, and leads to transcriptional termination.

In some embodiments, the present disclosure also teaches use of other DEAD-box helicases, such as CshA, which has been associated with gene expression in stress conditions (Oun, S. et al. "The CshA DEAD-box RNA helicase is important in quorum sensing control in *Staphylococcus aureus*. RNA Biol. 2013 10(1): 157-165; Hunger, K. et al. "Cold-Induced Putative DEAD Box RNA Helicases CshA and CshB Are Essential for Cold Adaptation and Interact with Cold Shock Protein B in *Bacillus subtilis*" J Bacteriol. 2006 188(1): 240-248).

Other helicases with regulatory effect on RNA steady state are also within the scope of the present disclosure. For example, the present disclosure teaches perturbation of the rhlE gene. In *E. coli* RhlE RNA helicase regulates the function of related RNA helicases during ribosome assembly (Jain, C. "The *E. coli* RhlE RNA helicase regulates the function of related RNA helicases during ribosome assembly" RNA. 2008 14(2)381-389).

In some embodiments, the RNA degradation enzymes of the present disclosure comprise selected protein chaperone genes. For example, in some embodiments, the present disclosure teaches groEL and groEL2 genes. GroEL is a member of the hsp60 family of heat shock proteins. GroEL is a tetradecamer wherein each monomeric subunit has a molecular weight of approximately 57 kD. GroEL facilitates the folding of a number of proteins by two mechanisms; (1) it prevents aggregation by binding to partly folded proteins (Goloubinoff P et al (1989) Nature 342: 984-889; Zahn R and Plückthun A (1992) Biochemistry 21: 3249-3255), which then refold on GroEL to a native-like state (Zahn R and Plückthun A (1992) Biochemistry 21: 3249-3255; Gray T E and Fersht A R (1993) J Mol Biol L: 1197-1207); and (2) it continuously anneals misfolded proteins by unfolding them to a state from which refolding can start again (Zahn R et al (1996) Science 271: 642-645). Some mutations in the apical domain led to a decrease in polypeptide binding (Fenton W A et al (1994) Nature 371: 614-619), suggesting that this domain is involved in the binding of polypeptides.

In other embodiments, the present disclosure teaches perturbation of DnaK. DnaK has been demonstrated to be the central protein in a multiprotein bacterial chaperone system including the chaperone protein DnaK and a variety of co-chaperone proteins such as DnaJ and GrpE. The co-chaperone proteins are essential to the efficient physiological processing of both natural and unnatural substrates. One role for this chaperone system is to catalyze the refolding of either unfolded or misfolded bacterial proteins, as is evident from the role of this system in the heat-shock response. An additional role of the DnaK chaperone system is the regulation of gene expression through the processing of specific RNA polymerase subunits.

In some embodiments, other genes involved in gene expression are within the scope of the present disclosure. For example. In some embodiments, the present disclosure teaches gpsL GpsI is a putative multifunctional enzyme involved in guanosine pentaphosphate synthesis and polyribonucleotide nucleotidyltransferase. *E. coli* polynucleotide phosphorylase, purified GPSI was shown to catalyze the polymerization of ADP and the phosphorolysis of poly(A) (Jones, G. and Bibb, M. "Guanosine Pentaphosphate Synthetase from *Streptomyces antibioticus* Is Also a Polynucleotide Phosphorylase" J. of Bact. 1996 July 4281-4288.).

In other embodiments, the present disclosure teaches Enolase (eno). Enolase, also known as phosphopyruvate hydratase, is a metalloenzyme responsible for the catalysis of the conversion of 2-phosphoglycerate (2-PG) to phosphoenolpyruvate (PEP), the ninth and penultimate step of glycolysis. (See for example, U.S. Pat. No. 7,118,904).

In some embodiments, the present invention teaches modulating gene expression of a host cell by perturbing one or more RNA degradation genes. Persons having skill in the art will recognize that RNA degradation gene perturbations of the present disclosure can, in some embodiments, comprise any method for the modification of proteins that are members of the RNA degradosome for the purpose of optimizing a particular cellular phenotype. In some embodiments, perturbation of an RNA degradation gene can comprise directed or random genetic mutation of the gene sequence itself. In other embodiments, perturbation of an RNA degradation gene can comprise modulating expression with mutated endogenous or exogenous promoters.

A non-exhaustive list of the RNA degradation genes of the present disclosure is provided in Table 1 below.

TABLE 1

Selected RNA degradation genes of the present disclosure

| Species | Gene name | SEQ ID (cDNA) | SEQ ID (Protein) | Gene "short name" |
|---|---|---|---|---|
| Corynebacterium glutamicum | cg1144 | 9 | 34 | G1 |
| Corynebacterium glutamicum | cg2453 | 10 | 35 | G2 |
| Corynebacterium glutamicum | cshA | 11 | 36 | G3 |
| Corynebacterium glutamicum | dnaK | 12 | 37 | G4 |
| Corynebacterium glutamicum | eno | 13 | 38 | G5 |
| Corynebacterium glutamicum | gpsI | 14 | 39 | G6 |
| Corynebacterium glutamicum | groEL | 15 | 40 | G7 |
| Corynebacterium glutamicum | groEL homolog | 16 | 41 | G8 |
| Corynebacterium glutamicum | groEL2 | 17 | 42 | G9 |
| Corynebacterium glutamicum | mutM2 | 18 | 43 | G10 |
| Corynebacterium glutamicum | rhlE | 19 | 44 | G11 |
| Corynebacterium glutamicum | rho | 20 | 45 | G12 |

TABLE 1-continued

Selected RNA degradation genes of the present disclosure

| Species | Gene name | SEQ ID (cDNA) | SEQ ID (Protein) | Gene "short name" |
|---|---|---|---|---|
| Corynebacterium glutamicum | rne (RNAse E) | 21 | 46 | G13 |
| Corynebacterium glutamicum | cg2160/ RNAse J | 22 | 47 | G14 |

In some embodiments, the RNA degradation genes of the present invention exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a gene (either cDNA, or protein) from Table 1.

Promoters

In some embodiments, the present disclosure teaches methods of selecting promoters with optimal expression properties to modulate RNA degradation function and produce beneficial effects on overall-host strain productivity.

Promoters regulate the rate at which genes are transcribed and can influence transcription in a variety of ways. For example, in some embodiments, the present disclosure teaches methods of identifying one or more promoters and/or generating variants of one or more promoters within a host cell, which exhibit a range of expression strengths (e.g. promoter ladders discussed infra), or superior regulatory properties (i.e., tighter regulatory control for selected genes).

Constitutive promoters, for example, direct the transcription of their associated genes at a constant rate regardless of the internal or external cellular conditions, while regulatable promoters increase or decrease the rate at which a gene is transcribed depending on the internal and/or the external cellular conditions, e.g. growth rate, temperature, responses to specific environmental chemicals, and the like. Promoters can be isolated from their normal cellular contexts and engineered to regulate the expression of virtually any gene, enabling the effective modification of cellular growth, product yield and/or other phenotypes of interest.

In some embodiments, the present disclosure teaches methods of identifying one or more promoters and/or generating variants of one or more promoters within a host cell, which exhibit a range of expression strengths (e.g. promoter ladders discussed infra), or superior regulatory properties (i.e., tighter regulatory control for selected genes, or responsiveness to particular conditions). A particular combination of these identified and/or generated promoters can be grouped together as a promoter ladder for use in the RNA degradation perturbation experiments explained in more detail below.

In some embodiments, promoter ladders are created by identifying natural, native, or wild-type promoters associated with a target gene of interest that have a range of expression strengths. These identified promoters can be grouped together as a promoter ladder.

In some embodiments, promoter ladders are created by: identifying natural, native, or wild type promoters associated with a target gene of interest and then mutating said promoter to derive multiple mutated promoter sequences. Each of these mutated promoters is tested for effect on target gene expression. In some embodiments, the edited promoters are tested for expression activity across a variety of conditions, such that each promoter variant's activity is documented/characterized/annotated and stored in a database. The resulting edited promoter variants are subsequently organized into promoter ladders arranged based on the strength of their expression (e.g., with highly expressing variants near the top, and attenuated expression near the bottom, therefore leading to the term "ladder").

In some embodiments, the present disclosure teaches promoter ladders that are a combination of identified naturally occurring promoters and mutated variant promoters.

In some embodiments, the present disclosure teaches methods of identifying natural, native, or wild type promoters that satisfied both of the following criteria: 1) represented a ladder of constitutive promoters; and 2) could be encoded by short DNA sequences, ideally less than 100 base pairs. In some embodiments, constitutive promoters of the present disclosure exhibit constant gene expression across two selected growth conditions (typically compared among conditions experienced during industrial cultivation). In some embodiments, the promoters of the present disclosure will consist of a ~60 base pair core promoter, and a 5' UTR between 26- and 40 base pairs in length.

In some embodiments, one or more of the aforementioned identified naturally occurring promoter sequences are chosen for gene editing. In some embodiments, the natural promoters are edited via any known genetic mutation methods. In other embodiments, the promoters of the present disclosure are edited by synthesizing new promoter variants with the desired sequence.

The entire disclosures of U.S. Patent Application No. 62/264,232, filed on Dec. 7, 2015, and PCT Publication No. WO2017/100376, are each hereby incorporated by reference in its entirety for all purposes.

A non-exhaustive list of the promoters of the present disclosure is provided in Table 2 below.

TABLE 2

Selected promoter sequences of the present disclosure.

| SEQ ID No. | Promoter Short Name |
|---|---|
| 1 | P1 |
| 2 | P2 |
| 3 | P3 |
| 4 | P4 |
| 5 | P5 |
| 6 | P6 |
| 7 | P7 |
| 8 | P8 |

In some embodiments, the promoters of the present invention exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a promoter sequences from Table 2.

RNA Degradation Gene Expression Perturbation

In some embodiments, the present disclosure teaches optimizing the expression of one or more RNA degradosome genes by operably linking mid gene with a promoter of the present invention. Thus, if one has promoters P1-P8 (representing eight promoters that have been identified and/or generated to exhibit a range of expression strengths) and associates the promoter ladder with a single RNA degradation gene in a microbe (i.e., genetically engineer a microbe with a given promoter operably linked to the native, or exogenous coding region of the RNA degradation gene), then the effect of each of the eight promoters can be ascertained by characterizing each of the eight engineered strains, given that the engineered microbes have an otherwise identical genetic background except the particular promoter associated with the target gene.

Modulating the steady state levels of genes in an organism are a key point of control for effecting organism behavior. Cells express thousands of different types of proteins, and these proteins interact in numerous complex ways to create function. By varying the steady state levels of selected RNA degradosome genes, the present invention achieves In some embodiments, the present disclosure teaches specific combinations of selected promoters operably linked to selected RNA degradosome genes. A non-exclusive list of promoter::gene combinations contemplated by this disclosure are summarized in Table 3 below. In consideration of the limited space, these combinations are represented by their promoter and gene short names as defined in earlier portions of the specification.

TABLE 3

Promoter:RNA Degradosome Gene combinations of the present disclosure.

| P1::G1 | P2::G1 | P3::G1 | P4::G1 | P5::G1 | P6::G1 | P7::G1 | P8::G1 |
|---|---|---|---|---|---|---|---|
| P1::G2 | P2::G2 | P3::G2 | P4::G2 | P5::G2 | P6::G2 | P7::G2 | P8::G2 |
| P1::G3 | P2::G3 | P3::G3 | P4::G3 | P5::G3 | P6::G3 | P7::G3 | P8::G3 |
| P1::G4 | P2::G4 | P3::G4 | P4::G4 | P5::G4 | P6::G4 | P7::G4 | P8::G4 |
| P1::G5 | P2::G5 | P3::G5 | P4::G5 | P5::G5 | P6::G5 | P7::G5 | P8::G5 |
| P1::G6 | P2::G6 | P3::G6 | P4::G6 | P5::G6 | P6::G6 | P7::G6 | P8::G6 |
| P1::G7 | P2::G7 | P3::G7 | P4::G7 | P5::G7 | P6::G7 | P7::G7 | P8::G7 |
| P1::G8 | P2::G8 | P3::G8 | P4::G8 | P5::G8 | P6::G8 | P7::G8 | P8::G8 |
| P1::G9 | P2::G9 | P3::G9 | P4::G9 | P5::G9 | P6::G9 | P7::G9 | P8::G9 |
| P1::G10 | P2::G10 | P3::G10 | P4::G10 | P5::G10 | P6::G10 | P7::G10 | P8::G10 |
| P1::G11 | P2::G11 | P3::G11 | P4::G11 | P5::G11 | P6::G11 | P7::G11 | P8::G11 |
| P1::G12 | P2::G12 | P3::G12 | P4::G12 | P5::G12 | P6::G12 | P7::G12 | P8::G12 |
| P1::G13 | P2::G13 | P3::G13 | P4::G13 | P5::G13 | P6::G13 | P7::G13 | P8::G13 |
| P1::G14 | P2::G14 | P3::G14 | P4::G14 | P5::G14 | P6::G14 | P7::G14 | P8::G14 | improved host performance. Some alterations to the RNA degradosome may increase performance, and so, coupled to a mechanism for assessing performance, this technique allows for the generation of organisms with improved function.

Thus, in particular embodiments, the RNA degradation gene perturbation is a multi-step process comprising: i) selecting a promoter from the promoter ladder (e.g., from the promoters listed in Table 2 of this disclosure or a variant thereof), ii) selecting a RNA degradosome gene to target (e.g., from the genes listed in Table 1 of this disclosure or a variant thereof), and iii) operably linking the selected promoter to the selected gene in the genome of a selected host organism. In some embodiments, operably linking the selected promoter to the selected gene is performed as follows: When a native promoter exists in front of selected RNA degradosome gene and its sequence is known, replace the native promoter with the selected promoter. When the native promoter does not exist, or its sequence is unknown, insert the selected promoter in front of the RNA degradosome gene.

In some embodiments, the present disclosure will refer to a specific combination of an operably linked promoter to a selected RNA degradation gene, by reciting the promoter and gene sequences or names separated by a "::". Thus, the symbol "::" as used in this disclosure is used in lieu of "operably linked." Thus a recitation of SEQ ID NO: 1::SEQ ID NO: 22, refers to the promoter from SEQ ID NO:1 operably linked to the RNA degradation gene of SEQ ID NO: 22. Similarly, P1::G10 refers to promoter 1 from Table 2, operably linked to the mutM2 RNA degradation sequence disclosed in Table 1. In some portions of the specification, the symbol "-"is used interchangeably with"::".

In some embodiments, the present disclosure also teaches methods of validating genetically engineered host organisms comprising the operably linked promoter and RNA degradation gene by comparing the engineered host against a genetically identical host lacking the operably linked promoter, against one or more metrics is indicative of the performance that is being optimized.

Start Codon Optimization

In some embodiments, the present disclosure teaches methods of swapping start and stop codon variants. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24:216-218).

In other embodiments, the present invention teaches replacing ATG start codons with TG. In some embodiments, the present invention teaches replacing ATG start codons with GTG. In some embodiments, the present invention teaches replacing GTG start codons with ATG. In some embodiments, the present invention teaches replacing GTG start codons with TTG. In some embodiments, the present invention teaches replacing TG start codons with ATG. In some embodiments, the present invention teaches replacing TTG start codons with GTG.

Organisms Amenable to Genetic Design

The disclosed genomic engineering methods are exemplified with industrial microbial cell cultures, but are applicable to any organism.

Thus, as used herein, the term "microorganism" should be taken broadly. It includes, but is not limited to, the two prokaryotic domains, Bacteria and Archaea, as well as certain eukaryotic fungi and protists. However, in certain aspects, "higher" eukaryotic organisms such as insects, plants, and animals can be utilized in the methods taught herein.

Suitable host cells include, but are not limited to: bacterial cells, algal cells, plant cells, fungal cells, insect cells, and mammalian cells. In one illustrative embodiment, suitable host cells include *E. coli* (e.g., SHuffle™ competent *E. coli* available from New England BioLabs in Ipswich, Mass.).

In one illustrative embodiment, suitable host cells include *E. coli*. Suitable host strains of the *E. coli* species comprise: Enterotoxigenic *E. coli* (ETEC), Enteropathogenic *E. coli* (EPEC), Enteroinvasive *E. coli* (EIEC), Enterohemorrhagic *E. coli* (EHEC), Uropathogenic *E. coli* (UPEC), Verotoxin-producing *E. coli*, *E. coli* O157:H7, *E. coli* O104:H4, *Escherichia coli* O121, *Escherichia coli* O104:H21,

*Escherichia coli* K1, and *Escherichia coli* NC101. In some embodiments, the present disclosure teaches genomic engineering of *E. coli* K12, *E. coli* B, and *E. coli* C.

In some embodiments, the present disclosure teaches genomic engineering of *E. coli* strains NCTC 12757, NCTC 12779, NCTC 12790, NCTC 12796, NCTC 12811, ATCC 11229, ATCC 25922, ATCC 8739, DSM 30083, BC 5849, BC 8265, BC 8267, BC 8268, BC 8270, BC 8271, BC 8272, BC 8273, BC 8276, BC 8277, BC 8278, BC 8279, BC 8312, BC 8317, BC 8319, BC 8320, BC 8321, BC 8322, BC 8326, BC 8327, BC 8331, BC 8335, BC 8338, BC 8341, BC 8344, BC 8345, BC 8346, BC 8347, BC 8348, BC 8863, and BC 8864.

In some embodiments, the present disclosure teaches verocytotaxigenic *E. coli* (VTEC), such as strains BC 4734 (O26:H11), BC 4735 (O157:H-), BC 4736, BC 4737 (n.d.), BC 4738 (O157:H7), BC 4945 (O26:H-), BC 4946 (O157:H7), BC 4947 (O111:H-), BC 4948 (O157:H), BC 4949 (O5), BC 5579 (O157:H7), BC 5580 (O157:H7), BC 5582 (O3:H), BC 5643 (O2:H5), BC 5644 (O128), BC 5645 (O55:H-), BC 5646 (O69:H-), BC 5647 (O101:H9), BC 5648 (O103:H2), BC 5850 (O22:H8), BC 5851 (O55:H-), BC 5852 (O48:H21), BC 5853 (O26:H11), BC 5854 (O157:H7), BC 5855 (O157:H-), BC 5856 (O26:H-), BC 5857 (O103:H2), BC 5858 (O26:1111), BC 7832, BC 7833 (O raw form:H-), BC 7834 (ONT:H-), BC 7835 (O103:112), BC 7836 (O57:H-), BC 7837 (ONT:H-), BC 7838, BC 7839 (O128:H2), BC 7840 (O157:H-), BC 7841 (O23:H-), BC 7842 (O157:H-), BC 7843, BC 7844 (O157:H-), BC 7845 (O103:H2), BC 7846 (O26:H11), BC 7847 (O145:H-), BC 7848 (O157:H-), BC 7849 (O156:H47), BC 7850, BC 7851 (O157:H-), BC 7852 (O157:H-), BC 7853 (O5:H-), BC 7854 (O157:H7), BC 7855 (O157H7), BC 7856 (O26:H-), BC 7857, BC 7858, BC 7859 (ONT:H-), BC 7860 (O129:H-), BC 7861, BC 7862 (O103:H2), BC 7863, BC 7864 (O raw form:H-), BC 7865, BC 7866 (O26:H-), BC 7867 (O raw form:H-), BC 7868, BC 7869 (ONT:H-), BC 7870 (O113:H-), BC 7871 (ONT:H-), BC 7872 (ONT:H-), BC 7873, BC 7874 (O raw form:H-), BC 7875 (O157:H-), BC 7876 (O111:H-), BC 7877 (O146:H21), BC 7878 (O145:H-), BC 7879 (O22:H8), BC 7880 (O raw form:H-), BC 7881 (O145:H-), BC 8275 (O157:H7), BC 8318 (O55:K-:H-), BC 8325 (O157:H7), and BC 8332 (ONT), BC 8333.

In some embodiments, the present disclosure teaches enteroinvasive *E. coli* (EIEC), such as strains BC 8246 (O152:K-:H-), BC 8247 (O124:K(72):H3), BC 8248 (O124), BC 8249 (O112), BC 8250 (O136:K(78):H-), BC 8251 (O124:H-), BC 8252 (O144:K-:H-), BC 8253 (O143:K:H-), BC 8254 (O143), BC 8255 (O112), BC 8256 (O28a.e), BC 8257 (O124:H-), BC 8258 (O143), BC 8259 (O167:K-:H5), BC 8260 (O128a.c.:H35), BC 8261 (O164), BC 8262 (O164:K-:H-), BC 8263 (O164), and BC 8264 (O124).

In some embodiments, the present disclosure teaches enterotoxigenic *E. coli* (ETEC), such as strains BC 5581 (O78:H11), BC 5583 (O2:K1), BC 8221 (O118), BC 8222 (O148:H-), BC 8223 (O111), BC 8224 (O110:H-), BC 8225 (O148), BC 8226 (O118), BC 8227 (O25:H42), BC 8229 (O6), BC 8231 (O153:H45), BC 8232 (O9), BC 8233 (O148), BC 8234 (O128), BC 8235 (O118), BC 8237 (O111) BC 8238 (O110:H17), BC 8240 (O148), BC 8241 (O6H16), BC 8243 (O153), BC 8244 (O15:H-), BC 8245 (O20), BC 8269 (O125a.c:H-), BC 8313 (O6:H6), BC 8315 (O153:H-), BC 8329, BC 8334 (O118:H12), and BC 8339.

In some embodiments, the present disclosure teaches enteropathogenic *E. coli* (EPEC), such as strains BC 7567 (O86), BC 7568 (O128), BC 7571 (O114), BC 7572 (O119), BC 7573 (O125), BC 7574 (O124), BC 7576 (O127a), BC 7577 (O126), BC 7578 (O142), BC 7579 (O26), BC 7580 (OK26), BC 7581 (O142), BC 7582 (O55), BC 7583 (O158), BC 7584 (O-), BC 7585 (O-), BC 7586 (O-), BC 8330, BC 8550 (O26), BC 8551 (O55), BC 8552 (O158), BC 8553 (O26), BC 8554 (O158), BC 8555 (O86), BC 8556 (O128), BC 8557 (OK26), BC 8558 (O55), BC 8560 (O158), BC 8561 (O158), BC 8562 (O114), BC 8563 (O86), BC 8564 (O128), BC 8565 (O158), BC 8566 (O158), BC 8567 (O158), BC 8568 (O111), BC 8569 (O128), BC 8570 (O114), BC 8571 (O128), BC 8572 (O128), BC 8573 (O158), BC 8574 (O158), BC 8575 (O158), BC 8576 (O158), BC 8577 (O158), BC 8578 (O158), BC 8581 (O158), BC 8583 (O128), BC 8584 (O158), BC 8585 (O128), BC 8586 (O158), BC 8588 (O26), BC 8589 (O86), BC 8590 (O127), BC 8591 (O128), BC 8592 (O114), BC 8593 (O114), BC 8594 (O114), BC 8595 (O125), BC 8596 (O158), BC 8597 (O26), BC 8598 (O26), BC 8599 (O158), BC 8605 (O158), BC 8606 (O158), BC 8607 (O158), BC 8608 (O128), BC 8609 (O55), BC 8610 (O114), BC 8615 (O158), BC 8616 (O128), BC 8617 (O26), BC 8618 (O86), BC 8619, BC 8620, BC 8621, BC 8622, BC 8623, BC 8624 (O158), and BC 8625 (O158).

Other suitable host organisms of the present disclosure include microorganisms of the genus *Corynebacterium*. In some embodiments, preferred *Corynebacterium* strains/species include: *C. efficiens*, with the deposited type strain being DSM44549, *C. glutamicum*, with the deposited type strain being ATCC13032, and *C. ammoniagenes*, with the deposited type strain being ATCC6871. In some embodiments the preferred host of the present disclosure is *C. glutamicum*.

Suitable host strains of the genus *Corynebacterium*, in particular of the species *Corynebacterium glutamicum*, are in particular the known wild-type strains: *Corynebacterium glutamicum* ATCC13032, *Corynebacterium acetoglutamicum* ATCC15806, *Corynebacterium acetoacidophilum* ATCC13870, *Corynebacterium melassecola* ATCC17965, *Corynebacterium thermoaminogenes* FERM BP-1539, *Brevibacterium flavum* ATCC14067, *Brevibacterium lactofermentum* ATCC13869, and *Brevibacterium divaricatum* ATCC14020; and L-amino acid-producing mutants, or strains, prepared therefrom, such as, for example, the L-lysine-producing strains: *Corynebacterium glutamicum* FERM-P 1709, *Brevibacterium flavum* FERM-P 1708, *Brevibacterium lactofermentum* FERM-P 1712, *Corynebacterium glutamicum* FERM-P 6463, *Corynebacterium glutamicum* FERM-P 6464, *Corynebacterium glutamicum* DM58-1, *Corynebacterium glutamicum* DG52-5, *Corynebacterium glutamicum* DSM5714, and *Corynebacterium glutamicum* DSM1 2866.

The term "*Micrococcus glutamicus*" has also been in use for *C. glutamicum*. Some representatives of the species *C. efficiens* have also been referred to as *C. thermoaminogenes* in the prior art, such as the strain FERM BP-1539, for example.

In other embodiments, the host cell is a prokaryotic cell. Suitable prokaryotic cells include gram positive, gram negative, and gram-variable bacterial cells. The host cell may be a species of but not limited to: *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escheria, Enterococcus, Enterobacter, Erwinia, Fusobacterium, Faecalibacterium, Francisella, Flavobacterium, Geovacillus, Haemophilus, Helicobacter, Klebsiella, Lactobacillus, Lactococcus, Ilyobacter, Micrococcus,*

*Microbacterium, Mesorhizobium, Methylobacterium, Methylobacterium, Mycobacterium, Neisseria, Pantoea, Pseudomonas, Prochlorococcus, Rhodobacer, Rhodopseudomonas, Rhodopseudomonas, Roseburia, Rhodospirillum, Rhodococcus, Scenedesmus, Streptomyces, Streptococcus, Synecoccus, Saccharaopolyspora, Staphylococcus, Serratia, Salmonella, Shigella, Thermoanaerobacterium, Tropheryma, Tularensis, Temecula, Thermosynecococcus, Thermococcus, Ureaplasma, Xanthomonas, Xylella, Yersinia,* and *Zymomonas*. In some embodiments, the host cell is *Corynebacterium glutamicum*. In some embodiments, the bacterial host strain is an industrial strain. Numerous bacterial industrial strains are known and suitable in the methods and compositions described herein.

In some embodiments, the bacterial host cell is of the *Agrobacterium* species (e.g., *A. radiobacter, A. rhizogenes, A. rubi*), the *Arthrobacter* species (e.g., *A. aurescens, A. citreus, A. globformis, A. hydrocarboglutamicus, A. mysorens. A. nicotianae, A. paraffineus, A. protophonniae, A. roseoparaffinus, A. sulfureus, A. ureafaciens*), the *Bacillus* species (e.g., *B. thuringiensis, B. anthracis, B. megaterium, B. subtilis, B. lentus, B. circulars, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens*. In some embodiments, the host cell will be an industrial *Clostridium* species (e.g., *C. acetobutylicum, C. tetani* E88, *C. lituseburense, C. saccharobutylicum, C. perfringens, C. beijerinckii*). In some embodiments, the host cell will be an industrial *Corynebacterium* species (e.g., *C. glutamicum, C. acetoacidophilum*). In some embodiments, the host cell will be an industrial *Escherichia* species (e.g., *E. coli*). In some embodiments, the host cell will be an industrial *Erwinia* species (e.g., *E. uredovora, E. carotovora, E. ananas, E. herbicola, E. punctata, E. terreus*). In some embodiments, the host cell will be an industrial *Pantoea* species (e.g., *P. citrea, P. agglomerans*). In some embodiments, the host cell will be an industrial *Pseudomonas* species, (e.g., *P. putida, P. aeruginosa, P. mevalonii*). In some embodiments, the host cell will be an industrial *Streptococcus* species (e.g., *S. equisimiles, S. pyogenes, S. uberis*). In some embodiments, the host cell will be an industrial *Streptomyces* species (e.g., *S. ambofaciens, S. achromogenes, S. avermitilis, S. coelicolor, S. aureofaciens, S. aureus, S. fnigicidicus, S. griseus, S. lividans*). In some embodiments, the host cell will be an industrial *Zymomonas* species (e.g., *Z. mobilis, Z. lipolytica*), and the like. In some embodiments, the host cell of the present disclosure is a eukaryotic cell. Suitable eukaryotic host cells include, but are not limited to: fungal cells, algal cells, insect cells, animal cells, and plant cells. Suitable fungal host cells include, but are not limited to: Ascomycota, Basidiomycota, Deuteromycota, Zygomycota, Fungi imperfecti. Certain preferred fungal host cells include yeast cells and filamentous fungal cells. Suitable filamentous fungi host cells include, for example, any filamentous forms of the subdivision Eumycotina and Oomycota. (see, e.g., Hawksworth et al., In Ainsworth and Bisby's Dictionary of The Fungi, 8th edition, 1995, CAB International, University Press, Cambridge, UK, which is incorporated herein by reference). Filamentous fungi are characterized by a vegetative mycelium with a cell wall composed of chitin, cellulose and other complex polysaccharides. The filamentous fungi host cells are morphologically distinct from yeast.

In certain illustrative, but non-limiting embodiments, the filamentous fungal host cell may be a cell of a species of: *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthor* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces. Thermoascus, Thielavia, Tramates, Tolypocladium, Trichoderma, Verticillium, Volvariella*, or teleomorphs, or anamorphs, and synonyms or taxonomic equivalents thereof.

Suitable yeast host cells include, but are not limited to: *Candida, Hansenula, Saccharomyces, Schizosaccharomyces, Pichia, Kluyveromyces*, and *Yarrowia*. In some embodiments, the yeast cell is *Hansenula polymorpha, Saccharomyces cerevisiae, Saccharomyces carlsbergensis, Saccharomyces diastaticus, Saccharomyces noibensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria. Pichia quercuum, Pichia pijperi, Pichia stipitis, Pichia methanolica, Pichia angusta, Kluyveromyces lactis, Candida albicans*, or *Yarrowia lipolytica*.

In certain embodiments, the host cell is an algal cell such as, *Chlamydomonas* (e.g., *C. Reinhardtii*) and *Phmidium Phormidium* (*P.* sp. ATCC29409).

In some embodiments, the methods of the present disclosure are also applicable to multicellular organisms. For example, the platform could be used for improving the performance of crops. The organisms can comprise a plurality of plants such as *Gramineae, Fettucoideae, Poacoideae, Agrostis, Phleum, Dactylis, Sorgum, Setaria, Zea, Oryza, Triticum, Secale, Avena, Hordeum, Saccarum, Poa, Festuca, Stenophrum, Cynodon, Coix, Olyreae, Phareae, Compositae* or *Leguminosae*. For example, the plants can be corn, rice, soybean, cotton, wheat, rye, oats, barley, pea, beans, lentil, peanut, yam bean, cowpeas, velvet beans, clover, alfalfa, lupine, vetch, lotus, sweet clover, wisteria, sweet pea, sorghum, millet, sunflower, canola or the like. Similarly, the organisms can include a plurality of animals such as non-human mammals, fish, insects, or the like.

The present disclosure is also suitable for use with a variety of animal cell types, including mammalian cells, for example, human (including 293, WI38, PER. C6 and Bowes melanoma cells), mouse (including 3T3, NS0, NS1, Sp2/0), hamster (CHO. BHK), monkey (COS, FRhL, Vero), and hybridoma cell lines.

In various embodiments, strains that may be used in the practice of the disclosure are readily accessible to the public from a number of culture collections such as American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Assembling/Cloning Custom Plasmids

In some embodiments, the present disclosure teaches methods for constructing vectors capable of inserting desired target DNA sections (e.g. containing a particular promoter, or promoter::gene combination) into the genome of host organisms. In some embodiments, the present disclosure teaches methods of cloning vectors comprising the target DNA, homology arms, and at least one selection marker (see FIG. 1).

In some embodiments, the present disclosure is compatible with any vector suited for transformation into the host organism. In some embodiments, the present disclosure teaches use of shuttle vectors compatible with a host cell. In one embodiment, a shuttle vector for use in the methods provided herein is a shuttle vector capable of propagating in at least two different species (e.g., compatible with an *E. coli* for initial cloning/amplification and *Corynebacterium* for integration). In some embodiments, vectors for use in the methods provided herein can comprise markers for selection and/or counter-selection as described herein. The markers can be any markers known in the art and/or provided herein. The shuttle vectors can further comprise any regulatory sequence(s) and/or sequences useful in the assembly of said shuttle vectors as known in the a. The shuttle vectors can further comprise any origins of replication that may be needed for propagation in a host cell as provided herein such as, for example, *E. coli* or *C. glutamicum*. In some embodiments, the vectors of the present disclosure comprise at least one regulatory sequence. In some embodiments, the regulatory sequence can be any regulatory sequence known in the art or provided herein such as, for example, a promoter, start, stop, signal, secretion and/or termination sequence used by the genetic machinery of the host cell. In certain instances, the target DNA can be inserted into vectors, constructs or plasmids obtainable from any repository or catalogue product, such as a commercial vector (see e.g.. DNA2.0 custom or GATEWAY® vectors).

In some embodiments, the assembly/cloning methods of the present disclosure may employ at least one of the following assembly strategies: i) type II conventional cloning, ii) type II S-mediated or "Golden Gate" cloning (see, e.g., Engler, C., R. Kandzia, and S. Marillonnet. 2008 "A one pot, one step, precision cloning method with high-throughput capability". PLos One 3:e3647; Kotera, I., and T. Nagai. 2008 "A high-throughput and single-tube recombination of crude PCR products using a DNA polymerase inhibitor and type US restriction enzyme." J Biotechnol 137:1-7.; Weber, E., R. Gruetzner, S. Werner, C. Engler, and S. Marillonnet. 2011 Assembly of Designer TAL Effectors by Golden Gate Cloning. PloS One 6:e19722), iii) GATEWAY® recombination, iv) TOPO® cloning, exonuclease-mediated assembly (Aslanidis and de Jong 1990. "Ligation-independent cloning of PCR products (LIC-PCR)." Nucleic Acids Research, Vol. 18, No. 20 6069), v) homologous recombination, vi) non-homologous end joining, or a combination thereof. Modular type US based assembly strategies are disclosed in PCT Publication WO 2011/154147, the disclosure of which is incorporated herein by reference.

In some embodiments, the present disclosure teaches cloning vectors with at least one selection marker. Various selection marker genes are known in the art often encoding antibiotic resistance function for selection in prokaryotic (e.g., against ampicillin, kanamycin, tetracycline, chloramphenycol, zeocin, spectinomycin/streptomycin) or eukaryotic cells (e.g. geneticin, neomycin, hygromycin, puromycin, blasticidin, zeocin) under selective pressure. Other marker systems allow for screening and identification of wanted or unwanted cells such as the well-known blue/white screening system used in bacteria to select positive clones in the presence of X-gal or fluorescent reporters such as green or red fluorescent proteins expressed in successfully transduced host cells. Another class of selection markers most of which are only functional in prokaryotic systems relates to counter selectable marker genes often also referred to as "death genes" which express toxic gene products that kill producer cells. Examples of such genes include sacB, rpsL (strA), tetAR, pheS, thyA, gata-1, or ccdB, the function of which is described in (Reyrat et al. 1998 "Counterselectable Markers: Untapped Tools for Bacterial Genetics and Pathogenesis." Infect Immun. 66(9): 4011-4017).

Transformation of Host Cells

In some embodiments, the vectors of the present disclosure may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, L, 1986 "Basic Methods in Molecular Biology"). Other methods of transformation include for example, lithium acetate transformation and electroporation See, e.g., Gietz et al., Nucleic Acids Res. 27:69-74 (1992); Ito et al., J. Bacterol. 153:163-168 (1983); and Becker and Guarente. Methods in Enzymology 194:182-187 (1991). In some embodiments, transformed host cells are referred to as recombinant host strains.

In some embodiments, the insert DNA of the present disclosure is incorporated into the target genomic DNA region by single-crossover or double crossover recombination (see Nakashima et al., 2014 "Bacterial Cellular Engineering by Genome Editing and Gene Silencing" Int. J. Mol Sci. 15(2), 2773-2793).

In some embodiments, the present disclosure teaches screening transformed cells with one or more selection markers as described above. In one such embodiment, cells transformed with a vector comprising a kanamycin resistance marker (KanR) are plated on media containing effective amounts of the kanamycin antibiotic. Colony forming units visible on kanamycin-laced media are presumed to have incorporated the vector cassette into their genome. Insertion of the desired sequences can be confirmed via PCR, restriction enzyme analysis, and/or sequencing of the relevant insertion site.

Looping Out of Selected Sequences

In some embodiments, the present disclosure teaches methods of looping out selected regions of DNA from the host organisms. In some embodiments, the present disclosure teaches looping out selection markers from positive transformants. Looping out deletion techniques are known in the art, and are described in (Tear et al. 2014 "Excision of Unstable Artificial Gene-Specific inverted Repeats Mediates Scar-Free Gene Deletions in *Escheria coli*." Appl. Biochem. Biotech. 175:1858-1867).

The looping out methods used in the methods provided herein can be performed using single-crossover homologous recombination or double-crossover homologous recombination. In one embodiment, looping out of selected regions as described herein is performed using single-crossover homologous recombination.

Figure 2:
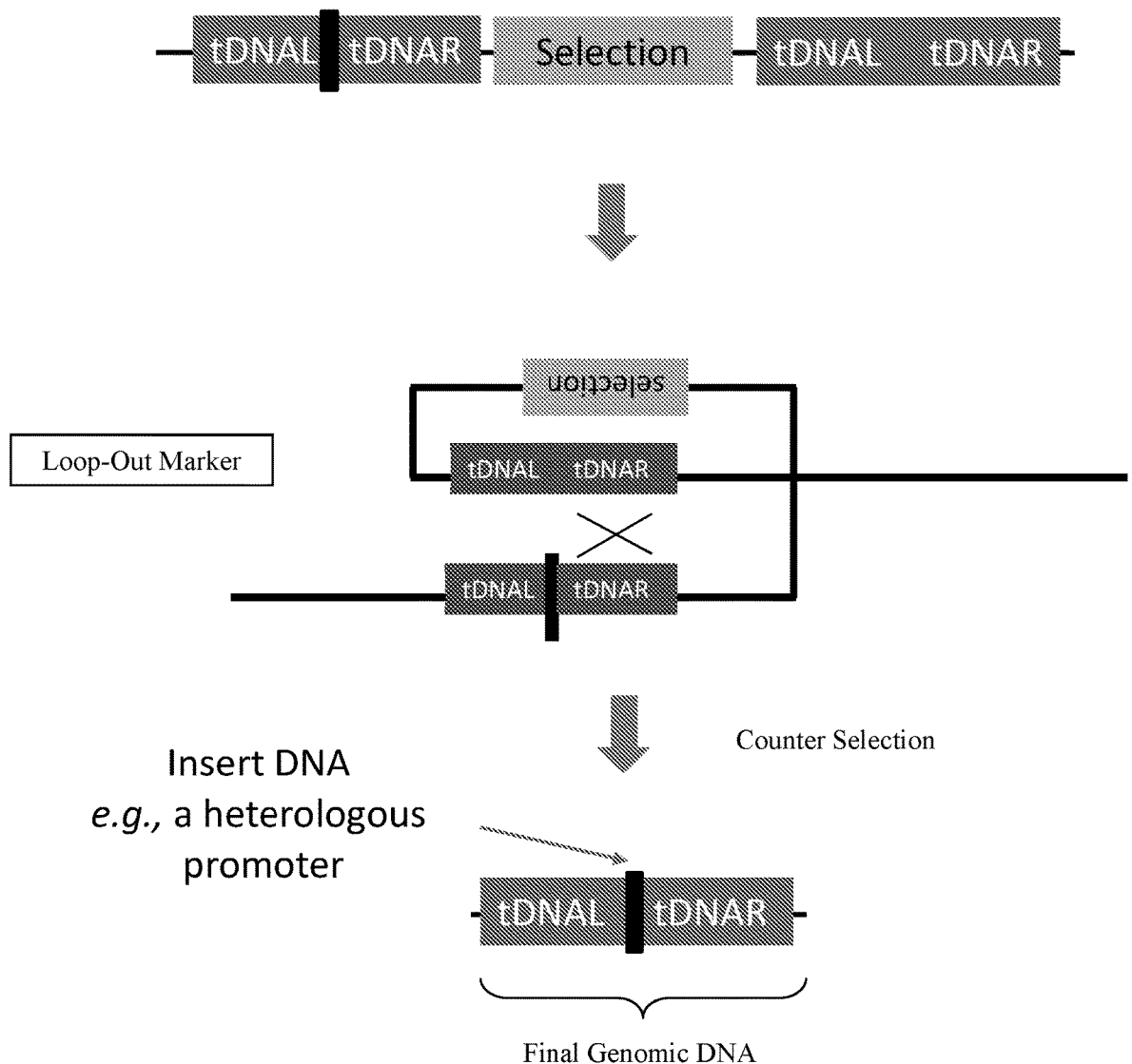
FIG. 2 depicts procedure for looping-out selected regions of DNA from host strains. Direct repeat regions of the inserted DNA and host genome can "loop out" in a recombination event. Cells counter selected for the selection marker contain deletions of the loop DNA flanked by the direct repeat regions.

First, loop out vectors are inserted into selected target regions within the genome of the host organism (e.g., via homologous recombination, CRISPR, or other gene editing technique). The inserted vector is designed with a sequence which is a direct of an existing or introduced nearby host sequence, such that the direct repeats flank the region of DNA slated for looping and deletion. Once inserted, cells containing the loop out vector can be counter selected for deletion of the selection region (e.g., lack of resistance to the selection gene). In one such embodiment, a SNP is inserted in a loopout vector in which the selection marker is flanked by the direct repeat sequences. Insertion of the vector is confirmed through its selection marker. Once confirmed, the selection marker is then removed by selecting for a looping out of the DNA slated for deletion (see FIG. 2).

Cell Culture and Fermentation

Cells of the present disclosure can be cultured in conventional nutrient media modified as appropriate for any desired biosynthetic reactions or selections. In some embodiments, the present disclosure teaches culture in inducing media for activating promoters. In some embodiments, the present disclosure teaches media with selection agents, including selection agents of transformants (e.g., antibiotics), or selection of organisms suited to grow under inhibiting conditions (e.g., high ethanol conditions). In some embodiments, the present disclosure teaches growing cell cultures in media optimized for cell growth. In other embodiments, the present disclosure teaches growing cell cultures in media optimized for product yield. In some embodiments, the present disclosure teaches growing cultures in media capable of inducing cell growth and also contains the necessary precursors for final product production (e.g., high levels of sugars for ethanol production).

Culture conditions, such as temperature, pH and the like, are those suitable for use with the host cell selected for expression, and will be apparent to those skilled in the art. As noted, many references are available for the culture and production of many cells, including cells of bacterial, plant, animal (including mammalian) and archebacterial origin. See e.g., Sambrook, Ausubel (all supra), as well as Berger, *Guide to Molecular Cloning Techniques, Method in Enzymology* volume 152 Academic Press, Inc., San Diego, Calif.; and Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelle et al., (1989) *In Viro Cell Dev. Biol.* 25:1016-1024, all of which are incorporated herein by reference. For plant cell culture and regeneration, Payne et al. (1992) *Plant Cell and Tissue Culture in Liquid System* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 012 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* from Sigma-Aldrich, Inc. (St Louis, Mo.) ("Sigma-LSRCCC") and, for example, *The Plant Culture Catalogue* and supplement also from Sigma-Aldrich, Inc. (St Louis, Mo.) ("Sigma-PCCS") all of which are incorporated herein by reference.

The culture medium to be used must in a suitable manner satisfy the demands of the respective strains. Descriptions of culture media for various microorganisms are present in the "Manual of Methods for General Bacteriology" of the American Society for Bacteriology (Washington D.C., USA, 1981).

The present disclosure furthermore provides a process for fermentative preparation of a product of interest, comprising the steps of a) culturing a microorganism according to the present disclosure in a suitable medium, resulting in a fermentation broth; and b) concentrating the product of interest in the fermentation broth of a) and/or in the cells of the microorganism.

In some embodiments, the present disclosure teaches that the microorganisms produced may be cultured continuously—as described, for example, in WO 05/021772—or discontinuously in a batch process (batch cultivation) or in a fed-batch or repeated fed-batch process for the purpose of producing the desired organic-chemical compound. A summary of a general nature about known cultivation methods is available in the textbook by Chmiel (Bioprozestechnik. 1: Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

In some embodiments, the cells of the present disclosure are grown under batch or continuous fermentations conditions.

Classical batch fermentation is a closed system, wherein the compositions of the medium is set at the beginning of the fermentation and is not subject to artificial alternations during the fermentation. A variation of the batch system is a fed-batch fermentation which also finds use in the present disclosure. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art.

Continuous fermentation is a system where a defined fermentation medium is added continuously to a bioreactor and an equal amount of conditioned medium is removed simultaneously for processing and harvesting of desired proteins. In some embodiments, continuous fermentation generally maintains the cultures at a constant high density where cells are primarily in log phase growth. In some embodiments, continuous fermentation generally maintains the cultures at a stationary or late log/stationary, phase growth. Continuous fermentation systems strive to maintain steady state growth conditions.

Methods for modulating nutrients and growth factors for continuous fermentation processes as well as techniques for maximizing the rate of product formation are well known in the art of industrial microbiology.

For example, a non-limiting list of carbon sources for the cultures of the present disclosure include, sugars and carbohydrates such as, for example, glucose, sucrose, lactose, fructose, maltose, molasses, sucrose-containing solutions from sugar beet or sugar cane processing, starch, starch hydrolysate, and cellulose; oils and fats such as, for example, soybean oil, sunflower oil, groundnut oil and coconut fat; fatty acids such as, for example, palmitic acid, stearic acid, and linoleic acid; alcohols such as, for example, glycerol, methanol, and ethanol; and organic acids such as, for example, acetic acid or lactic acid.

A non-limiting list of the nitrogen sources for the cultures of the present disclosure include, organic nitrogen-containing compounds such as peptones, yeast extract, meat extract, malt extract, corn steep liquor, soybean flour, and urea; or inorganic compounds such as ammonium sulfate, ammonium chloride, ammonium phosphate, ammonium carbonate, and ammonium nitrate. The nitrogen sources can be used individually or as a mixture.

A non-limiting list of the possible phosphorus sources for the cultures of the present disclosure include phosphoric acid, potassium dihydrogen phosphate or dipotassium hydrogen phosphate or the corresponding sodium-containing salts.

The culture medium may additionally comprise salts, for example in the form of chlorides or sulfates of metals such as, for example, sodium, potassium, magnesium, calcium and iron, such as, for example, magnesium sulfate or iron sulfate, which are necessary for growth.

Finally, essential growth factors such as amino acids, for example homoserine and vitamins, for example thiamine, biotin or pantothenic acid, may be employed in addition to the abovementioned substances.

In some embodiments, the pH of the culture can be controlled by any acid or base, or buffer salt, including, but not limited to sodium hydroxide, potassium hydroxide, ammonia, or aqueous ammonia; or acidic compounds such as phosphoric acid or sulfuric acid in a suitable manner. In some embodiments, the pH is generally adjusted to a value of from 6.0 to 8.5, preferably 6.5 to 8.

In some embodiments, the cultures of the present disclosure may include an anti-foaming agent such as, for example, fatty acid polyglycol esters. In some embodiments the cultures of the present disclosure are modified to stabilize the plasmids of the cultures by adding suitable selective substances such as, for example, antibiotics.

In some embodiments, the culture is carried out under aerobic conditions. In order to maintain these conditions, oxygen or oxygen-containing gas mixtures such as, for example, air are introduced into the culture. It is likewise possible to use liquids enriched with hydrogen peroxide. The fermentation is carried out, where appropriate, at elevated pressure, for example at an elevated pressure of from 0.03 to 0.2 MPa. The temperature of the culture is normally from 20° C. to 45° C. and preferably from 25° C. to 40° C., particularly preferably from 30° C. to 37° C. In batch or fed-batch processes, the cultivation is preferably continued until an amount of the desired product of interest (e.g. an organic-chemical compound) sufficient for being recovered has formed. This aim can normally be achieved within 10 hours to 160 hours. In continuous processes, longer cultivation times are possible. The activity of the microorganisms results in a concentration (accumulation) of the product of interest in the fermentation medium and/or in the cells of said microorganisms.

In some embodiments, the culture is carried out under anaerobic conditions.

Validating Genetically Engineered Strains

In some embodiments, the present disclosure teaches methods of validating genetically engineered strains comprising the selected promoter operably linked to the selected RNA degradation gene. In some embodiments, validation comprises comparing the genetically engineered strain to a control strain. In some embodiments, the control strain is a genetically identical strain, which lacks the promoter::RNA degradation gene modification of the genetically engineered strain. Thus in some embodiments, the present disclosure teaches methods of comparing the host performance of the genetically engineered strain to those of the control strain. In some embodiments, enhanced host performance will be measured against a specific selection goal, as described below.

Selection Criteria and Goals

The testing criteria applied to the methods of the present disclosure will vary with the specific goals of the strain improvement program. The present disclosure may be adapted to meet any program goals. For example, in some embodiments, the program goal may be to maximize single batch yields of reactions with no immediate time limits. In other embodiments, the program goal may be to rebalance biosynthetic yields to produce a specific product, or to produce a particular ratio of products. In other embodiments, the program goal may be to modify the chemical structure of a product, such as lengthening the carbon chain of a polymer. In some embodiments, the program goal may be to improve performance characteristics such as yield, titer, productivity, by-product elimination, tolerance to process excursions, optimal growth temperature and growth rate. In some embodiments, the program goal is improved host performance as measured by volumetric productivity, specific productivity, yield or titer, of a product of interest produced by a host cell.

In other embodiments, the program goal may be to optimize synthesis efficiency of a commercial strain in terms of final product yield per quantity of inputs (e.g., total amount of ethanol produced per pound of sucrose). In some embodiments, the program goal may be to optimize percent yield. In other embodiments, the program goal may be to optimize synthesis speed, as measured for example in terms of batch completion rates, or yield rates in continuous culturing systems. In other embodiments, the program goal may be to increase strain resistance to a particular phage, or otherwise increase strain vigor/robustness under culture conditions. In yet other embodiments, the program goal may be to improve the strain growth rate (e.g., saturation biomass).

In some embodiments, strain improvement projects may be subject to more than one goal. In some embodiments, the goal of the strain project may hinge on quality, reliability, or overall profitability. In some embodiments, the present disclosure teaches methods of associated selected mutations or groups of mutations with one or more of the strain properties described above.

Persons having ordinary skill in the art will recognize how to tailor strain testing criteria to meet the particular project goal. For example, selections of a strain's single batch max yield at reaction saturation may be appropriate for identifying strains with high single batch yields. Selection based on consistency in yield across a range of temperatures and conditions may be appropriate for identifying strains with increased robustness and reliability.

In some embodiments, the selection criteria for the initial small-batch phase and the tank-based validation will be identical. In other embodiments, tank-based selection may operate under additional and/or different selection criteria. For example, in some embodiments, high-throughput strain selection might be based on single batch reaction completion yields, while tank-based selection may be expanded to include selections based on yields for reaction speed.

In some embodiments, the genetically engineered host cells of the present disclosure exhibit moderate performance increases over control cells. In some embodiments, the genetically engineered host cells of the present disclosure comprising a selected heterologous promoter polynucleotide operably linked to a selected RNA degradation gene will exhibit at least a 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, 5.1%, 5.2%, 5.3%, 5.4%, 5.5%, 5.6%, 5.7%, 5.8%, 5.9%, 6%, 6.1%, 6.2%, 6.3%, 6.4%, 6.5%, 6.6%, 6.7%, 6.8%, 6.9%, 7%, 7.1%, 7.2%, 7.3%, 7.4%, 7.5%, 7.6%, 7.7%, 7.8%, 7.9%, 8%, 8.1%, 8.2%, 8.3%, 8.4%, 8.5%, 8.6%, 8.7%, 8.8%, 8.9%, 9%, 9.1%, 9.2%, 9.3%, 9.4%, 9.5%, 9.6%, 9.7%, 9.8%, 9.9%, or 10.0% increase in performance when compared to a genetically identical host cell lacking the heterologous promoter polynucleotide. In some embodiments, the present disclosure teaches various ways of measuring performance, including—but not limited to—a microbe's yield, percent yield, productivity, or saturation biomass. A person skilled in the art would thus understand that the presently disclosed percentages or fold increases of microbe performance may refer to any performance increase disclosed herein. In some embodiments, increased performance percentages refer directly to increases in yield compared to a genetically identical host cell lacking the heterologous promoter polynucleotide.

In some embodiments, the genetically engineered host cells of the present disclosure exhibit good performance increases over control cells. In some embodiments, the genetically engineered host cells of the present disclosure comprising a selected heterologous promoter polynucleotide operably linked to a selected RNA degradation gene will exhibit at least a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 103%, 109%, 110%, 111%, 112%, 113%, 114%, 115%, 116%, 117%, 113%, 119%, 120%, 121%, 122%, 123%, 124%, 125%, 126%, 127%, 123%, 129%, 130%, 131%, 132%, 133%, 134%, 135%, 136%, 137%, 138%, 139%, 140%, 141%, 142%, 143%, 144%, 145%, 146%, 147%, 143%, 149%, 150%, 151%, 152%, 153%, 154%, 155%, 156%, 157%, 153%, 159%, 160%, 161%, 162%, 163%, 164%, 165%, 166%, 167%, 168%, 169%, 170%, 171%, 172%, 173%, 174%, 175%, 176%, 177%, 173%, 179%, 180%, 181%, 182%, 183%, 184%, 185%, 186%, 187%, 188%, 189%, 190%, 191%, 192%, 193%, 194%, 195%, 196%, 197%, 193%, 199%, or 200% increase in performance when compared to a genetically identical host cell lacking the heterologous promoter polynucleotide.

In some embodiments, the genetically engineered host cells of the present disclosure exhibit stellar performance increases over control cells. In some embodiments, the genetically engineered host cells of the present disclosure comprising a selected heterologous promoter polynucleotide operably linked to a selected RNA degradation gene will exhibit at least a 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold or more, increase in performance when compared to a genetically identical host cell lacking the heterologous promoter polynucleotide. In some embodiments, the increased performance is messed by a productivity measure selected from the group consisting of volumetric productivity, specific productivity, yield, titer, and total titer. In some embodiments, the increased performance is host-cell yield of the desired product. In some embodiments, performance is determined by saturation biomass. In some embodiments, the present disclosure teaches that genetically engineered host cells with other perturbations of one or more RNA degradation genes can also exhibit moderate, good, and stellar performance improvements as described above. For example, in some embodiments, host cells with a mutated RNA degradation gene (e.g., a mutated start codon), can exhibit moderate (1-10%), good (1-200%), or stellar (2-20-fold) increase in performance over a control cells.

Product Recovery and Quantification

Methods for analyzing the production of products of interest are known to those of skill in the art and are discussed throughout the present specification. Such methods may be employed when screening the strains of the disclosure.

In some embodiments, the present disclosure teaches methods of improving strains designed to produce non-secreted intracellular products. For example, the present disclosure teaches methods of improving the robustness, yield, efficiency, or overall desirability of cell cultures producing intracellular enzymes, oils, pharmaceuticals, or other valuable small molecules or peptides. The recovery or isolation of non-secreted intracellular products can be achieved by lysis and recovery techniques that are well known in the art, including those described herein.

For example, in some embodiments, cells of the present disclosure can be harvested by centrifugation, filtration, settling, or other method. Harvested cells are then disrupted by any convenient method, including freeze-thaw cycling, sonication, mechanical disruption, or use of cell lysing agents, or other methods, which are well known to those skilled in the an.

The resulting product of interest, e.g. a polypeptide, may be recovered/isolated and optionally purified by any of a number of methods known in the art. For example, a product polypeptide may be isolated from the nutrient medium by conventional procedures including, but not limited to: centrifugation, filtration, extraction, spray-drying, evaporation, chromatography (e.g., ion exchange, affinity, hydrophobic interaction, chromatofocusing, and size exclusion), or precipitation. Finally, high performance liquid chromatography (HPLC) can be employed in the final purification steps. (See for example Purification of intracellular protein as described in Parry et al., 2001, *Biochem. J.* 353:117, and Hong et al., 2007, *Appl. Microbiol. Biotechnol.* 73:1331, both incorporated herein by reference).

In addition to the references noted supra, a variety of purification methods are well known in the art, including, for example, those set forth in: Sandana (1997) *Bioseparation of Proteins*, Academic Press, Inc.; Bollag el al. (1996) *Protein Methods, 2$^{nd}$ Edition*, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England: Harris and Angal *Protein Purification Methods: A Practical Approach*, IRL Press at Oxford, Oxford, England; Scopes (1993) *Protein Purification: Principles and Practice 3$^{rd}$* Edition, Springer Verlag, NY; Janson and Ryden (1998) *Protein Purification: Principles High Resolution Methods and Applications*, Second Edition, Wiley-VCH, NY; and Walker (1998) *Protein Protocols on CD-ROM*, Humana Press, NJ, all of which are incorporated herein by reference.

In some embodiments, the present disclosure teaches the methods of improving strains designed to produce secreted products. For example, the present disclosure teaches methods of improving the robustness, yield, efficiency, or overall desirability of cell cultures producing valuable small molecules or peptides.

In some embodiments, immunological methods may be used to detect and/or purify secreted or non-secreted products produced by the cells of the present disclosure. In one example approach, antibody raised against a product molecule (e.g., against an insulin polypeptide or an immunogenic fragment thereof) using conventional methods is immobilized on beads, mixed with cell culture media under conditions in which the endoglucanase is bound, and precipitated. In some embodiments, the present disclosure teaches the use of enzyme-linked immunosorbent assays (ELISA).

In other related embodiments, immunochromatography is used, as disclosed in U.S. Pat. Nos. 5,591,645, 4,855,240, 4,435,504, 4,980,298, and Se-Hwan Paek, et al., "Development of rapid One-Step Immunochromatographic assay, Methods", 22, 53-60, 2000), each of which are incorporated by reference herein. A general immunochromatography detects a specimen by using two antibodies. A first antibody exists in a test solution or at a portion at an end of a test piece in an approximately rectangular shape made from a porous membrane, where the test solution is dropped. This antibody is labeled with latex particles or gold colloidal particles (this antibody will be called as a labeled antibody hereinafter). When the dropped test solution includes a specimen to be detected, the labeled antibody recognizes the specimen so as to be bonded with the specimen. A complex of the specimen and labeled antibody flows by capillarity toward an absorber, which is made from a filter paper and attached to an end opposite to the end having included the labeled antibody. During the flow, the complex of the specimen and labeled antibody is recognized and caught by a second antibody (it will be called as a tapping antibody hereinafter) existing at the middle of the porous membrane and, as a result of this, the complex appears at a detection part on the porous membrane as a visible signal and is detected.

In some embodiments, the screening methods of the present disclosure are based on photometric detection techniques (absorption, fluorescence). For example, in some embodiments, detection may be based on the presence of a fluorophore detector such as GFP bound to an antibody. In other embodiments, the photometric detection may be based on the accumulation on the desired product from the cell culture. In some embodiments, the product may be detectable via UV of the culture or extracts from said culture.

Example 1—Evaluation of Candidate Promoter Activity

To evaluate candidate promoter activity, a set of plasmid based fluorescence reporter constructs was designed. Briefly, each promoter was cloned in front of eyjp, a gene encoding yellow fluorescent protein in the shuttle vector pK18rep. These plasmids were transformed into *C. glutamicum* NRRL B-11474 and promoter activity was assessed by measuring the accumulation of YFP protein by spectrometry.

The shuttle vector pK18rep was constructed by replacing the sacB gene in pK18mobSacB (ATCC 87087) with the pBL1 origin of replication (GenBank: AF092037.1) resulting in a vector able to propagate in both *E. coli* and *C. glutamicum*.

*C. glutamicum* host cells transformed with eyfb pK18rep plasmids comprising each of the selected promoters from SEQ ID Nos 1-8 were selected on BHI agar plus 25 μg/mL Kanamycin. For each transformation, multiple single colonies were picked and inoculated into individual wells of a 96 mid-well block containing 300 μL of BHI media plus 25 μg/mL Kanamycin. The cells were grown to saturation by incubation for 48 h at 30° C. shaking at 1,000 rpm.

After incubation, cultures were centrifuged for 5 min at 3,500 rpm and the media was removed by aspiration. Cells were washed once by resuspension in 300 μL of PBS and centrifugation for 5 min at 3,500 rpm followed by aspiration of the supernatant and a final resuspension in 300 5 μL of PBS. A 20 μL aliquot of this mixture was transferred to a 96-well full area black clear bottom assay plate containing 180 μL of PBS. The optical density of the cells at 600 nm was measured with the SpectraMax M5 microplate reader and the fluorescence was measured with the TECAN M1000 microplate leader by exciting at 514 nm and measuring emission at 527 nm. For each well a normalized fluorescence activity was calculated by dividing fluorescence by optical density.

Host cells transformed with the parent plasmid pK18rep acted as a negative control. Normalized fluorescence activity was compared between reporter constructs and between biological replicates. A numerical summary of promoter activity is presented in Table 4 below.

TABLE 4

Expression strength of selected promoters.

| SEQ ID No. | Promoter Expression Strength (Mean) | Standard Deviation | Standard Error of Mean | No. of Replicates |
| --- | --- | --- | --- | --- |
| 1 | 114402 | 52987.9 | 15296 | 12 |
| 2 | 89243 | 16162.2 | 3708 | 19 |
| 3 | 44527 | 18110.3 | 4155 | 19 |
| 4 | 43592 | 3643 | 1152 | 10 |
| 5 | 11286 | 10459.4 | 3154 | 11 |
| 6 | 4723 | 1854.3 | 425 | 19 |
| 7 | 661 | 731.9 | 173 | 18 |
| 8 | 98 | 537.5 | 144 | 14 |
| Control | −45 | 214.9 | 48 | 20 |

The entire disclosures of U.S. Patent Application No. 62/264,232, filed on Dec. 7, 2015, and PCT Publication No. WO2017/100376 are each hereby incorporated by reference in its entirety for all purposes.

Example 2—Effect of Promoter Perturbation on Saturation Biomass

Promoter::gene combinations of the present disclosure were empirically tested to determine their effect on culture saturation biomass.

Targets for perturbation of the *C. glutamicum* RNA degradosome were selected based on their annotation in the KEGG database (http://www.genome.jp/kegg/kegg1.html) as disclosed in the Table 1 of the present disclosure. The native promoter for each of the targeted genes was determined based on a literature search. A list of the identified native promoter is provided in Table 5 below.

TABLE 5

Identified Native Promoter Sequences

| Gene Target | Short Name | Identified Native Promoter Sequence | Number of Base Pairs Replaced (From Start Codon) |
| --- | --- | --- | --- |
| cg1144 | G1 | SEQ ID No: 23 | 101 |
| cg2453 | G2 | SEQ ID No: 24 | 61 |
| cshA | G3 | SEQ ID No: 25 | 62 |
| dnak | G4 | SEQ ID No: 26 | 179 |

TABLE 5-continued

Identified Native Promoter Sequences

| Gene Target | Short Name | Identified Native Promoter Sequence | Number of Base Pairs Replaced (From Start Codon) |
|---|---|---|---|
| eno | G5 | SEQ ID No: 27 | 129 |
| gpsI | G6 | SEQ ID No: 28 | 154 |
| groEL | G7 | SEQ ID No: 29 | 205 |
| groEL2 | G9 | None Identified | 0 |
| mutM2 | G10 | SEQ ID No: 30 | 59 |
| rhlE | G11 | SEQ ID No: 31 | 59 |
| rho | G12 | SEQ ID No: 32 | 101 |
| me | G13 | SEQ ID No: 33 | 140 |
| cg2160/RNAse J | G14 | None Identified | 0 |

If available, the entire native promoter sequence was replaced with each of promoters of the present disclosure as outlined in Table 5 above. If no native promoter could be identified, each of S8 promoters in the promoter ladder was inserted directly 5' of the target's start codon.

Plasmids to make these changes in the *C. glutamicum* genome were generated using yeast homologous recombination and were then propagated in *E. coli*. Each plasmid was built from a common backbone into which ~2 kb homologous regions were inserted that flank the location of the genomic edit. These homologous regions were PCR amplified from *C. glutamicum* genomic DNA. In between these 2 kb homologous regions, the new promoter or start codon was encoded in the 5' end of the primer used to PCR the homologous region.

Plasmids were sequence confirmed and then electroporated into *C. glutamicum*. After selection for genomic integration, plasmid backbone DNA was removed using the loopout counter selection methods of the present disclosure. Correctly built *C. glutamicum* strains were confirmed by PCR and sequencing.

Correctly built genetically engineered *C. glutamicum* strains were consolidated and then propagated in small scale cultures designed to assess saturation biomass performance. Small-scale cultures conducted using media reflective of media from industrial scale cultures. Saturation biomass was measured by determining OD600 of cultures at 96 hrs. Data from this small-scale test is included in Table 6 below. Promoter::Gene combinations exhibiting the best improvements in biomass are highlighted. A visual representation of the results from this experiment is provided in FIGS. 3A and 3B.

Figure 3A:
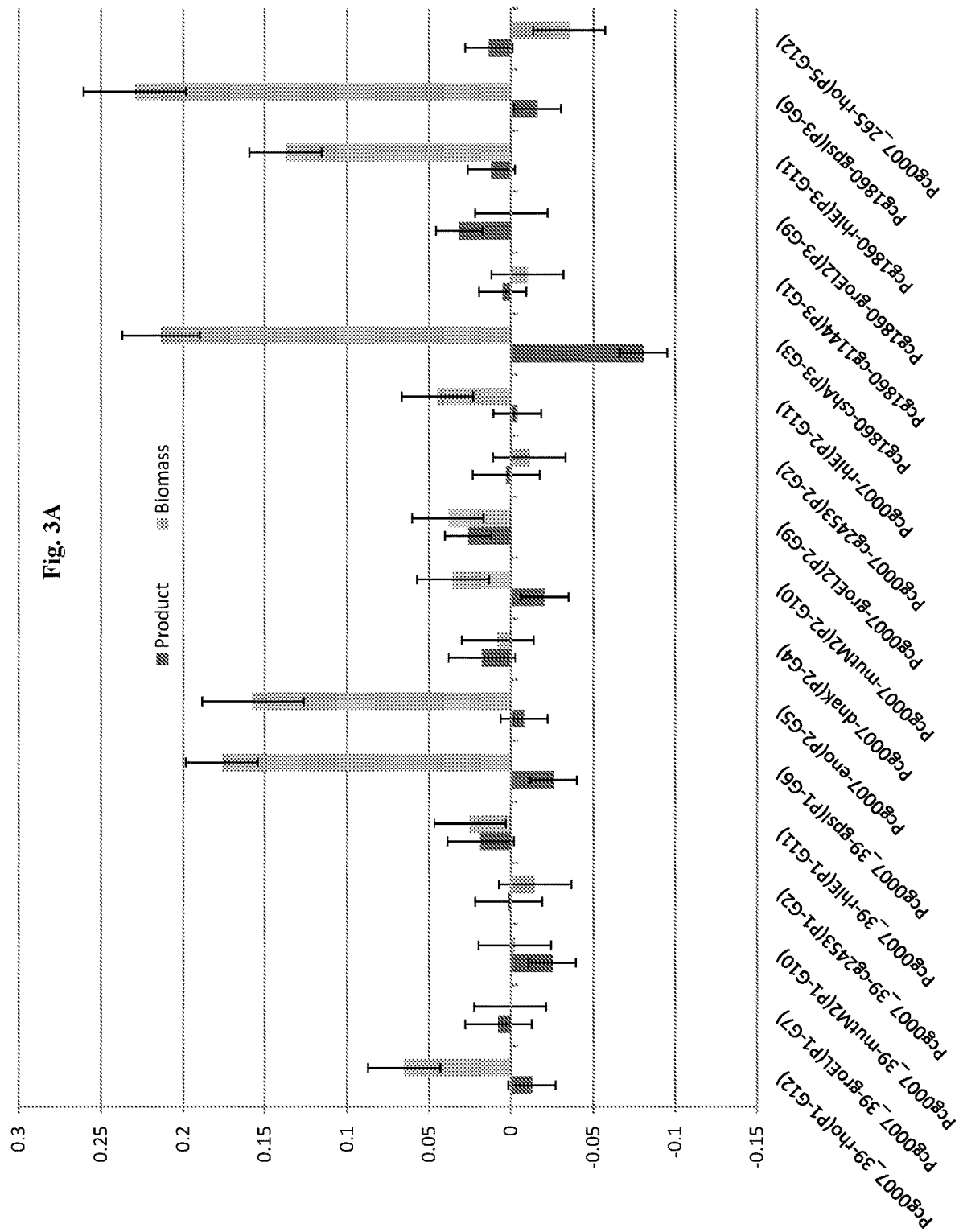
FIGS. 3A and 3B depict the results of several RNA degradation gene perturbation experiments, according to the methods of the present disclosure. The performance of genetically engineered treatment host cells comprising a heterologous promoter operably linked to a selected RNA degradation enzyme gene was determined. Bars on the graph represent a percent change in saturation biomass or product yield of the genetically engineered host cells over a control culture. Control cultures were genetically identical to the genetically modified cultures, except for lacking the operably linked heterologous promoters of the present disclosure. Error bars represent two standard deviations. Results are spread across FIGS. 3A and 3B to accommodate for the size of the data.
Figure 3B:
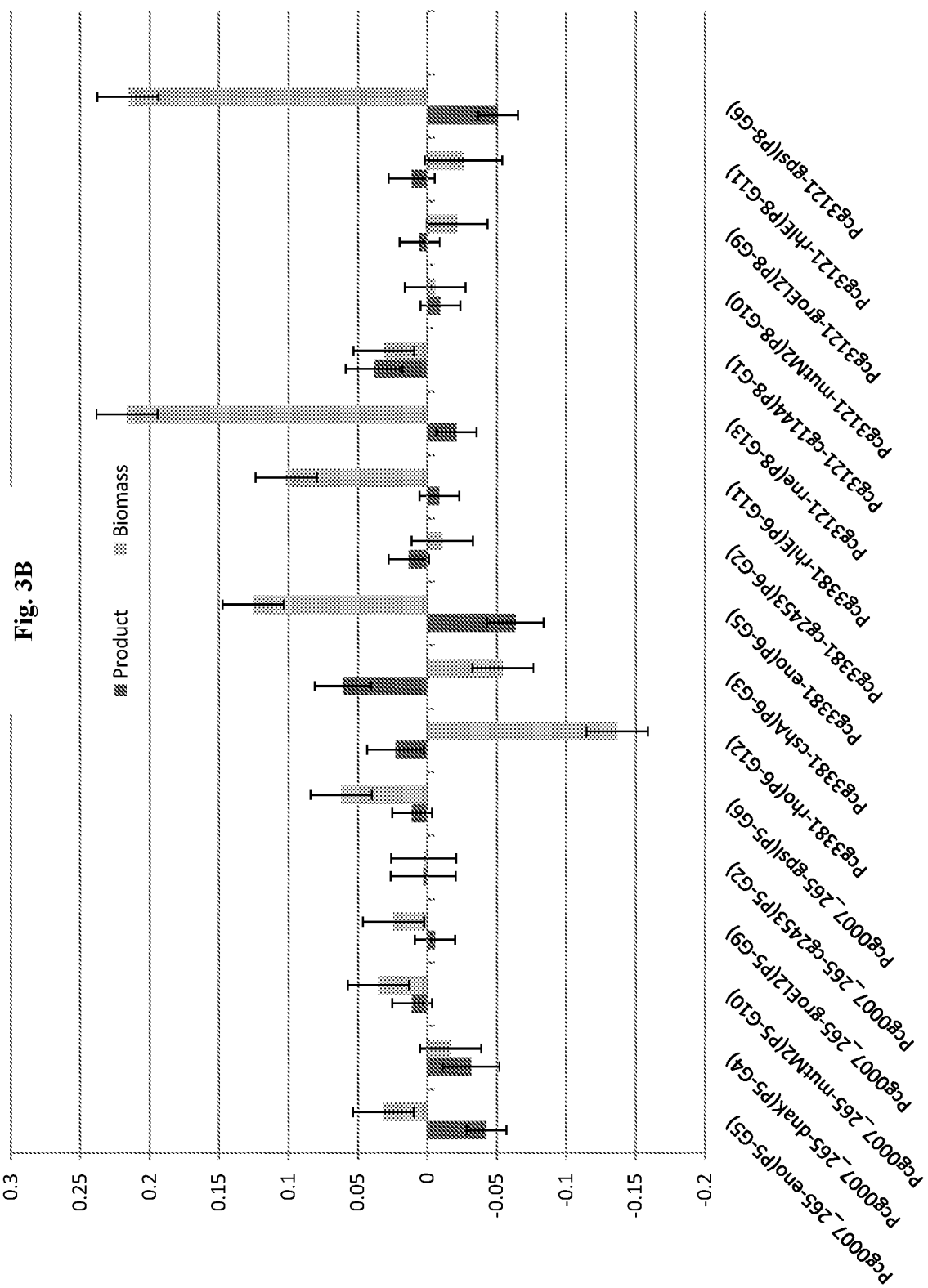

The results as outlined in FIGS. 3A and 3B demonstrated that promoter Pcg1860 (P3, SEQ ID NO: 3) was particularly effective when operably linked with cshA (G3, SEQ ID NO: 11) and gpsI (G6, SEQ ID NO: 6) at increasing saturation biomass.

The results further demonstrated that promoter Pcg3121 (P8, SEQ ID NO: 8) was particularly effective when operably linked with gpsI (G6, SEQ ID NO: 6) and me (G13, SEQ ID NO: 21) at increasing saturation biomass.

TABLE 6

Effect of Various Promoter::Gene combinations on Culture Biomass

| Number of replicates | Promoter Short Name | Gene Short name | Mean Saturation Biomass value OD600 | Std Error | Lower 95% | Upper 95% | percent performance change from parent | sigma |
|---|---|---|---|---|---|---|---|---|
| 91 | WT | reference control | 0.23611 | 0.00064 | 0.2348 | 0.2374 | | |
| 48 | Control | Promoter Parent Strain | 0.19739 | 0.00089 | 0.1957 | 0.1991 | | |
| 8 | P1 | G12 | 0.21027 | 0.00217 | 0.206 | 0.2145 | 6.5% | 1.1% |
| 8 | P1 | G7 | 0.19747 | 0.00217 | 0.1932 | 0.2017 | 0.0% | 1.1% |
| 8 | P1 | G10 | 0.1969 | 0.00217 | 0.1926 | 0.2012 | -0.2% | 1.1% |
| 8 | P1 | G2 | 0.19447 | 0.00217 | 0.1902 | 0.1987 | -1.5% | 1.1% |
| 8 | P1 | G11 | 0.20231 | 0.00217 | 0.198 | 0.2066 | 2.5% | 1.1% |
| 8 | P1 | G6 | 0.23219 | 0.00217 | 0.2279 | 0.2364 | 17.6% | 1.1% |
| 4 | P2 | G5 | 0.22844 | 0.00307 | 0.2224 | 0.2345 | 15.7% | 1.6% |
| 8 | P2 | G4 | 0.19898 | 0.00217 | 0.1947 | 0.2032 | 0.8% | 1.1% |
| 8 | P2 | G10 | 0.20436 | 0.00217 | 0.2001 | 0.2086 | 3.5% | 1.1% |
| 8 | P2 | G9 | 0.20499 | 0.00217 | 0.2007 | 0.2093 | 3.9% | 1.1% |
| 8 | P2 | G2 | 0.19516 | 0.00217 | 0.1909 | 0.1994 | -1.1% | 1.1% |
| 8 | P2 | G11 | 0.20623 | 0.00217 | 0.202 | 0.2105 | 4.5% | 1.1% |
| 7 | P3 | G3 | 0.23954 | 0.00232 | 0.235 | 0.2441 | 21.4% | 1.2% |
| 8 | P3 | G1 | 0.19539 | 0.00217 | 0.1911 | 0.1997 | -1.0% | 1.1% |
| 8 | P3 | G9 | 0.19734 | 0.00217 | 0.1931 | 0.2016 | 0.0% | 1.1% |
| 8 | P3 | G11 | 0.22449 | 0.00217 | 0.2202 | 0.2288 | 13.7% | 1.1% |
| 4 | P3 | G6 | 0.24268 | 0.00307 | 0.2367 | 0.2487 | 22.9% | 1.6% |
| 8 | P5 | G12 | 0.19038 | 0.00217 | 0.1861 | 0.1946 | -3.6% | 1.1% |
| 8 | P5 | G7 | 0.19095 | 0.00217 | 0.1867 | 0.1952 | -3.3% | 1.1% |
| 8 | P5 | G5 | 0.20366 | 0.00217 | 0.1994 | 0.2079 | 3.2% | 1.1% |
| 8 | P5 | G4 | 0.19408 | 0.00217 | 0.1898 | 0.1983 | -1.7% | 1.1% |
| 8 | P5 | G10 | 0.20437 | 0.00217 | 0.2001 | 0.2086 | 3.5% | 1.1% |
| 8 | P5 | G9 | 0.2022 | 0.00217 | 0.1979 | 0.2065 | 2.4% | 1.1% |
| 7 | P5 | G2 | 0.19791 | 0.00232 | 0.1934 | 0.2025 | 0.3% | 1.2% |
| 8 | P5 | G6 | 0.20965 | 0.00217 | 0.2054 | 0.2139 | 6.2% | 1.1% |
| 8 | P6 | G12 | 0.17041 | 0.00217 | 0.1661 | 0.1747 | -13.7% | 1.1% |
| 8 | P6 | G3 | 0.18666 | 0.00217 | 0.1824 | 0.1909 | -5.4% | 1.1% |
| 8 | P6 | G5 | 0.22218 | 0.00217 | 0.2179 | 0.2264 | 12.6% | 1.1% |
| 8 | P6 | G2 | 0.19527 | 0.00217 | 0.191 | 0.1995 | -1.1% | 1.1% |
| 8 | P6 | G11 | 0.21746 | 0.00217 | 0.2132 | 0.2217 | 10.2% | 1.1% |
| 8 | P8 | G13 | 0.24008 | 0.00217 | 0.2358 | 0.2443 | 21.6% | 1.1% |
| 8 | P8 | G1 | 0.20357 | 0.00217 | 0.1993 | 0.2078 | 3.1% | 1.1% |
| 8 | P8 | G10 | 0.19629 | 0.00217 | 0.192 | 0.2006 | -0.6% | 1.1% |

TABLE 6-continued

Effect of Various Promoter::Gene combinations on Culture Biomass

| Number of replicates | Promoter Short Name | Gene Short name | Mean Saturation Biomass value OD600 | Std Error | Lower 95% | Upper 95% | percent performance change from parent | sigma |
|---|---|---|---|---|---|---|---|---|
| 91 | WT | reference control | 0.23611 | 0.00064 | 0.2348 | 0.2374 | | |
| 48 | Control | Promoter Parent Strain | 0.19739 | 0.00089 | 0.1957 | 0.1991 | | |
| 8 | P8 | G9 | 0.19315 | 0.00217 | 0.1889 | 0.1974 | −2.1% | 1.1% |
| 5 | P8 | G11 | 0.19225 | 0.00274 | 0.1869 | 0.1976 | −2.6% | 1.4% |
| 8 | P8 | G6 | 0.23994 | 0.00217 | 0.2357 | 0.2442 | 21.6% | 1.1% |

Example 3—Effect of Promoter Perturbation on Product Titer (Yield)

Genetically engineered cultures with the various promoter::gene combinations from Example 2 were propagated in small-scale cultures designed to assess product titer performance. Small-scale cultures were conducted using media reflective of media from industrial scale cultures. Product titer was optically measured at carbon exhaustion (i.e., yield) with a standard colorimetric assay. Cultures were grown until no further changes in product culture could be measured. Data from this small-scale test is summarized in Table 7 below. Promoter::Gene combinations exhibiting the best improvements in yield are highlighted. A visual representation of the results from this experiment is provided in FIGS. 3A and 3B.

Start coding swapping and promoter swapping can affect multiple phenotypes: Pcg3381 (P6, SEQ ID NO:6) linked to cshA (G3, SEQ ID NO: 11) improves product yield whereas Pcg3381 (P6, SEQ ID NO: 6) linked to eno (G5, SEQ ID NO: 13) improves saturation biomass.

The results also show that the same RNA degradation gene target can positively affect different phenotypes depending on how it's targeted, Pcg1860 (P3, SEQ ID NO: 3) linked to cshA (G3, SEQ ID NO: 11) improves saturation biomass, whereas Pcg3381 (P6, SEQ ID NO: 6) linked to cshA (G3, SEQ ID NO: 11) improves product yield.

TABLE 7

Effect of Various Promoter::Gene combinations on Product Yield

| Number of replicates | Promoter Short Name | Gene Short Name | Mean titer performance value | Std Error | Lower 95% | Upper 95% | percent performance change from parent | sigma |
|---|---|---|---|---|---|---|---|---|
| 96 | WT | reference control | 1.02651 | 0.00198 | 1.0226 | 1.0304 | | |
| 40 | WT | Promoter Parent Strain | 0.95429 | 0.00307 | 0.9483 | 0.9603 | | |
| 8 | P1 | G12 | 0.94201 | 0.00687 | 0.9285 | 0.9555 | −1.3% | 0.7% |
| 4 | P1 | G7 | 0.9615 | 0.00972 | 0.9424 | 0.9806 | 0.8% | 1.0% |
| 8 | P1 | G10 | 0.9302 | 0.00687 | 0.9167 | 0.9437 | −2.5% | 0.7% |
| 4 | P1 | G2 | 0.95563 | 0.00972 | 0.9365 | 0.9747 | 0.1% | 1.0% |
| 4 | P1 | G11 | 0.97209 | 0.00972 | 0.953 | 0.9912 | 1.9% | 1.0% |
| 8 | P1 | G6 | 0.92957 | 0.00687 | 0.9161 | 0.9431 | −2.6% | 0.7% |
| 8 | P2 | G5 | 0.94668 | 0.00687 | 0.9332 | 0.9602 | −0.8% | 0.7% |
| 4 | P2 | G4 | 0.97126 | 0.00972 | 0.9522 | 0.9904 | 1.8% | 1.0% |
| 8 | P2 | G10 | 0.9347 | 0.00687 | 0.9212 | 0.9482 | −2.1% | 0.7% |
| 8 | P2 | G9 | 0.97912 | 0.00687 | 0.9656 | 0.9926 | 2.6% | 0.7% |
| 4 | P2 | G2 | 0.95691 | 0.00972 | 0.9378 | 0.976 | 0.3% | 1.0% |
| 8 | P2 | G11 | 0.95053 | 0.00687 | 0.937 | 0.964 | −0.4% | 0.7% |
| 8 | P3 | G3 | 0.87718 | 0.00687 | 0.8637 | 0.8907 | −8.1% | 0.7% |
| 8 | P3 | G1 | 0.95909 | 0.00687 | 0.9456 | 0.9726 | 0.5% | 0.7% |
| 8 | P3 | G9 | 0.98443 | 0.00687 | 0.9709 | 0.9979 | 3.2% | 0.7% |
| 8 | P3 | G11 | 0.96568 | 0.00687 | 0.9522 | 0.9792 | 1.2% | 0.7% |
| 8 | P3 | G6 | 0.93892 | 0.00687 | 0.9254 | 0.9524 | −1.6% | 0.7% |
| 8 | P5 | G12 | 0.96723 | 0.00687 | 0.9537 | 0.9807 | 1.4% | 0.7% |
| 6 | P5 | G7 | 0.93788 | 0.00793 | 0.9223 | 0.9535 | −1.7% | 0.8% |
| 8 | P5 | G5 | 0.91367 | 0.00687 | 0.9002 | 0.9272 | −4.3% | 0.7% |
| 4 | P5 | G4 | 0.92425 | 0.00972 | 0.9051 | 0.9434 | −3.1% | 1.0% |
| 8 | P5 | G10 | 0.96478 | 0.00687 | 0.9513 | 0.9783 | 1.1% | 0.7% |
| 8 | P5 | G9 | 0.94909 | 0.00687 | 0.9356 | 0.9626 | −0.5% | 0.7% |
| 3 | P5 | G2 | 0.95719 | 0.01122 | 0.9351 | 0.9793 | 0.3% | 1.2% |
| 8 | P5 | G6 | 0.96477 | 0.00687 | 0.9513 | 0.9783 | 1.1% | 0.7% |
| 4 | P6 | G12 | 0.97625 | 0.00972 | 0.9571 | 0.9954 | 2.3% | 1.0% |
| 4 | P6 | G3 | 1.01238 | 0.00972 | 0.9933 | 1.0315 | 6.1% | 1.0% |
| 4 | P6 | G5 | 0.89369 | 0.00972 | 0.8746 | 0.9128 | −6.4% | 1.0% |
| 8 | P6 | G2 | 0.96711 | 0.00687 | 0.9536 | 0.9806 | 1.3% | 0.7% |
| 8 | P6 | G11 | 0.9461 | 0.00687 | 0.9326 | 0.9596 | −0.9% | 0.7% |
| 8 | P8 | G13 | 0.93432 | 0.00687 | 0.9208 | 0.9478 | −2.1% | 0.7% |
| 4 | P8 | G1 | 0.9909 | 0.00972 | 0.9718 | 1.01 | 3.8% | 1.0% |
| 8 | P8 | G10 | 0.9453 | 0.00687 | 0.9318 | 0.9588 | −0.9% | 0.7% |
| 8 | P8 | G9 | 0.95958 | 0.00687 | 0.9461 | 0.9731 | 0.6% | 0.7% |
| 6 | P8 | G11 | 0.965 | 0.00793 | 0.9494 | 0.9806 | 1.1% | 0.8% |
| 8 | P8 | G6 | 0.90574 | 0.00687 | 0.8922 | 0.9193 | −5.1% | 0.7% |

Example 4—Effect of Mutations on Saturation Biomass and Product Titer (Yield)

The product titer and saturation biomass effects of start codon replacements on selected RNA degradation genes of the present disclosure were tested. The plasmids used to genetically engineer the *C. glutamicum* genome were generated using yeast homologous recombination and were then propagated in *E. coli*. Each plasmid was built from a common backbone into which ~2 kb homologous regions were inserted that flank the location of the genomic edit. These homologous regions were PCR amplified from *C. glutamicum* genomic DNA. In between these 2 kb homologous regions, the new start codon was encoded in the 5' end of the primer used to PCR the homologous region.

Plasmids were sequenced to confirm successful cloning, and were then electroporated into *C. glutamicum*. After selection for genomic integration, plasmid backbone DNA was removed using the loopout counter selection methods of the present disclosure. Correctly engineered *C. glutamicum* strains were confirmed by PCR and sequencing. In this case, all start codons were changed to TTG, though other changes to any start codons selected from the group consisting of ATG, GTG, and TTG, are within the scope of this invention.

Figure 4:
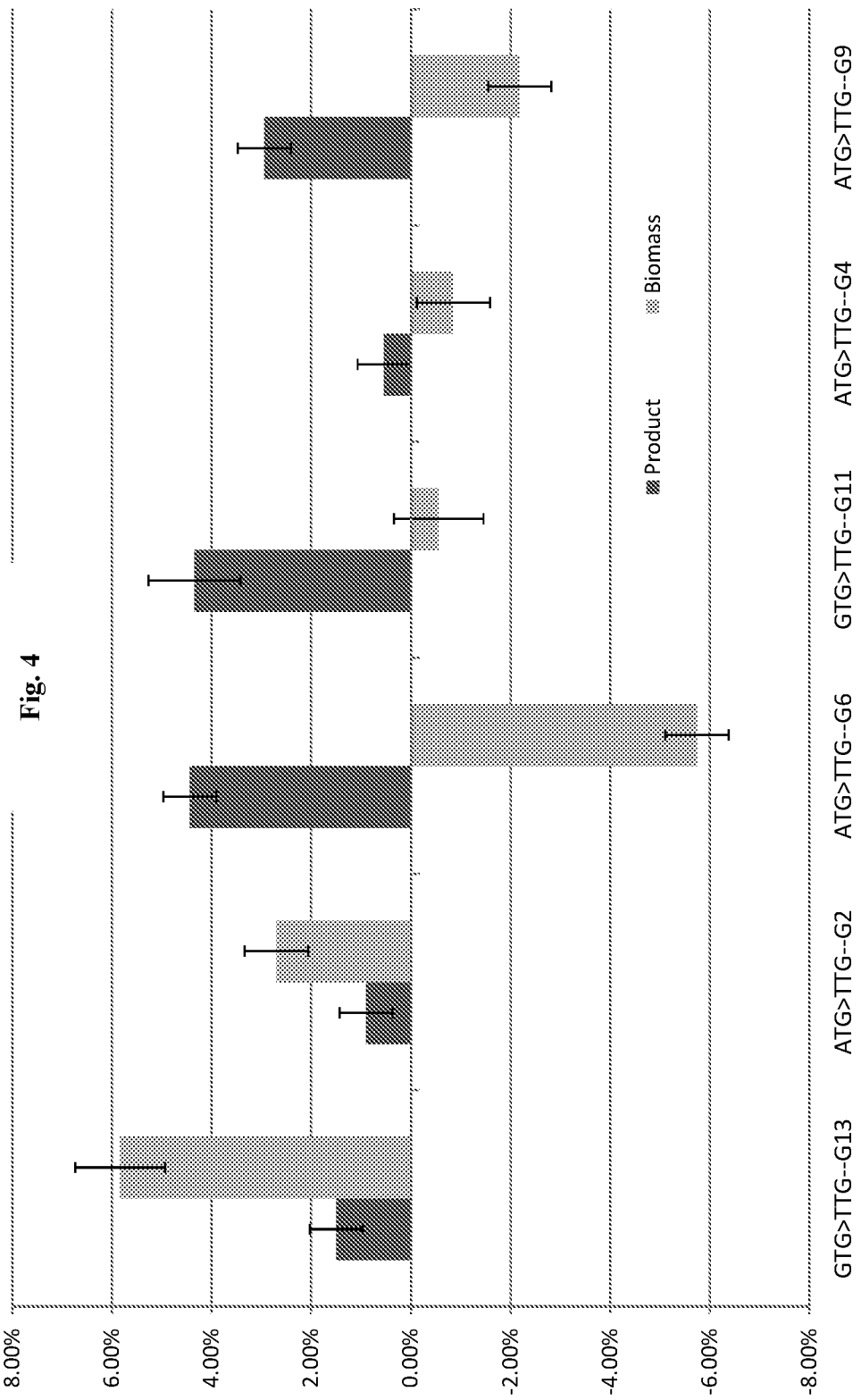
FIG. 4 depicts the results of several RNA degradation gene perturbation experiments, according to the methods of the present disclosure. The performance of genetically engineered treatment host cells comprising a mutated start codon on a selected RNA degradation enzyme was determined. Bars on the graph represent a percent change in saturation biomass or product yield of the genetically engineered host cells over a control culture. Control cultures were genetically identical to the genetically modified cultures, except for lacking the mutated start codon of the present disclosure. Error bars represent two standard deviations.

Genetically engineered cultures with the various start codon replacements were propagated in small scale cultures designed to assess product performance and biomass of the culture. Culture conditions and biomass and titer measurements were conducted as described in Examples 2 and 3. Measurements of product titer at carbon exhaustion therefore represented product yield values for the host cell culture. Cultures were grown until no further changes in product culture could be measured. Biomass cultures were grown for 96 hrs. Data from this small-scale test is included in Tables 8 and 9 below. Start Codon replacements exhibiting the best improvements in product yield and saturation biomass are highlighted. A visual representation of the results from this experiment is also provided in FIG. 4.

Interestingly, promoter replacement of the gpsI gene increases saturation biomass of genetically engineered cultures, while switching the start codon to a less expressed codon decreases it.

The results further suggest that rhlE (G11, SEQ ID NO: 19) GTG>TTG codon change improves product yield whereas me (G13, SEQ ID NO: 21) GTG>TTG improves saturation biomass.

In some embodiments, a single target perturbation can improve both product yield and saturation biomass, as in the case of me (G13, SEQ ID NO: 21) GTG>TTG.

TABLE 8

Effect of Start Codon Changes on Saturation Biomass

| Number of replicates | Start Codon Change | Gene reference control | Mean saturation biomass value OD600 | Std Error | Lower 95% | Upper 95% | percent performance |  |
|---|---|---|---|---|---|---|---|---|
| 12 | WT | parent for start codon swap | 0.23128 | 0.00122 | 0.2289 | 0.2337 | change from |  |
| 47 | WT | strains | 0.23464 | 0.00062 | 0.2334 | 0.2359 | parent | sigma |
| 4 | GTG > TTG | G13 | 0.24833 | 0.00211 | 0.2442 | 0.2525 | 5.8% | 0.9% |
| 8 | ATG > TTG | G2 | 0.24097 | 0.00149 | 0.238 | 0.2439 | 2.7% | 0.6% |
| 8 | ATG > TTG | G6 | 0.22117 | 0.00149 | 0.2182 | 0.2241 | −5.7% | 0.6% |
| 4 | GTG > TTG | G11 | 0.23333 | 0.00211 | 0.2292 | 0.2375 | −0.6% | 0.9% |
| 6 | ATG > TTG | G4 | 0.23264 | 0.00173 | 0.2292 | 0.236 | −0.9% | 0.7% |
| 8 | ATG > TTG | G9 | 0.22951 | 0.00149 | 0.2266 | 0.2325 | −2.2% | 0.6% |

TABLE 9

Effect of Start Codon Changes on Product Yield

| Number of replicates | Start Codon Change | Gene reference control | Mean titer performance value | Std Error | Lower 95% | Upper 95% | percent performance |  |
|---|---|---|---|---|---|---|---|---|
| 16 | WT | parent for start codon swap | 1.01491 | 0.0047 | 1.0057 | 1.0242 | change from |  |
| 62 | WT | strains | 1.01782 | 0.00239 | 1.0131 | 1.0225 | parent | sigma |
| 12 | GTG > TTG | G13 | 1.03308 | 0.00543 | 1.0224 | 1.0438 | 1.5% | 0.5% |
| 12 | ATG > TTG | G2 | 1.027 | 0.00543 | 1.0163 | 1.0377 | 0.9% | 0.5% |
| 12 | ATG > TTG | G6 | 1.06301 | 0.00543 | 1.0523 | 1.0737 | 4.4% | 0.5% |
| 4 | GTG > TTG | G11 | 1.06204 | 0.0094 | 1.0435 | 1.0805 | 4.3% | 0.9% |
| 12 | ATG > TTG | G4 | 1.02328 | 0.00543 | 1.0126 | 1.034 | 0.5% | 0.5% |
| 12 | ATG > TTG | G9 | 1.0478 | 0.00543 | 1.0371 | 1.0585 | 2.9% | 0.5% |

Example 5—Validation of Additional Promoter::Gene Combinations Improving Product Titer Promoter::gene combinations of the present disclosure were empirically tested to determine their effect on titers of a product of interest.

Targets for perturbation of the *C. glutamicum* RNA degradosome were selected as per Example 2. If available, the entire native promoter sequence was replaced with each of 10 promoters of the present disclosure as outlined in Table 5 above. If no native promoter could be identified, each of 8 promoters in the promoter ladder was inserted directly 5' of the target's start codon.

Plasmids to make these changes in the *C. glutamicum* genome were generated using yeast homologous recombination and were then propagated in E cob. Each plasmid was built from a common backbone into which ~2 kb homologous regions were inserted that flank the location of the genomic edit. These homologous regions were PCR amplified from *C. glutamicum* genomic DNA. In between these 2 kb homologous regions, the new promoter or start codon was encoded in the 5' end of the primer used to PCR the homologous region.

Plasmids were sequence confirmed and then electroporated into *C. glutamicum*. After selection for genomic integration, plasmid backbone DNA was removed using the loopout counter selection methods of the present disclosure. Correctly built *C. glutamicum* strains were confirmed by PCR and sequencing.

Correctly built genetically engineered *C. glutamicum* strains were consolidated and then propagated in small scale cultures designed to assess product titers. The product of interest is generated by methylation of substrate included in the fermentation medium. This methylation reaction is catalyzed by a heterologous S-adenosyl methionine-dependent o-methyltransferase expressed from a replicating plasmid.

Figure 5:
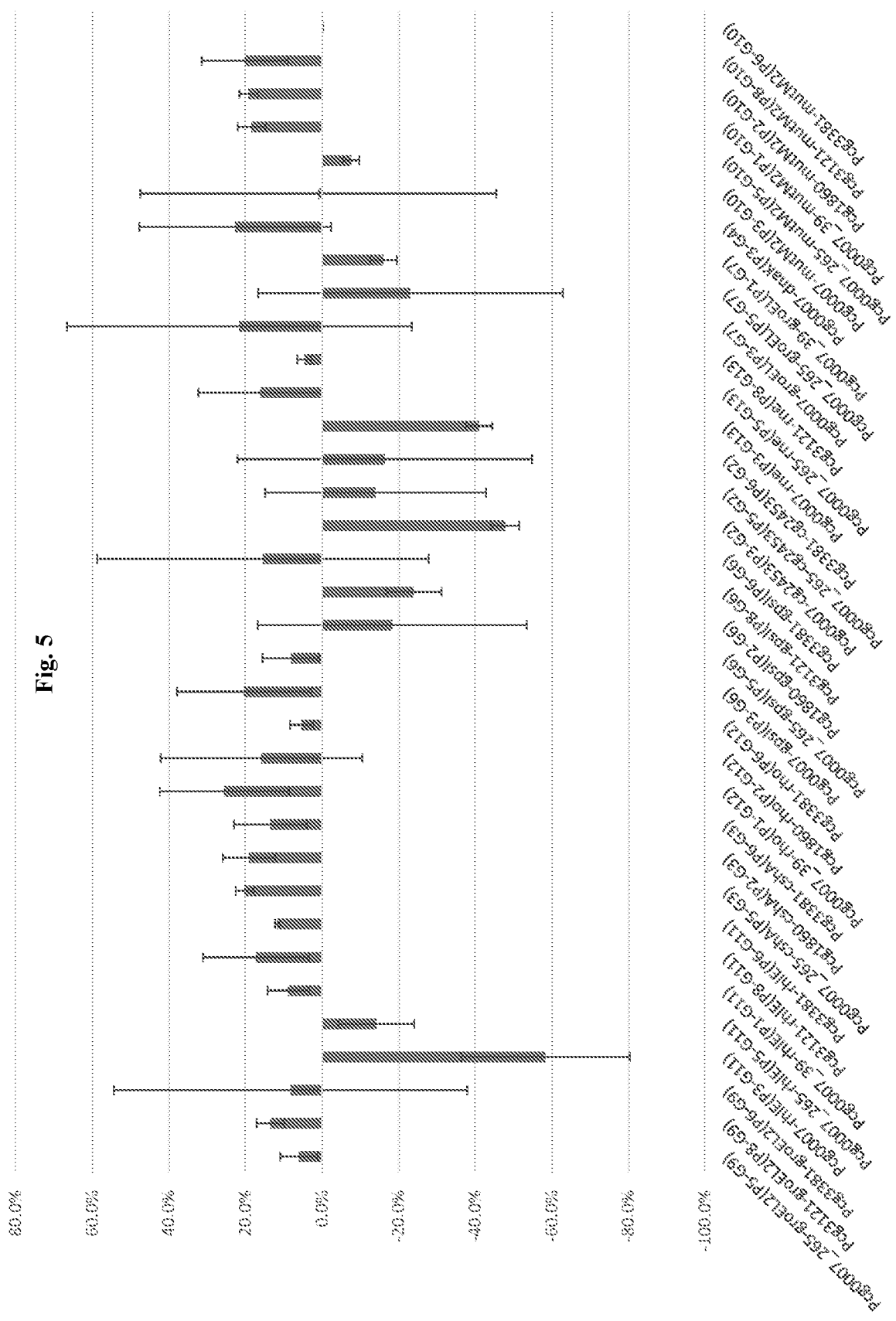
FIG. 5 depicts the product yield results of several RNA degradation gene perturbation experiments, according to the methods of the present disclosure. The performance of genetically engineered treatment host cells comprising a heterologous promoter operably linked to a selected RNA degradation enzyme was determined. Bars on the graph represent a percent change in product yield of the genetically engineered host cells over a control culture. Control cultures were genetically identical to the genetically modified cultures, except for lacking the operably linked heterologous promoters of the present disclosure. Error bars represent two standard deviations.

After a separate biomass propagation step in 96-well microwell plates, cell mass was added to fermentation media containing substrate in 96-well microwell plates and bioconversion was allowed to proceed for 24 hrs. Titers of product were determined for each strain using high-performance liquid chromatography from samples taken at 24 hrs, in order to measure expected yield. Cultures were grown until no further changes in product culture could be measured. Data from this test is included in Table 10 below. Promoter::gene combinations exhibiting the best improvements in product yield are highlighted. A visual representation of the results from this experiment is provided in FIG. 5.

TABLE 10

Effect of various promoter::gene combinations on product yield in small scale

| cultivation Number of replicates | Promoter Short Name | Gene Short name Parent | Mean performance value | Std Error | Lower 95% | Upper 95% | percent performance change from parent | sigma |
|---|---|---|---|---|---|---|---|---|
| 4 | Control | Strain | 347.065 | 37.749 | 272.37 | 421.76 | | |
| 4 | P5 | G9 | 367.928 | 37.749 | 293.23 | 442.63 | 6 | 10 |
| 4 | P8 | G9 | 393.817 | 37.749 | 319.12 | 468.51 | 13 | 10 |
| 4 | P6 | G9 | 375.547 | 37.749 | 300.85 | 450.24 | 8 | 10 |
| 4 | P3 | G11 | 144.664 | 37.749 | 69.97 | 219.36 | −58 | 26 |
| 4 | P5 | G11 | 297.898 | 37.749 | 223.2 | 372.6 | −14 | 13 |
| 4 | P1 | G11 | 377.716 | 37.749 | 303.02 | 452.41 | 9 | 10 |
| 4 | P8 | G11 | 407.026 | 37.749 | 332.33 | 481.72 | 17 | 9 |
| 4 | P6 | G11 | 387.75 | 37.749 | 313.05 | 462.45 | 12 | 10 |
| 4 | P5 | G3 | 417.166 | 37.749 | 342.47 | 491.86 | 20 | 9 |
| 4 | P2 | G3 | 413.269 | 37.749 | 338.57 | 487.97 | 19 | 9 |
| 4 | P6 | G3 | 394.046 | 37.749 | 319.35 | 468.74 | 14 | 10 |
| 4 | P1 | G12 | 435.684 | 37.749 | 360.99 | 510.38 | 26 | 9 |
| 4 | P2 | G12 | 401.982 | 37.749 | 327.28 | 476.68 | 16 | 9 |
| 4 | P6 | G12 | 365.794 | 37.749 | 291.1 | 440.49 | 5 | 10 |
| 4 | P3 | G6 | 417.801 | 37.749 | 343.1 | 492.5 | 20 | 9 |
| 4 | P5 | G6 | 375.335 | 37.749 | 300.64 | 450.03 | 8 | 10 |
| 4 | P2 | G6 | 283.543 | 37.749 | 208.84 | 358.24 | −18 | 13 |
| 4 | P8 | G6 | 264.055 | 37.749 | 189.36 | 338.75 | −24 | 14 |
| 3 | P6 | G6 | 400.818 | 43.588 | 314.56 | 487.07 | 15 | 11 |
| 4 | P3 | G2 | 181.222 | 37.749 | 106.52 | 255.92 | −48 | 21 |
| 4 | P5 | G2 | 298.603 | 37.749 | 223.91 | 373.3 | −14 | 13 |
| 4 | P6 | G2 | 290.191 | 37.749 | 215.49 | 364.89 | −16 | 13 |
| 4 | P3 | G13 | 204.889 | 37.749 | 130.19 | 279.59 | −41 | 18 |
| 4 | P5 | G13 | 403.111 | 37.749 | 328.41 | 477.81 | 16 | 9 |
| 4 | P8 | G13 | 363.237 | 37.749 | 288.54 | 437.94 | 5 | 10 |
| 4 | P3 | G7 | 422.051 | 37.749 | 347.35 | 496.75 | 22 | 9 |
| 4 | P5 | G7 | 267.106 | 37.749 | 192.41 | 341.8 | −23 | 14 |
| 4 | P1 | G7 | 291.39 | 37.749 | 216.69 | 366.09 | −16 | 13 |
| 4 | P3 | G4 | 425.878 | 37.749 | 351.18 | 500.58 | 23 | 9 |
| 4 | P3 | G10 | 350.593 | 37.749 | 275.89 | 425.29 | 1 | 11 |
| 4 | P5 | G10 | 320.718 | 37.749 | 246.02 | 395.42 | −8 | 12 |
| 4 | P1 | G10 | 410.906 | 37.749 | 336.21 | 485.6 | 18 | 9 |
| 4 | P2 | G10 | 413.604 | 37.749 | 338.91 | 488.3 | 19 | 9 |
| 4 | P8 | G10 | 416.955 | 37.749 | 342.26 | 491.65 | 20 | 9 |
| 4 | P6 | G10 | 345.231 | 37.749 | 270.53 | 419.93 | −1 | 11 |

Example 6—Validation of High Throughput Results in Larger Cultures

The beneficial promoter::gene combinations identified by high throughput analysis of Example 5 were evaluated in a larger volume shake flask system. Cell mass was generated by cultivation in 250 mL baffled Erlenmeyer flasks, and transferred to flasks containing fermentation medium and substrate. Bioconversion of substrate to product was allowed to proceed for 24 hrs and product titers evaluated by high-performance liquid chromatography as above. Data from this validation of the host cell strain comprising (P1::G12) is summarized in Table 11.

TABLE 11

Effect of P1::G12 promoter gene combination on product titer in Erlenmeyer flask cultivation

| Number of replicates | Promoter Short Name | Gene Short name | Mean performance value | Lower 95% | Upper 95% | Percent performance change from parent |
|---|---|---|---|---|---|---|
| 4 | Control | Parent Strain | 622.752 | 605.055 | 640.449 | 0 |
| 4 | P1 | G12 | 749.943 | 736.374 | 763.512 | 20 |

Host cell cultures comprising the P1 promoter operably linked to the G12 RNA degradation gene exhibited 20% higher titer at carbon exhaustion, demonstrating significantly higher yields than the control parent host cell cultures lacking the rhoI (G12) promoter modification.

Example 7—Identification of RNA Degradation Gene Homologs in Other Species

The RNA degradation gene sequences from the Corynebacteria disclosed in Table 1 were used to identify homologous gene variants from organisms in the same genus, as well as orthologous genes from other eukaryotic and prokaryotic organisms.

Briefly, amino acid sequences for the RNA degradation genes disclosed in Table 1 were used as search strings in the NCBI BLASTP® database to identify related sequences with high homology to the search gene. Initial searches were conducted with default search parameters in order to identify highly related bacterial homologs for each searched gene. Secondary searches limited to specific *Saccharomyces cerevisiae* were also conducted to identify orthologous sequences in selected genus/species.

The following Table 12 provides the NCBI Reference Sequence Name of the polypeptide sequences of genes identified during this search. Additional homologs and orthologs are identifiable by additional sequence searches based on the RNA degradation gene sequences of the present disclosure.

TABLE 12

RNA Degradation Gene Homologs Identified Through BLASTP® Homology Search Engine

| Gene | Corynebacterium | Saccharomyces cerevisiae |
|---|---|---|
| cg1144 | WP_004568112.1<br>BAB98402.1<br>WP_011897001.1<br>WP_044029870.1<br>WP_003856809.1 | None Identified |
| cg2453 | BAU95388.1<br>WP_053544501.1<br>ANE03625.1<br>WP_011075272.1<br>WP_011014974.1<br>WP_020948617.1<br>WP_011897604.1 | None Identified |
| cshA | CAF20576.1<br>WP_006283992.1<br>WP_040967649.1<br>ANE04470.1<br>BAU96563.1<br>BAB99627.1<br>WP_011014161.1<br>WP_040072671.1<br>WP_060564360.1<br>WP_011265695.1<br>WP_034983681.1<br>WP_063967450.1<br>WP_040967279.1<br>WP_038583556.1<br>WP_003854929.1 | AJU31713.1<br>NP_011932.2<br>GAA23780.1<br>AJU22152.1<br>AJU20676.1<br>CAY80069.1<br>AJU31455.1<br>AJU18404.1<br>AJU16618.1<br>AJU22408.1 |
| dnaK | WP_003862798.1<br>WP_003862798.1<br>WP_003862798.1<br>WP_011015390.1<br>WP_003853569.1<br>BAU97148.1<br>ANE04953.1<br>WP_053545750.1<br>WP_047253930.1 | P0CS91.1<br>NP_012579.1<br>NP_011029.3<br>AJU42857.1<br>NP_009478.1<br>NP_010884.1<br>EDN63079.1<br>AJU50999.1<br>CAY79287.1<br>AJV34706.1 |
| eno | WP_003856756.1<br>WP_053544480.1<br>WP_015650797.1<br>WP_011075256.1<br>WP_018019189.1<br>WP_018119032.1<br>WP_055122813.1<br>WP_055178258.1<br>WP_010187392.1 | AJU27263.1<br>AJR76839.1<br>AJU32945.1<br>AJU25070.1<br>AJR81784.1<br>AJU34506.1<br>AJU33817.1<br>AJP39022.1<br>AHY7959.1<br>AJU19515.1 |
| gpsI | WP_038584450.1<br>WP_040967544.1<br>WP_044030042.1<br>WP_003861678.1<br>WP_003857481.1<br>WP_011014796.1<br>WP_063967578.1 | None Identified |

TABLE 12-continued

RNA Degradation Gene Homologs Identified Through BLASTP ® Homology Search Engine

| Gene | Corynebacterium | Saccharomyces cerevisiae |
|---|---|---|
|  | WP 006284228.1 |  |
|  | WP_011897394.1 |  |
| groEL | WP_038585947.1 | AJV50345.1 |
|  | WP_003862917.1 | AJV51242.1 |
|  | WP_063967760.1 | AJP40402.1 |
|  | WP_040967902.1 | CAY81488.1 |
|  | WP_060565225.1 | AJV60668.1 |
|  | WP_003853751.1 | NP_013360.1 |
|  | BAU97072.1 | EGA73773.1 |
|  | ANE04893.1 | AJV59776.1 |
|  | WP_053545701.1 | AJV70941.1 |
|  | WP_006769076.1 | EGA57589.1 |
| groEL2 | WP_003854561.1 | AJV51242.1 |
|  | WP_011013754.1 | AJP40402.1 |
|  | WP_015439426.1 | AJV50345.1 |
|  | WP_006284375.1 | EGA57589.1 |
|  | WP_011896815.1 | AJV60668.1 |
|  |  | AJV74435.1 |
|  | BAU94999.1 | AJV59776.1 |
|  | WP_053544202.1 | NP_013360.1 |
|  | ANE03290.1 | EGA73773.1 |
|  | WP_015650463.1 | CAY81488.1 |
|  | WP_006769721.1 |  |
| mutM2 | WP_060565392.1 | None Identified |
|  | WP_038586460.1 |  |
|  | WP_011015556.1 |  |
|  | WP_011266054.1 |  |
|  | WP_059290038.1 |  |
|  | WP_003861221.1 |  |
|  | WP_003855116.1 |  |
|  | WP_040073075.1 |  |
|  | WP_006286827.1 |  |
|  | BAU97354.1 |  |
| rhlE | WP_060564204.1 | EGA60267.1 |
|  | WP_003863544.1 | NP_014287.3 |
|  | WP_003858152.1 | AJT17782.1 |
|  | WP_006283683.1 | A6ZRX0.1 |
|  | WP_011013876.1 | AJT33306.1 |
|  | WP_038583081.1 | AJT08370.1 |
|  | BAU95157.1 | KZV08510.1 |
|  | ANE03421.1 | EGA84542.1 |
|  | WP_015650586.1 | AJT14054.1 |
|  | WP_053544338.1 | EWG85578.1 |
| rho | WP_060564388.1 | None Identified |
|  | WP_038583630.1 |  |
|  | WP_011897097.1 |  |
|  | WP_059289111.1 |  |
|  | WP_003854867.1 |  |
|  | WP_031511799.1 |  |
|  | WP_003861319.1 |  |
|  | WP_040967300.1 |  |
|  | WP_063967458.1 |  |
|  | ANE03769.1 |  |
| rne | WP_060564901.1 | None Identified |
|  | WP_038585170.1 |  |
|  | WP_003859300.1 |  |
|  | WP_011897695.1 |  |
|  | WP_034983859.1 |  |
|  | WP_011015068.1 |  |
|  | WP_040072884.1 |  |
|  | WP_004567676.1 |  |
|  | WP_040967734.1 |  |
|  | WP_059289673.1 |  |
| cg2160/RNAse J | WP_011014791.1 | None Identified |
|  | WP_003857476.1 |  |
|  | WP_044030039.1 |  |
|  | WP_040967540.1 |  |
|  | WP_063967576.1 |  |
|  | WP_059289432.1 |  |
|  | WP_011897391.1 |  |
|  | BAU96303.1 |  |
|  | WP_015651527.1 |  |
|  | ANE04245.1 |  |

Further Embodiments of the Invention

Other subject matter contemplated by the present disclosure is set out in the following numbered embodiments:

1. A genetically engineered host cell with enhanced industrial performance, said host cell comprising:
   a. a heterologous promoter polynucleotide, and
   b. a polynucleotide encoding an RNA degradation gene; wherein the heterologous promoter polynucleotide is operably linked to the polynucleotide encoding the RNA degradation gene.
2. The genetically engineered host cell of embodiment 1, wherein the RNA degradation gene is an endogenous gene.
3. The genetically engineered host cell of embodiment 1, wherein the heterologous promoter is a promoter comprising a nucleotide sequence selected from the group consisting of SEQ ID NO: 2, SEQ ID NO: 1, SEQ ID NO: 3, SEQ ID NO: 4, SEQ ID NO: 5, SEQ ID NO: 6, SEQ ID NO: 7, and SEQ ID NO: S.
4. The genetically engineered host cell of embodiment 3, wherein the polynucleotide encoding the RNA degradation gene is a gene comprising a nucleotide sequence selected from the group consisting of SEQ ID NO: 17, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 9, SEQ ID NO: 18, SEQ ID NO: 19, SEQ ID NO: 20, SEQ ID NO: 21, and SEQ ID NO: 22.

4.1 The genetically engineered host cell of embodiment 3, wherein the polynucleotide encoding the RNA degradation gene encodes for an amino acid sequence selected from the group consisting of SEQ ID NO: 42, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 34, SEQ ID NO: 43, SEQ ID NO: 44, SEQ ID NO: 45, SEQ ID NO: 46, and SEQ ID NO: 47.

5. The genetically engineered host cell of embodiment 1, wherein the heterologous promoter is a promoter comprising a nucleotide sequence selected from the group consisting of SEQ ID NO: 2, SEQ ID NO: 1, SEQ ID NO: 5, and SEQ ID NO: 6, and wherein the polynucleotide encoding the RNA degradation gene is SEQ ID NO: 20.

5.1 The genetically engineered host cell of embodiment 1, wherein the heterologous promoter is a promoter comprising a nucleotide sequence selected from the group consisting of SEQ ID NO: 2, SEQ ID NO: 1, SEQ ID NO: 5, and SEQ ID NO: 6, and wherein the polynucleotide encoding the RNA degradation gene encodes for SEQ ID NO: 45.

6. The genetically engineered host cell of embodiment 1, wherein the genetically engineered host cell comprises a combination of the heterologous promoter operably linked to the polynucleotide encoding the RNA degradation gene, said combination selected from the group consisting of: a—(SEQ ID NO: 1::SEQ ID NO: 10), b—(SEQ ID NO: 1::SEQ ID NO: 14), c—(SEQ ID NO: 1::SEQ ID NO: 18), d—(SEQ ID NO: 1::SEQ ID NO: 20), e—(SEQ ID NO: 2::SEQ ID NO: 11), f—(SEQ ID NO: 2::SEQ ID NO: 18), g—(SEQ ID NO: 2::SEQ ID NO: 13), b—(SEQ ID NO: 2::SEQ ID NO: 18), i—(SEQ ID NO: 2::SEQ ID NO: 17), j—(SEQ ID NO: 2::SEQ ID NO: 19), k—(SEQ ID NO: 3::SEQ ID NO: 11), l—(SEQ ID NO: 3::SEQ ID NO: 14), m—(SEQ ID NO: 3::SEQ ID NO: 12), n—(SEQ ID NO: 3::SEQ ID NO: 15), o—(SEQ ID NO: 3::SEQ ID NO: 17), p—(SEQ ID NO: 3::SEQ ID NO: 19), q—(SEQ ID NO: 5::SEQ ID NO: 14), r—(SEQ ID NO: 5::SEQ ID NO: 11)(SEQ ID NO: 6::SEQ ID NO:

13), s—(SEQ ID NO: 6::SEQ ID NO: 19), t—(SEQ ID NO: 8::SEQ ID NO: 21), —(SEQ ID NO: 8::SEQ ID NO: 14), v—(SEQ ID NO: 6::SEQ ID NO: 20), w—(SEQ ID NO: 6::SEQ ID NO: 11), x—(SEQ ID NO: 8::SEQ ID NO: 9), and y—(SEQ ID NO: 8::SEQ ID NO: 18).

6.1 The genetically engineered host cell of embodiment 1, wherein the genetically engineered host cell comprises a combination of the heterologous promoter operably linked to the polynucleotide encoding the RNA degradation gene, said combination selected from the group consisting of: a—(SEQ ID NO: L::a polynucleotide encoding for SEQ ID NO: 35), b—(SEQ ID NO: 1::a polynucleotide encoding for SEQ ID NO: 39), c—(SEQ ID NO: 1::a polynucleotide encoding for SEQ ID NO: 43), d—(SEQ ID NO: 1::a polynucleotide encoding for SEQ ID NO: 45), e—(SEQ ID NO: 2::a polynucleotide encoding for SEQ ID NO: 36), f—(SEQ ID NO: 2::a polynucleotide encoding for SEQ ID NO: 43), g—(SEQ ID NO: 2::a polynucleotide encoding for SEQ ID NO: 38), h—(SEQ ID NO: 2::a polynucleotide encoding for SEQ ID NO: 43), i—(SEQ ID NO: 2::a polynucleotide encoding for SEQ ID NO: 42), j—(SEQ ID NO: 2::a polynucleotide encoding for SEQ ID NO: 44), k—(SEQ ID NO: 3::a polynucleotide encoding for SEQ ID NO: 36), l—(SEQ ID NO: 3::a polynucleotide encoding for SEQ ID NO: 39), m—(SEQ ID NO: 3::a polynucleotide encoding for SEQ ID NO: 37), a—(SEQ ID NO: 3::a polynucleotide encoding for SEQ ID NO: 40), o—(SEQ ID NO: 3::a polynucleotide encoding for SEQ ID NO: 42), p—(SEQ ID NO: 3::a polynucleotide encoding for SEQ ID NO: 44), q—(SEQ ID NO: 5::a polynucleotide encoding for SEQ ID NO: 39), r—(SEQ ID NO: 5::a polynucleotide encoding for SEQ ID NO: 36)(SEQ ID NO: 6::a polynucleotide encoding for SEQ ID NO: 38), s—(SEQ ID NO: 6::a polynucleotide encoding for SEQ ID NO: 44), t—(SEQ ID NO: 8::a polynucleotide encoding for SEQ ID NO: 46), o—(SEQ ID NO: 8::a polynucleotide encoding for SEQ ID NO: 39), v—(SEQ ID NO: 6::a polynucleotide encoding for SEQ ID NO: 45), w—(SEQ ID NO: 6::a polynucleotide encoding for SEQ ID NO: 36), x—(SEQ ID NO: 8::a polynucleotide encoding for SEQ ID NO: 34), and y—(SEQ ID NO: 8::a polynucleotide encoding for SEQ ID NO: 43).

7. The genetically engineered host cell of embodiment 1, wherein the genetically engineered host cell comprises a combination of the heterologous promoter operably linked to the polynucleotide encoding the RNA degradation gene, said combination selected from the group consisting of: a—(SEQ ID NO: 1::SEQ ID NO: 14), b—(SEQ ID NO: 2::SEQ ID NO: 13), c—(SEQ ID NO: 3::SEQ ID NO: 11), d—(SEQ ID NO: 3::SEQ ID NO: 14), e—(SEQ ID NO: 6::SEQ ID NO: 11), and f—(SEQ ID NO: 8::SEQ ID NO:9).

7.1 The genetically engineered host cell of embodiment 1, wherein the genetically engineered host cell comprises a combination of the heterologous promoter operably linked to the polynucleotide encoding the RNA degradation gene, said combination selected from the group consisting of: a—(SEQ ID NO: 1::a polynucleotide encoding for SEQ ID NO: 39), b—(SEQ ID NO: 2::a polynucleotide encoding for SEQ ID NO: 38), c—(SEQ ID NO: 3::a polynucleotide encoding for SEQ ID NO: 36), d—(SEQ ID NO: 3::a polynucleotide encoding for SEQ ID NO: 39), e—(SEQ ID NO: 6::a polynucleotide encoding for SEQ ID NO: 36), and f—(SEQ ID NO: 8::a polynucleotide encoding for SEQ ID NO: 34).

8. The genetically engineered host cell of embodiment 1, wherein the heterologous promoter is a promoter comprising the nucleotide sequence of SEQ ID NO: 1, and wherein the polynucleotide encoding the RNA degradation gene is SEQ ID NO:20.

9. The genetically engineered host cell of embodiment 1, wherein the heterologous promoter is a promoter comprising the nucleotide sequence of SEQ ID NO: 6, and wherein the polynucleotide encoding the RNA degradation gene is SEQ ID NO:20.

9.1 The genetically engineered host cell of embodiment 1, wherein the heterologous promoter is a promoter comprising the nucleotide sequence of SEQ ID NO: 6, and wherein the polynucleotide encoding the RNA degradation gene encodes for SEQ ID NO: 45.

10. The genetically engineered host cell of any one of embodiments 1-9.1, wherein the genetically engineered host cell belongs to the genus *Corynebacterium*.

11. The genetically engineered host cell of any one of embodiments 1-10, wherein the genetically engineered host cell is *Corynebacterium glutamicum*.

12. The genetically engineered host cell of any one of embodiments 1-11, wherein the enhanced industrial performance is saturation biomass, and wherein the genetically engineered host cell exhibits at least about 5% higher saturation biomass than a genetically identical host cell lacking said heterologous promoter polynucleotide, when cultured in identical conditions.

13. The genetically engineered host cell of any one of embodiments 1-11, wherein the enhanced industrial performance is saturation biomass, and wherein the genetically engineered host cell exhibits at least about 10% higher saturation biomass than a genetically identical host cell lacking said heterologous promoter polynucleotide, when cultured in identical conditions.

14. The genetically engineered host cell of any one of embodiments 1-11, wherein the enhanced industrial performance is saturation biomass, and wherein the genetically engineered host cell exhibits at least about 20% higher saturation biomass than a genetically identical host cell lacking said heterologous promoter polynucleotide, when cultured in identical conditions.

15. The genetically engineered host cell of any one of embodiments 1-14, wherein the genetically engineered host cell produces a biomolecule selected from the group consisting of an amino acid, an organic acid, and an alcohol.

16. The genetically engineered host cell of any embodiment 15, wherein the amino acid is tyrosine, phenylalanine, tryptophan, aspartic acid, asparagine, threonine, isoleucine, methionine, or lysine.

17. The genetically engineered host cell of embodiment 15, wherein the organic acid is succinate, lactate or pyruvate.

18. The genetically engineered host cell of embodiment 15, wherein the alcohol is ethanol or isobutanol.

19. The genetically engineered host cell of embodiment 15, wherein the enhanced industrial performance is product yield, and wherein the genetically engineered host cell produces at least about 2% higher yield of the biomolecule than a genetically identical host cell lacking said heterologous promoter polynucleotide, when cultured in identical conditions.

20. The genetically engineered host cell of embodiment 15, wherein the enhanced industrial performance is product yield, and wherein the genetically engineered host cell produces at least about 3% higher yield of the biomolecule than a genetically identical host cell lacking said heterologous promoter polynucleotide, when cultured in identical conditions.

21. The genetically engineered host cell of embodiment 15, wherein the enhanced industrial performance is product yield, and wherein the genetically engineered host cell produces at least about 6% higher yield of the biomolecule than a genetically identical host cell lacking said heterologous promoter polynucleotide, when cultured in identical conditions.

22. A method of producing a biomolecule comprising culturing a host cell of any one of embodiments 1-21 under conditions suitable for producing the biomolecule.

23. A method for generating a host cell capable of increased biomolecule yield, the method comprising:
   a. introducing a heterologous promoter polynucleotide into the genome of the host cell, wherein the heterologous promoter polynucleotide is operably linked to a polynucleotide encoding an RNA degradation gene, thereby creating a genetically engineered host cell;
wherein the genetically engineered host cell produces a higher biomolecule yield compared to the biomolecule yield of a control host cell cultured under identical conditions, wherein the control host cell does not comprise the heterologous promoter polynucleotide.

24. A method for generating a host cell capable of increased saturation biomass, the method comprising:
   a. introducing a heterologous promoter polynucleotide into the genome of the host cell, wherein the heterologous promoter polynucleotide is operably linked to a polynucleotide encoding an RNA degradation gene, thereby creating a genetically engineered host cell;
wherein the genetically engineered host cell exhibits increased saturation biomass compared to the saturation biomass of a control host cell cultured under identical conditions, wherein the control host cell does not comprise the heterologous promoter polynucleotide.

25. The method of any one of embodiments 23-24, wherein the RNA degradation gene is an endogenous gene.

26. The method of any one of embodiments 23-25, wherein the heterologous promoter polynucleotide is selected from the group consisting of SEQ ID NO: 2, SEQ ID NO: 1, SEQ ID NO: 3, SEQ ID NO: 4, SEQ ID NO: 5, SEQ ID NO: 6, SEQ ID NO: 7, and SEQ ID NO: 8.

27. The method of any one of embodiments 23-26, wherein the polynucleotide encoding the RNA degradation gene is selected from the group consisting of SEQ ID NO: 17, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 9, SEQ ID NO: 18, SEQ ID NO: 19, SEQ ID NO: 20, SEQ ID NO: 21, and SEQ ID NO: 22.

27.1 The method of any one of embodiments 23-26, wherein the polynucleotide encoding the RNA degradation gene encodes for an amino acid sequence selected from the group consisting of SEQ ID NO: 42, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 34, SEQ ID NO: 43, SEQ ID NO: 44, SEQ ID NO: 45, SEQ ID NO: 46, and SEQ ID NO:47.

28. The method of any one of embodiments 23-26, wherein the polynucleotide encoding the RNA degradation gene is SEQ ID NO: 20.

28.1 The method of any one of embodiments 23-26, wherein the polynucleotide encoding the RNA degradation gene encodes for SEQ ID NO: 45.

29. The method of any one of embodiments 23 or 25-26, wherein the genetically engineered host cell comprises a combination of the heterologous promoter polynucleotide operably linked to the polynucleotide encoding the RNA degradation gene, said combination selected from the group consisting of: a—(SEQ ID NO: 2::SEQ ID NO: 17), b—(SEQ ID NO: 3::SEQ ID NO: 17), c—(SEQ ID NO: 6::SEQ ID NO: 20), d—(SEQ ID NO: 6::SEQ ID NO: 11), and f—(SEQ ID NO: 8::SEQ ID NO:9).

29.1 The method of any one of embodiments 23 or 25-26, wherein the genetically engineered host cell comprises a combination of the heterologous promoter polynucleotide operably linked to the polynucleotide encoding the RNA degradation gene, said combination selected from the group consisting of: a—(SEQ ID NO: 2::a polynucleotide encoding for SEQ ID NO: 42), b—(SEQ ID NO: 3::a polynucleotide encoding for SEQ ID NO: 42), c—(SEQ ID NO: 6::a polynucleotide encoding for SEQ ID NO: 45), d—(SEQ ID NO: 6::a polynucleotide encoding for SEQ ID NO: 36), and f—(SEQ ID NO: 8::a polynucleotide encoding for SEQ ID NO: 34).

30. The method of any one of embodiments 23 or 25-26, wherein the genetically engineered host cell comprises a combination of the heterologous promoter polynucleotide operably linked to the polynucleotide encoding the RNA degradation gene, said combination selected from the group consisting of: a—(SEQ ID NO: 6::SEQ ID NO: 11), and f—(SEQ ID NO: 8::SEQ ID NO: 9).

30.1 The method of any one of embodiments 23 or 25-26, wherein the genetically engineered host cell comprises a combination of the heterologous promoter polynucleotide operably linked to the polynucleotide encoding the RNA degradation gene, said combination selected from the group consisting of: a—(SEQ ID NO: 6::a polynucleotide encoding for SEQ ID NO: 36), and f—(SEQ ID NO: 8::a polynucleotide encoding for SEQ ID NO: 34).

31. The method of any one of embodiments 23 or 25-26, wherein the heterologous promoter polynucleotide is SEQ ID NO: 6, and wherein the polynucleotide encoding the RNA degradation gene is SEQ ID NO: 20.

31.1 The method of any one of embodiments 23 or 25-26, wherein the heterologous promoter polynucleotide is SEQ ID NO: 6, and wherein the polynucleotide encoding the RNA degradation gene encodes for SEQ ID NO: 45.

32. The method of any one of embodiments 24-26, wherein the genetically engineered host cell comprises a combination of the heterologous promoter polynucleotide operably linked to the polynucleotide encoding the RNA degradation gene, said combination selected from the group consisting of: a—(SEQ ID NO: 1::SEQ ID NO: 10), b—(SEQ ID NO: 1::SEQ ID NO: 14), —(SEQ ID NO: 2::SEQ ID NO: 13), d—(SEQ ID NO: 2::SEQ ID NO: 18), e—(SEQ ID NO: 2::SEQ ID NO: 17), f—(SEQ ID NO: 2::SEQ ID NO: 19), g—(SEQ ID NO: 3::SEQ ID NO: 11), h—(SEQ ID NO: 3::SEQ ID NO: 14), i—(SEQ ID NO: 3::SEQ ID NO: 19), j—(SEQ ID NO: 5::SEQ ID NO: 14), k—(SEQ ID NO: 6::SEQ ID NO: 13), l—(SEQ ID NO: 6::SEQ ID NO: 19), m—(SEQ ID NO: 8::SEQ ID NO: 21), and n—(SEQ ID NO: 8::SEQ ID NO: 14).

32.1 The method of any one of embodiments 24-26, wherein the genetically engineered host cell comprises a combination of the heterologous promoter polynucleotide operably linked to the polynucleotide encoding the RNA degradation gene, said combination selected from the group consisting of a—(SEQ ID NO: 1::a polynucleotide encoding for SEQ ID NO: 35), b—(SEQ ID NO: 1::a polynucleotide encoding for SEQ ID NO: 39), c—(SEQ ID NO: 2::a polynucleotide encoding for SEQ ID NO: 38), d—(SEQ ID NO: 2::a polynucleotide encoding for SEQ ID NO: 43), e—(SEQ ID NO: 2::a polynucleotide encoding for SEQ ID NO: 42), f—(SEQ ID NO: 2::a polynucleotide encoding for SEQ ID NO: 44), g—(SEQ ID NO: 3::a polynucleotide encoding for SEQ ID NO: 36), h—(SEQ ID NO: 3::a polynucleotide encoding for SEQ ID NO: 39), i—(SEQ ID NO: 3::a polynucleotide encoding for SEQ ID NO: 44), j—(SEQ ID NO: 5::a polynucleotide encoding for SEQ ID NO: 39), k—(SEQ ID NO: 6::a polynucleotide encoding for SEQ ID NO: 38), l—(SEQ ID NO: 6::a polynucleotide encoding for SEQ ID NO: 44), m—(SEQ ID NO: 8::a polynucleotide encoding for SEQ ID NO: 46), and a—(SEQ ID NO: 8::a polynucleotide encoding for SEQ ID NO: 39).

33. The method of any one of embodiments 24-26, wherein the genetically engineered host cell comprises a combination of the heterologous promoter polynucleotide operably linked to the polynucleotide encoding the RNA degradation gene, said combination selected from the group consisting of a—(SEQ ID NO: 1::SEQ ID NO: 14), b—(SEQ ID NO: 2::SEQ ID NO: 13), c—(SEQ ID NO: 3::SEQ ID NO: 11), and d—(SEQ ID NO: 3::SEQ ID NO: 14).

33.1 The method of any one of embodiments 24-26, wherein the genetically engineered host cell comprises a combination of the heterologous promoter polynucleotide operably linked to the polynucleotide encoding the RNA degradation gene, said combination selected from the group consisting of: a—(SEQ ID NO: 1::a polynucleotide encoding for SEQ ID NO: 39), b—(SEQ ID NO: 2::a polynucleotide encoding for SEQ ID NO: 38), c—(SEQ ID NO: 3::a polynucleotide encoding for SEQ ID NO: 36), and d—(SEQ ID NO: 3::a polynucleotide encoding for SEQ ID NO: 39).

34. The method of any one of embodiments 24-26, wherein the heterologous promoter polynucleotide is SEQ ID NO: 1, and wherein the polynucleotide encoding the RNA degradation gene is SEQ ID NO: 20.

34.1 The method of any one of embodiments 24-26, wherein the heterologous promoter polynucleotide is SEQ ID NO: 1, and wherein the polynucleotide encoding the RNA degradation gene encodes for SEQ ID NO: 45.

35. The method of any one of embodiments 23-34.1, wherein the genetically engineered host cell belongs to the genus *Corynebacterium*.

36. The method of any one of embodiments 23-35, wherein the genetically engineered host cell is *Corynebacterium glutamicum*.

37. The method of any one of embodiments 23, and 25-31, wherein the biomolecule is selected from the group consisting of an amino acid, an organic acid, and an alcohol.

38. The method of embodiment 37, wherein the amino acid is tyrosine, phenylalanine, tryptophan, aspartic acid, asparagine, threonine, isoleucine, methionine, or lysine.

39. The method of embodiment 37, wherein the organic acid is succinate, lactate or pyruvate.

40. The method of embodiment 37, wherein the alcohol is ethanol or isobutanol.

41. A genetically engineered host cell with enhanced industrial performance, said host cell comprising:
    a. a polynucleotide encoding an RNA degradation gene;
    b. a mutation in the start codon of the polynucleotide of (a);
wherein the mutation results in the replacement of the endogenous start codon of the polynucleotide with a different start codon.

42. The genetically engineered host cell of embodiment 41, wherein the polynucleotide encoding the RNA degradation gene is selected from the group consisting of SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 18, SEQ ID NO: 19, SEQ ID NO: 20, SEQ ID NO: 21, and SEQ ID NO:22.

42.1 The genetically engineered host cell of embodiment 41, wherein the polynucleotide encoding the RNA degradation gene encodes for an amino acid sequence selected from the group consisting of SEQ ID NO: 34, SEQ ID NO: 35, SEQ ID NO: 36, SEQ ID NO: 38, SEQ ID NO: 39, SEQ ID NO: 40, SEQ ID NO: 41, SEQ ID NO: 43, SEQ ID NO: 44, SEQ ID NO: 45, SEQ ID NO: 46, and SEQ ID NO: 47.

43. The genetically engineered host cell of embodiment 41, wherein the polynucleotide encoding the RNA degradation gene is SEQ ID NO: 19.

43.1 The genetically engineered host cell of embodiment 41, wherein the polynucleotide encoding the RNA degradation gene encodes for SEQ ID NO: 44.

44. The genetically engineered host cell of any one of embodiments 41-43.1, wherein the start codon of the endogenous RNA degradation gene is changed from 'ATG' or 'GTG,' to 'TTG'

45. The genetically engineered host cell of any one of embodiments 41-44, wherein the genetically engineered host cell belongs to the genus *Corynebacterium*.

46. The genetically engineered host cell of any one of embodiments 41-45, wherein the genetically engineered host cell is *Corynebacterium glutamicum*.

47. The genetically engineered host cell of any one of embodiments 41-46, wherein the genetically engineered host produces a biomolecule selected from the group consisting of an amino acid, an organic acid, and an alcohol.

48. The genetically engineered host cell of embodiment 47, wherein the amino acid is tyrosine, phenylalanine, tryptophan, aspartic acid, asparagine, threonine, isoleucine, methionine, or lysine.

49. The genetically engineered host cell of embodiment 47, wherein the organic acid is succinate, lactate or pyruvate.

50. The genetically engineered host cell of embodiment 47, wherein the alcohol is ethanol or isobutanol.

51. The genetically engineered host cell of embodiment 47, wherein the genetically engineered host cell produces at least a 2% higher yield of the biomolecule than a genetically identical host cell lacking said heterologous promoter polynucleotide, under identical culture conditions.

52. A method for generating a host cell capable of increased yield of a biomolecule or increased saturation biomass, the method comprising:
    a. genetically modifying the host cell, wherein the modifying comprises mutating the start codon of an endogenous RNA degradation gene, wherein the modification generates a genetically engineered host cell;
wherein the genetically engineered host cell has increased biomolecule yield as compared to the biomolecule yield of a control host cell, or wherein the genetically engineered host cell achieves higher saturation biomass as compared to the saturation biomass of the control host cell, wherein the control host cell does not comprise the start codon mutation of the genetically engineered host cell, and wherein the genetically engineered host cell and the control host cell are cultured under identical conditions.

53. The method of embodiment 52, wherein the endogenous RNA degradation gene is a gene comprising a nucleotide sequence selected from the group consisting of SEQ ID NO: 17, SEQ ID NO: 10, SEQ ID NO: 11, SEQ ID NO:

12, SEQ ID NO: 13, SEQ ID NO: 14, SEQ ID NO: 15, SEQ ID NO: 16, SEQ ID NO: 9, SEQ ID NO: 18, SEQ ID NO: 19, SEQ ID NO: 20, SEQ ID NO: 21, and SEQ ID NO:22.
53.1 The method of embodiment 52, wherein the endogenous RNA degradation gene encodes for an amino acid sequence selected from the group consisting of SEQ ID NO: 42, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 34, SEQ ID NO: 43, SEQ ID NO: 44, SEQ ID NO: 45, SEQ ID NO: 46, and SEQ ID NO: 47.
54. The method of embodiment 52, wherein the RNA degradation gene is a gene comprising the nucleotide sequence of SEQ ID NO: 19. 54.1 The method of embodiment 52, wherein the RNA degradation gene encodes for SEQ ID NO: 44.
55. The method of any one of embodiments 52-54.1, wherein the start codon of the endogenous RNA degradation gene is changed from 'ATG' or 'GTG,' to 'TTG'
56. The method of any one of embodiments 52-55, wherein the genetically engineered host cell belongs to the genus *Corynebacterium*.
57. The method of any one of embodiments 52-56, wherein the genetically engineered host cell is *Corynebacterium glutamicum*.
58. The method of any one of embodiments 52-55, wherein the biomolecule is selected from the group consisting of an amino acid, an organic acid, and an alcohol.
59. The method of embodiment 58, wherein the amino acid is tyrosine, phenylalanine, tryptophan, aspartic acid, asparagine, threonine, isoleucine, methionine, or lysine.
60. The method of embodiment 58, wherein the organic acid is succinate, lactate or pyruvate.
61. The method of embodiment 58, wherein the alcohol is ethanol or isobutanol.
62. The method of embodiment 58, wherein the genetically engineered host cell produces at least a 2% higher yield of the biomolecule than a genetically identical host cell lacking said heterologous promoter polynucleotide, when cultured under identical conditions.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

The invention claimed is:

1. A genetically engineered prokaryotic host cell with enhanced industrial performance, said host cell comprising:
   a. a heterologous promoter polynucleotide, and
   b. a polynucleotide encoding an RNA degradation gene; wherein the heterologous promoter polynucleotide is operably linked to the polynucleotide encoding the RNA degradation gene, wherein the heterologous promoter comprises a promoter from a promoter ladder; wherein the polynucleotide encoding the RNA degradation gene comprises a nucleotide sequence selected from the group consisting of SEQ ID NO: 20, SEQ ID NO: 11, SEQ ID NO: 13, SEQ ID NO: 14, SEQ ID NO: 17, SEQ ID NO: 10, SEQ ID NO: 12, SEQ ID NO: 15, SEQ ID NO: 16, SEQ ID NO: 9, SEQ ID NO: 18, SEQ ID NO: 19, SEQ ID NO: 21, and SEQ ID NO: 22.

2. The genetically engineered host cell of claim 1, wherein the heterologous promoter is a promoter comprising a nucleotide sequence selected from the group consisting of SEQ ID Nos: 1-8.

3. The genetically engineered host cell of claim 1, wherein the heterologous promoter is a promoter comprising a nucleotide sequence selected from the group consisting of SEQ ID NO: 3, SEQ ID NO: 2, SEQ ID NO: 1, SEQ ID NO: 6, and SEQ ID NO: 5, and wherein the polynucleotide encoding the RNA degradation gene encodes for SEQ ID NO: 45.

4. The genetically engineered host cell of claim 3, wherein the heterologous promoter is a promoter comprising the nucleotide sequence of SEQ ID NO: 1.

5. The genetically engineered host cell of claim 3, wherein the heterologous promoter is a promoter comprising the nucleotide sequence of SEQ ID NO: 3.

6. The genetically engineered host cell of claim 1, wherein the heterologous promoter is a promoter comprising a nucleotide sequence selected from the group consisting of SEQ ID NO: 3, SEQ ID NO: 2, SEQ ID NO: 1, SEQ ID NO: 6, and SEQ ID NO: 5, and wherein the polynucleotide encoding the RNA degradation gene comprises SEQ ID NO: 20.

7. The genetically engineered host cell of claim 6, wherein the heterologous promoter is a promoter comprising the nucleotide sequence of SEQ ID NO: 1.

8. The genetically engineered host cell of claim 6, wherein the heterologous promoter is a promoter comprising the nucleotide sequence of SEQ ID NO: 3.

9. The genetically engineered host cell of claim 1, wherein the heterologous promoter is a promoter comprising a nucleotide sequence selected from the group consisting of SEQ ID NO: 3, SEQ ID NO: 6, SEQ ID NO: 5, and SEQ ID NO: 2, and wherein the polynucleotide encoding the RNA degradation gene encodes for SEQ ID NO: 36.

10. The genetically engineered host cell of claim 9, wherein the heterologous promoter is a promoter comprising the nucleotide sequence of SEQ ID NO: 3.

11. The genetically engineered host cell of claim 1, wherein the heterologous promoter is a promoter comprising a nucleotide sequence selected from the group consisting of SEQ ID NO: 3, SEQ ID NO: 6, SEQ ID NO: 5, and SEQ ID NO: 2, and wherein the polynucleotide encoding the RNA degradation gene comprises SEQ ID NO: 11.

12. The genetically engineered host cell of claim 11, wherein the heterologous promoter is a promoter comprising the nucleotide sequence of SEQ ID NO: 3.

13. The genetically engineered host cell of claim 1, wherein the genetically engineered host cell belongs to the genus *Corynebacterium*.

14. The genetically engineered host cell of claim 1, wherein the heterologous promoter is derived from *Corynebacterium glutamicum*, is less than 100 base pairs in length, is able to constitutively express genes across different growth conditions, and is able to co-operate to form a ladder of promoters comprising a plurality of promoters with incrementally increasing levels of promoter activity.

15. A genetically engineered prokaryotic host cell with enhanced industrial performance, said host cell comprising:
   a. a heterologous promoter polynucleotide, and
   b. a polynucleotide encoding an RNA degradation gene; wherein the heterologous promoter polynucleotide is operably linked to the polynucleotide encoding the RNA degradation gene, wherein the heterologous promoter comprises a promoter from a promoter ladder; wherein the heterologous promoter is a promoter comprising a nucleotide sequence selected from the group consisting of SEQ ID Nos: 1-8.

16. The genetically engineered host cell of claim 15, wherein the polynucleotide encoding the RNA degradation gene encodes for an amino acid sequence selected from the group consisting of SEQ ID NO: 45, SEQ ID NO: 36, SEQ ID NO: 38, SEQ ID NO: 39, SEQ ID NO: 42, SEQ ID NO: 35, SEQ ID NO: 37, SEQ ID NO: 40, SEQ ID NO: 41, SEQ ID NO: 34, SEQ ID NO: 43, SEQ ID NO: 44, SEQ ID NO: 46, and SEQ ID NO: 47.

17. The genetically engineered host cell of claim 15, wherein the heterologous promoter is a promoter comprising a nucleotide sequence selected from the group consisting of SEQ ID NO: 3, SEQ ID NO: 2, SEQ ID NO: 1, SEQ ID NO: 6, and SEQ ID NO: 5, and wherein the polynucleotide encoding the RNA degradation gene encodes for SEQ ID NO: 45.

18. The genetically engineered host cell of claim 17, wherein the heterologous promoter is a promoter comprising the nucleotide sequence of SEQ ID NO: 1.

19. The genetically engineered host cell of claim 17, wherein the heterologous promoter is a promoter comprising the nucleotide sequence of SEQ ID NO: 3.

20. The genetically engineered host cell of claim 15, wherein the heterologous promoter is a promoter comprising a nucleotide sequence selected from the group consisting of SEQ ID NO: 3, SEQ ID NO: 2, SEQ ID NO: 1, SEQ ID NO: 6, and SEQ ID NO: 5, and wherein the polynucleotide encoding the RNA degradation gene comprises SEQ ID NO: 20.

21. The genetically engineered host cell of claim 20, wherein the heterologous promoter is a promoter comprising the nucleotide sequence of SEQ ID NO: 1.

22. The genetically engineered host cell of claim 20, wherein the heterologous promoter is a promoter comprising the nucleotide sequence of SEQ ID NO: 3.

23. The genetically engineered host cell of claim 15, wherein the heterologous promoter is a promoter comprising a nucleotide sequence selected from the group consisting of SEQ ID NO: 3, SEQ ID NO: 6, SEQ ID NO: 5, and SEQ ID NO: 2, and wherein the polynucleotide encoding the RNA degradation gene encodes for SEQ ID NO: 36.

24. The genetically engineered host cell of claim 23, wherein the heterologous promoter is a promoter comprising the nucleotide sequence of SEQ ID NO: 3.

25. The genetically engineered host cell of claim 15, wherein the heterologous promoter is a promoter comprising a nucleotide sequence selected from the group consisting of SEQ ID NO: 3, SEQ ID NO: 6, SEQ ID NO: 5, and SEQ ID NO: 2, and wherein the polynucleotide encoding the RNA degradation gene comprises SEQ ID NO: 11.

26. The genetically engineered host cell of claim 25, wherein the heterologous promoter is a promoter comprising the nucleotide sequence of SEQ ID NO: 3.

27. The genetically engineered host cell of claim 15, wherein the genetically engineered host cell belongs to the genus *Corynebacterium*.

28. A genetically engineered prokaryotic host cell with enhanced industrial performance, said host cell comprising:
    a. a heterologous promoter polynucleotide, and
    b. a polynucleotide encoding an RNA degradation gene;
wherein the heterologous promoter is derived from *Corynebacterium glutamicum*, is less than 100 base pairs in length, is able to constitutively express genes across different growth conditions, and is able to co-operate to form a ladder of promoters comprising a plurality of promoters with incrementally increasing levels of promoter activity.

29. The genetically engineered host cell of claim 28, wherein the polynucleotide encoding the RNA degradation gene encodes for an amino acid sequence selected from the group consisting of SEQ ID NO: 45, SEQ ID NO: 36, SEQ ID NO: 38, SEQ ID NO: 39, SEQ ID NO: 42, SEQ ID NO: 35, SEQ ID NO: 37, SEQ ID NO: 40, SEQ ID NO: 41, SEQ ID NO: 34, SEQ ID NO: 43, SEQ ID NO: 44, SEQ ID NO: 46, and SEQ ID NO: 47.

30. The genetically engineered host cell of claim 28, wherein the heterologous promoter is a promoter comprising a nucleotide sequence selected from the group consisting of SEQ ID NO: 3, SEQ ID NO: 2, SEQ ID NO: 1, SEQ ID NO: 6, and SEQ ID NO: 5, and wherein the polynucleotide encoding the RNA degradation gene encodes for SEQ ID NO: 45.

31. The genetically engineered host cell of claim 30, wherein the heterologous promoter is a promoter comprising the nucleotide sequence of SEQ ID NO: 1.

32. The genetically engineered host cell of claim 30, wherein the heterologous promoter is a promoter comprising the nucleotide sequence of SEQ ID NO: 3.

33. The genetically engineered host cell of claim 28, wherein the heterologous promoter is a promoter comprising a nucleotide sequence selected from the group consisting of SEQ ID NO: 3, SEQ ID NO: 2, SEQ ID NO: 1, SEQ ID NO: 6, and SEQ ID NO: 5, and wherein the polynucleotide encoding the RNA degradation gene comprises SEQ ID NO: 20.

34. The genetically engineered host cell of claim 33, wherein the heterologous promoter is a promoter comprising the nucleotide sequence of SEQ ID NO: 1.

35. The genetically engineered host cell of claim 33, wherein the heterologous promoter is a promoter comprising the nucleotide sequence of SEQ ID NO: 3.

36. The genetically engineered host cell of claim 28, wherein the heterologous promoter is a promoter comprising a nucleotide sequence selected from the group consisting of SEQ ID NO: 3, SEQ ID NO: 6, SEQ ID NO: 5, and SEQ ID NO: 2, and wherein the polynucleotide encoding the RNA degradation gene encodes for SEQ ID NO: 36.

37. The genetically engineered host cell of claim 36, wherein the heterologous promoter is a promoter comprising the nucleotide sequence of SEQ ID NO: 3.

38. The genetically engineered host cell of claim 28, wherein the heterologous promoter is a promoter comprising a nucleotide sequence selected from the group consisting of SEQ ID NO: 3, SEQ ID NO: 6, SEQ ID NO: 5, and SEQ ID NO: 2, and wherein the polynucleotide encoding the RNA degradation gene comprises SEQ ID NO: 11.

39. The genetically engineered host cell of claim 38, wherein the heterologous promoter is a promoter comprising the nucleotide sequence of SEQ ID NO: 3.

40. The genetically engineered host cell of claim 28, wherein the genetically engineered host cell belongs to the genus *Corynebacterium*.

* * * * *

SEQUENCE LISTING

```
<160> NUMBER OF SEQ ID NOS: 47

<210> SEQ ID NO 1
<211> LENGTH: 97
<212> TYPE: DNA
<213> ORGANISM: Artificial Sequence
<220> FEATURE:
<223> OTHER INFORMATION: Expression promoter derived from Pcg0007_lib_39

<400> SEQUENCE: 1
tgccgtttct cgcgttgtgt gtggtactac gtggggacct aagcgtgtat tatggaaacg      60
tctgtatcgg ataagtagcg aggagtgttc gttaaaa                               97

<210> SEQ ID NO 2
<211> LENGTH: 97
<212> TYPE: DNA
<213> ORGANISM: Artificial Sequence
<220> FEATURE:
<223> OTHER INFORMATION: Expression promoter derived from Pcg0007

<400> SEQUENCE: 2
tgccgtttct cgcgttgtgt gtggtactac gtggggacct aagcgtgtaa gatggaaacg      60
tctgtatcgg ataagtagcg aggagtgttc gttaaaa                               97

<210> SEQ ID NO 3
<211> LENGTH: 93
<212> TYPE: DNA
<213> ORGANISM: Artificial Sequence
<220> FEATURE:
<223> OTHER INFORMATION: Expression promoter derived from Pcg1860

<400> SEQUENCE: 3
cttagctttg acctgcacaa atagttgcaa attgtcccac atacacataa agtagcttgc      60
gtatttaaaa ttatgaacct aagggggttta gca                                  93
```

```
<210> SEQ ID NO 4
<211> LENGTH: 98
<212> TYPE: DNA
<213> ORGANISM: Artificial Sequence
<220> FEATURE:
<223> OTHER INFORMATION: Expression promoter derived from Pcg0755

<400> SEQUENCE: 4
aataaattta taccacacag tctattgcaa tagaccaagc tgttcagtag ggtgcatggg    60
agaagaattt cctaataaaa actcttaagg acctccaa                           98

<210> SEQ ID NO 5
<211> LENGTH: 97
<212> TYPE: DNA
<213> ORGANISM: Artificial Sequence
<220> FEATURE:
<223> OTHER INFORMATION: Expression promoter derived from Pcg0007_265

<400> SEQUENCE: 5
tgccgtttct cgcgttgtgt gtggtactac gtggggacct aagcgtgtac gctggaaacg    60
tctgtatcgg ataagtagcg aggagtgttc gttaaaa                             97

<210> SEQ ID NO 6
<211> LENGTH: 86
<212> TYPE: DNA
<213> ORGANISM: Artificial Sequence
<220> FEATURE:
<223> OTHER INFORMATION: Expression promoter derived from Pcg3381

<400> SEQUENCE: 6
cgccggataa atgaattgat tattttaggc tcccagggat taagtctagg gtggaatgca    60
gaaatatttc ctacggaagg tccgtt                                         86

<210> SEQ ID NO 7
<211> LENGTH: 97
<212> TYPE: DNA
<213> ORGANISM: Artificial Sequence
<220> FEATURE:
<223> OTHER INFORMATION: Expression promoter derived from Pcg0007_119

<400> SEQUENCE: 7
tgccgtttct cgcgttgtgt gtggtactac gtggggacct aagcgtgttg catggaaacg    60
tctgtatcgg ataagtagcg aggagtgttc gttaaaa                             97

<210> SEQ ID NO 8
<211> LENGTH: 87
<212> TYPE: DNA
<213> ORGANISM: Artificial Sequence
<220> FEATURE:
<223> OTHER INFORMATION: Expression promoter derived from Pcg3121

<400> SEQUENCE: 8
gtggctaaaa cttttggaaa cttaagttac ctttaatcgg aaacttattg aattcgggtg    60
aggcaactgc aactctggac ttaaagc                                        87

<210> SEQ ID NO 9
<211> LENGTH: 1245
<212> TYPE: DNA
<213> ORGANISM: Corynebacterium glutamicum
<220> FEATURE:
<221> NAME/KEY: misc_feature
<222> LOCATION: (1)..(1245)
<223> OTHER INFORMATION: RNA degradation/processing gene cg1144
```

<400> SEQUENCE: 9

```
atggcatttg gattttttag tagacgtaag aaaaagaaca aagacaaaaa cccgaatgaa      60
aattcagcag tgcccgcaca ctctgaagat tcacctcagg aggttttga gggtaatggt      120
cgtcaggtag gcgaccccat tgaacagcag gttgatcgag atgctaaagg tcgtctcaca     180
gcggcggatt tcttgccgga cgctgatctg ccacagctga atcgttcgcg tgcaaatatg     240
ctgcgccgtg aattggagta ccgttttca ctccagaatg cccacattaa tatcgatgga      300
aacacggcca tgattcagcg ttcagatggc ggggcagcac atgtctcgtt gcgcaccctc     360
gcgatgaatg cagctggcct tgataacttt gatcaactcc ctgaactggt ggaaagcttc     420
gttcacggca cgctggccga tgcaacatta aacgatcttt ctactgctga cctgtataaa     480
gcactgcgcc ttcgcctgct gccaacacct ggtgaaggcg acgatctagt tgagcatgga     540
ctcgaccggg aaagccagat ccgcgacgat tcaatcctgc gcaccttcac ctctgacatg     600
tcgatcgcgc tggtgctcga taccgagcat gccatccgca tccagccact caaagagctc     660
gaggagttcg atgacctcag cgccctagag cgggctgcgg accgcaatac ctggcaagag     720
ctttacgacg caaacgttga cgcttccttc gtcgacgctg aatcagacag cgaagggtca     780
tcattttggg ctttcgaatc taactcgtac tacctgggta gtgcaccact gttcctcaac     840
gatttgttgg caaagtgggc acctgacctg gaccaaagtg atggcgtcat ctttgctgtc     900
cctgatcgtg atctgttgat tgcgcgtcct gtgaccaccg cgaagatct gatgaacgga      960
atcaccgcga tggtgaggat cgcgatgcgc tttggcctcg ggaacccgac gtcgataagc     1020
ccgcgcctgc acctgctgcg cgacaaccag gtgaccacct tcaccgactt ccgcgtcgtc     1080
tctcctgaaa tggaagctga atgggaagac agcgcgtttg acgcgccacc ggccggcgcg     1140
atcggcattg aggtgcgccc agatccgtat ctgatggagc cctccaaca gggcggcttt      1200
ggtgatttcg gagatttcgg caagccccgc gatctagata tgtag                     1245
```

<210> SEQ ID NO 10
<211> LENGTH: 1410
<212> TYPE: DNA
<213> ORGANISM: Corynebacterium glutamicum
<220> FEATURE:
<221> NAME/KEY: misc_feature
<222> LOCATION: (1)..(1410)
<223> OTHER INFORMATION: RNA degradation/processing gene cg2453

<400> SEQUENCE: 10

```
atgaagctct atgcagcagt cctcgacttt gaaccagtgg cacaagagtt cggtgtggag      60
cgaggttttg accctcatat ccacgacgaa gccgcgtcaa gtgtcgatag gtatgcgcaa     120
gagcgggaag atctcctgca catgcccttt gtcaccatcg atcccgtagg ttccagagac     180
ctcgatcaag ctgtgctgat tgaggagatc gacagcggat tcgggtgca ttacgcgatt      240
gcagatgtcg cagccttcgt ggagccgggc agtgaattgg aaaagatttc ccttcaccgc     300
gggcagacta tttatctgcc ggattcccca gcgcgactgc accctgagga attatccgaa     360
gatgcggcaa gcctgctgga gggacaaacg agaccagcgg ttgtgtggtc gattgatcta     420
gatgaacgtg gcgaagtcac agccaccaag gtgcgtcgcg ggttggtgaa atcccgggcg     480
cgtttggatt atgatcaggc tcaaatagat gccgagaatg gtcggttgca tccgtcgata     540
agcttattgc ccaaggtcgg gcagctgagg caggaaagcg cgctacgggc gaagccgtg      600
aatctttcta ttcccagcca gcgagtggtg aaagtgccca atgatgacgc cggtgagcac     660
tatgaaattg tcatcgagcc acgcccgcac atcatggatt acaattccga gatttccctg     720
```

| | |
|---|---|
| ctcacaggca tggtagcagg ggagatgatg gtgaaagcgg ggcacggttt gctgcgtaca | 780 |
| ctcgccccgg cgaccaaaga atccgaagct actttcagat cagaggcgca agcccttggt | 840 |
| tttgagatcg cgcccgaaca acccatcggt gagtttcttc aaagtgtgga tcccaatacg | 900 |
| cccaaaggga tggccattca gagggaagcg cagaaactct tgcggggttc tggctacgcc | 960 |
| agcgtgaaaa atggggactc ggaagtgcat tccggtgttg gtggttacta tgctcacgtc | 1020 |
| accgcaccgc tgcgccgact tatcgaccgt ttcgccaccg aacattgtct tgcgattgcc | 1080 |
| tccggaacgg acgttcctga atgggtgacc agggtggaag agcaagttct cgacaccatg | 1140 |
| aaatactcct ccattttggc cagccaagtg gataatgcct gcctcgacct cacagaagcc | 1200 |
| accgtgttga atactggga gggccaaaac ttcaacgcgg tggttgtagc gagcgaacct | 1260 |
| gaaaagaact ctgctcgact ttttgtgtac aaaccgccag tgttggcaaa gtgtattggc | 1320 |
| gccccagaac agggaactaa ccaagaagtc acactggtga ctgcgaactt gaagaagcgt | 1380 |
| gaagttttgt ttgcgtggcc ggctgactaa | 1410 |

<210> SEQ ID NO 11
<211> LENGTH: 2199
<212> TYPE: DNA
<213> ORGANISM: Corynebacterium glutamicum
<220> FEATURE:
<221> NAME/KEY: misc_feature
<222> LOCATION: (1)..(2199)
<223> OTHER INFORMATION: RNA degradation/processing gene cshA

<400> SEQUENCE: 11

| | |
|---|---|
| atgagtaata ccgagaacgt caacggcgac gtagaacagc cgaataacgt catttcgtcg | 60 |
| gaatctcagg aaaccccgca gggtgactca gcatcagctg acttcgctct cgaaaccccca | 120 |
| accaacactg ttgaagatgc accagcatct gagggtagcg aagagatcac cagggttgcg | 180 |
| gatacttctg aggacgccga ctctgcagat gcagacaacg cgagcaatgt aatcaatgag | 240 |
| aatgaggact cctcggaagg tgctaaccag ccttcaaacg agtcatcctc tacggaagcc | 300 |
| aagtccggct tcgatgcact cggactgcca gagcgtgttc ttgacgctgt gcgcaaggtg | 360 |
| ggttacgaaa ctccttcccc aattcaggca caaaccatcc caatcctcat ggagggccag | 420 |
| gatgttgttg gtctagcaca gaccggtacc ggtaagaccg cagctttcgc gctgccaatc | 480 |
| ctttcccgta ttgacaagtc cgtgcgcagc ccacaggcac ttgtgcttgc ccctacccgt | 540 |
| gagctggcac ttcaggttgc tgactccttc aatccttcg ctgaccacgt cggtggcctg | 600 |
| aacgttctgc caatctatgg tggacaggct tacggcattc agctctctgg cctgcgtcgt | 660 |
| ggcgctcaca tcgtcgtggg taccccaggc cgtatcatcg accacctcga aagggctcc | 720 |
| ctggatatct ccggactgcg cttcctcgtg ctcgatgaag cagacgagat gctgaacatg | 780 |
| ggcttccagg aagatgtcga gcgcatcctc gaggacaccc cagacgagaa gcaggttgca | 840 |
| ctattctccg caacgatgcc aaacggcatt cgtcgcctgt ccaagcagta cctgaacaac | 900 |
| cctgctgaaa tcaccgttaa gtccgagacc aggactaaca ccaacatcac ccagcgcttc | 960 |
| ctcaacgttg cacaccgcaa caagatggat gcactgaccc gtattctcga ggtcaccgag | 1020 |
| tttgaagcaa tgatcatgtt cgtgcgcacc aagcacgaaa ctgaagaagt tgctgaaaag | 1080 |
| ctccgtgcac gcggattctc cgcagcagcc atcaacggcg acattgctca ggcacagcgt | 1140 |
| gagcgcaccg tcgaccagct gaaggacggc cgcctagaca tcctcgttgc aaccgacgtt | 1200 |
| gcagcccgtg gtcttgacgt tgagcgcatc tcccacgtgc ttaacttcga cattccaaac | 1260 |
| gacaccgagt cctacgttca ccgcatcggc cgcaccggcc gtgcaggacg taccggcgag | 1320 |

```
gcaatcctgt tcgtgacccc acgtgagcgt cgtatgcttc gctccatcga gcgcgcaacc     1380
aacgcaccac tgcacgaaat ggaactgcca accgtcgatc aggtcaacga cttccgcaag     1440
gtcaagttcg ctgactccat caccaagtcc ctcgaggaca agcagatgga cctgttccgc     1500
accctggtca aggaatactc ccaggccaac gacgttcctt tagaggacat cgcagcggca     1560
ctggcaaccc aggcacagtc cggcgacttc ctgctcaagg agctcccacc agagcgccgc     1620
gagcgcaacg accgccgtcg tgaccgtgac ttcgacgacc gtggtggacg tggacgcgac     1680
cgtgaccgtg gcgaccgcgg agatcgtggc tcacgcttcg accgcgacga cgagaacctg     1740
gcaacctacc gcctcgcagt gggcaagcgc agcacatcc gcccaggcgc aatcgttggt      1800
gcacttgcca acgaaggtgg cctgaactcc aaggacttcg gccgcatcac catcgcagcc     1860
gaccacaccc tggttgaact gccaaaggac ctcccacaga gcgttcttga caacctgcgc     1920
gacacccgca tctccggcca gctcatcaac atcgaacgcg actccggtgg acgcccacca     1980
cgccgcttcg agcgcgatga ccgtggcgga cgcggcggat ccgcggcga ccgtgatgac      2040 cgcggtggac gtggacgcga ccgtgacgat cgtggaagcc gtggaggttt ccgcggtgga    2100
cgtgaccgtg acgatcgtgg cggacgcggt ggattccgtg acgcgacga ccgcggagac     2160 cgtggtggcc gtggcggtta ccgtggcgga cgcgattaa                          2199

<210> SEQ ID NO 12
<211> LENGTH: 1857
<212> TYPE: DNA
<213> ORGANISM: Corynebacterium glutamicum
<220> FEATURE:
<221> NAME/KEY: misc_feature
<222> LOCATION: (1)..(1857)
<223> OTHER INFORMATION: RNA degradation/processing gene dnaK

<400> SEQUENCE: 12
atgggacgtg cagtaggaat tgaccttgga accaccaact ctgtggtttc cgtacttgaa       60
ggcggcgagc cagtagttat cgcaaacgca gaaggctcac gcaccacccc ttccgtcgtt      120
gcattcgcaa agaacggtga agttctagtc ggccagtccg ctaagaacca ggcagtcacc      180
aacgttgacc gcaccattcg ctccgtcaag cgccacatcg caccgactg gtccgttgct       240 atcgatgaca agaactacac ctcacaggaa atctcggctc gtaccctgat gaagctgaag      300
cgcgacgctg aagcatacct gggcgaggac gtcactgatg ctgttattac cgttcctgca      360
tacttcgagg actcacagcg ccaggcaacc aaggaagctg ccagatcgc aggccttaac       420 gttctgcgta ttgttaacga gccaaccgcg gctgcacttg catacggcct tgagaagggc      480
gagcaggagc agaccattct ggtattcgac ctcggtggcg gcaccttcga cgtctccctc      540
ctagagatcg cgacggtgt tgttgaggtt cgcgcaacct ccggcgataa cgagctcggt       600
ggcgacgact gggatcagcg tatcgttgac tggctggtag agaagttcca gtcctccaac      660
ggcatcgacc tgaccaagga caagatggcc ctgcagcgtc tgcgtgaggc agctgagaag      720
gcaaagatcg agctgtcctc ttcccagagt gcaaacatca accttcctta catcaccgtt      780
gatgcagaca agaacccact gttcttggat gagacccttt ccgtgccga gttccagcgc       840 atcacccagg acctcctggc ccgcaccaag actcctttca accaggttgt taaggacgct     900
ggcgtgtccg tctcggagat cgaccacgtt gttctcgtcg gtggttccac ccgtatgcct     960
gctgttaccg aactggtcaa ggaactgacc ggtggacgtg agccaaacaa gggtgttaac    1020
ccagatgagg ttgttgcagt tggtgcagca cttcaggccg tgttctccg cggcgaggtc     1080 aaggatgtgc ttcttcttga cgtcaccccca ctgtccctcg gcattgagac caagggtggc   1140
```

```
gtgatgacca agctcatcga gcgcaacacc accatccctc ccaagcgttc cgagaccttc   1200
accaccgcag aggataacca gccttctgtt cagatccagg tcttccaggg cgagcgtgaa   1260
atcgcaaccg ccaacaagct gctcggatcc ttcgagctcg gcggcatcgc acctgcacca   1320
cgtggcgtcc cacagatcga ggtcactttc gacatcgacg ccaacggcat cgtccacgtc   1380
accgcaaagg acaagggtac tggcaaggaa acaccatca ccattcagga cggctccggt   1440
ctctcccagg atgaaattga tcgcatgatc aaggatgctg aagctcacgc tgatgaggac   1500
aagaagcgcc gcgaggagca ggaagtccgc aacaacgctg agtccctggt ttaccagacc   1560
cgcaagttcg ttgaagagaa ctccgagaag gtctccgaag accttaaggc aaaggtcgaa   1620
gaggcagcca agggcgttga agaagcactc aagggcgagg cctcgaggc aatcaaggct   1680 gcagttgaga agctgaacac cgagtcccag gaaatgggta aggctatcta cgaggctgac   1740
gctgctgctg gtgcaaccca ggctgacgca ggtgcagaag cgctgcaga tgacgatgtt   1800 gttgacgctg aagttgtcga agacgacgca gctgacaatg gtgaggacaa gaagtaa     1857
```

<210> SEQ ID NO 13
<211> LENGTH: 1278
<212> TYPE: DNA
<213> ORGANISM: Corynebacterium glutamicum
<220> FEATURE:
<221> NAME/KEY: misc_feature
<222> LOCATION: (1)..(1278)
<223> OTHER INFORMATION: RNA degradation/processing gene eno

<400> SEQUENCE: 13

```
gtggctgaaa tcatgcacgt attcgctcgc gaaattctcg actcccgcgg taacccaacc     60
gtcgaggcag aggttttcct tgatgacggt tcccacggtg tcgcaggtgt tccatccggc    120
gcatccaccg cgtccacga ggctcatgag ctgcgtgacg tggcgatcg ctacctgggc     180 aagggcgttt tgaaggcagt tgaaaacgtc aacgaagaaa tcggcgacga gctcgctggc    240
ctagaggctg acgatcagcg cctcatcgac gaagcaatga tcaagcttga tggcaccgcc    300
aacaagtccc gcctgggtgc aaacgcaatc cttggtgttt ccatggctgt tgcaaaggct    360
gctgctgatt ccgcaggcct cccactgttc cgctacatcg gtggaccaaa cgcacacgtt    420
cttccagttc aatgatgaa catcatcaac ggtggcgctc acgctgactc cggtgttgac    480
gttcaggaat tcatgatcgc tccaatcggt gcagagacct tctctgaggc tctccgcaac    540
ggcgcagagg tctaccacgc actgaagtcc gtcatcaagg aaaagggcct gtccaccgga    600
cttggcgatg agggcggctt cgctccttcc gtcggctcca cccgtgaggc tcttgacctt    660
atcgttgagg caatcgagaa ggctggcttc accccaggca aggacatcgc tcttgctctg    720
gacgttgctt cctctgagtt cttcaaggac ggcacctacc acttcgaagg tggccagcac    780
tccgcagctg agatggcaaa cgtttacgct gagctcgttg acgcgtaccc aatcgtctcc    840
atcgaggacc cactgcagga agatgactgg gagggttaca ccaacctcac cgcaaccatc    900
ggcgacaagg ttcagatcgt tggcgacgac ttcttcgtca ccaaccctga gcgcctgaag    960
gagggcatcg ctaagaaggc tgccaactcc atcctggtta aggtgaacca gatcggtacc   1020
ctcaccgaga ccttcgacgc tgtcgacatg gctcaccgcg caggctacac ctccatgatg   1080
tcccaccgtt ccggtgagac cgaggacacc accattgctg acctcgcagt tgcactcaac   1140
tgtggccaga tcaagactgg tgctccagca cgttccgacc gtgtcgcaaa gtacaaccag   1200
cttctccgca tcgagcagtt gcttggcgac gccggcgtct acgcaggtcg cagcgcattc   1260
ccacgctttc agggctaa                                                 1278
```

<210> SEQ ID NO 14
<211> LENGTH: 2262
<212> TYPE: DNA
<213> ORGANISM: Corynebacterium glutamicum
<220> FEATURE:
<221> NAME/KEY: misc_feature
<222> LOCATION: (1)..(2262)
<223> OTHER INFORMATION: RNA degradation/processing gene gpsI

<400> SEQUENCE: 14

```
atgagcgatg taaagtactt cgaagacacc gaatttggcc tgatcgaggc cgtcgcaacc      60
atcgacaacg gtgacttcgg aacccgcacc atccgttttg aaaccggcca acttgcccgc     120
caggcagatg gtgcagtgac cacctatctc gacgatgaca cgatgctgct ggcaaccacc     180
accgcatcca accagccacg cgagggcttt gacttcttcc cactgaccgt ggacgttgaa     240
gagcgtatgt acgcagctgg tcgcatccct ggctctttct ccgtcgtga gggccgccca     300 tccaccgaag ctatcctggc ttgccgtctc atcgaccgcc cactgcgccc aacctttgtt     360
aagggcctgc gcaatgaggt tcagatcgtt gtcaccgtca tgtccatgaa ccctgaggat     420
tactacgatg tcgtagcaat caacggagct tccgcagcaa cccgcatctc cggacttcct     480
gtctccggcg ctgtcggtgg cgttcgcatg gcactggttg ttgatgaaaa gcacccagaa     540
ggccaatggg ttgcattccc aacccacgct caacatgagc agtccgtatt tgaaatcgtt     600
gtggctggtc gcctcgtcga gcgcaagcgc ggcaacaaga ccttctccga cgtcgcagtg     660
atgatggtgg aagctggcgc ttccgaaaac gttgtcaacc gcgtcaagga cggtgcacca     720
gcaccaaccg aaaagatcgt ctccgacggc cttgaagcag ctaagccatt catcgacatc     780
ctgtgccgcg cacaggaagg tctggcacag cgcgttggaa acgcagccaa ggaattccca     840
ctgttccctc catacaccga cgaggtgtac tccgcagtgg agcgcaaggt atccaagaag     900
ctagcttctt tgctgaccct gaaggcaaag caagagcgcg acgacgctac caacgcctac     960
atggaagaaa tcgaagccga actgcttcca aagttcgagg cttcctacag ctcagcagcg    1020
gaagcgtcca aggaaatccg tgcagcatac aacgctgtca tgaaggccat cgtgcgccgc    1080
atgatcctca ccgatcactt ccgcatcgac ggccgcggag tcaccgacat ccgtgacctg    1140
gcagtagaag ttgagctcat cccacgtgcg cacggttcct ccctcttcga gcgtggcgag    1200
acccagatcc tcggtgtcac caccctggac atgctcaaga tggaacagca atcgactcc    1260 ctggcaccag gcgatgcgaa gcgctacatg caccactaca acttccctcc atactccacc    1320
ggtgaaaccg tcgtgtgggg ctcaccaaag cgccgcgaaa tcggccacgg tgcacttgca    1380
gaacgcgcag ttttgccagt aatcccatcc cgtgaggaat cccatacgc aatccgtcag    1440 gtctctgaag ctctgggctc caacggctcc acctccatgg gctctgtctg tgcatccact    1500
ctgtccctgt acaacgctgg tgttccactg aaggcacctg ttgcaggtat cgccatggga    1560 cttgttccg gtgaaatcga cggcaagacc gagtacgttg cactgaccga catcctcggc    1620
gcagaagacg cattcggcga catggacttc aaggttgccg gcaccgcaga cttcatcacc    1680
gcacttcagc tggacaccaa gctggacggc attccttcca aggtgctctc cgatgcgctt    1740
gagcaggcac gcgatgcccg actgaccatc ctgaacacca tggctgatgt catcaacgga    1800
gctgatgaga tgagcaagtt cgctcctcgc atcaccaccg tgaagatccc agtggcaaag    1860
atcggtgagc tgatcggacc aaagggtaag aacatcaacg ctcttaccga agagaccggc    1920
gcaaacatct ccatcgaaga tgacggcacc gtgttcatct ctgcagctga cggcgcatct    1980
gctgaagcgg cgatcgaaaa gatcaacgct ctggcgaacc cacagctgcc aaaggttggc    2040
```

```
gagcgcttcc tcggaaccgt cgtcaagacc accgcattcg gagcattcgt ttccttgctc    2100
ccaggccgcg acggccttgt tcacatctcc aagctgggta acggcaagcg agtagaaaag    2160
gtcgacgatg tggtgaaggt tggcgagaag attcaggtcg aaatcgctga catcgacaac    2220
cgcggcaaga tctccttggt cccagttgtt gaagaggact aa                       2262

<210> SEQ ID NO 15
<211> LENGTH: 1647
<212> TYPE: DNA
<213> ORGANISM: Corynebacterium glutamicum
<220> FEATURE:
<221> NAME/KEY: misc_feature
<222> LOCATION: (1)..(1647)
<223> OTHER INFORMATION: RNA degradation/processing gene groEL

<400> SEQUENCE: 15
atggcaaaga tcatcgcctt tgatgaggaa gcacgtcgtg cctagaaaa gggactgaac       60 accctggctg acgctgttaa ggttactttg ggaccaaagg ccgtaacgt cgttttggaa      120 aaggcttggg gcgccccaac cattaccaac gatggtgtca ccatcgcacg tgagatcgag     180
cttgaggatc cttacgagaa gatcggcgca gagctggtca aggaagttgc taagaagact     240
gatgacgtcg cgggcgatgg caccaccacc gctaccgtat tggcacaggc tctggttaag    300
gaaggcctgc gcaacgttgc tgctggttcc aacccaatgg gcatcaagcg tggcatcgag    360
aaggctgttg ctcaggtaac tgagaagctg ctcgaagctg cgaaggaagt tgagaccgag    420
gagcagatcg ctgctaccgc tggtatctcc gcagctgacc cagctatcgg cgcacagatt    480
gctaaggcaa tgtacgcagt tggcggtggc aagctgaaca aggattccgt catcactgtt    540
gaagagtcca acactttcgg tgttgagctc gaggttactg agggtatgcg ctttgataag    600
ggctacatct ccggttactt cgcaactgac atggagcgcc tcgaggctgt tctggaagat    660
ccttacatcc tgctggtttc cggcaagatc tccaacatca aggacctgct cccactgctg    720
gagaaggtca tgcagtccgg caagcctttg ctgatcatct ctgaggacgt cgagggcgag    780
gctctgtcca ccctggttgt caacaagatc cgtggcacct tcaagtctgt tgctgttaag    840
gctccaggct tcggcgaccg ccgtaaggct cagctgcagg acattgctgt tctgaccggt    900
ggccaggtca tttctgaaga ggttggcctc tccctcgaga ccgctgatct gccacttcta    960
ggccaggcac gcaaggttgt tgtcaccaag gatgacacca ctatcgttga tggcgcaggt   1020
tctgaggctc agatcgaggg tcgcgttaac cagatccgcg ttgagatcga gaactctgat   1080
tccgattacg accgtgagaa gctcaacgag cgcctggcta agcttgccgg cggcgttgca   1140
gttcttaagg ttggcgctgc aactgaggtt gagctcaagg agcgcaagca ccgcattgag   1200
gacgcagtcc gcaacgctaa ggcagctgtt gaagagggca tcgttgcagg cggtggcgtt   1260
gcgctgctgc aggctgctca cgtcctggac aacgatcttg agctttccgg cgacgaggca   1320
accggcgttc gcatcgtccg cgaggctctg actgctcctc tgaagcagat cgctgctaac   1380
gctggcctcg agccaggcgt tgttgctgac aaggtttccc agctcccaca gggcgagggc   1440
ctcaacgctg caaacggcga gtacgtcgac ctcatggctg cgggcatcaa cgacccagtt   1500
aaggtcaccc gctccgcact ccagaacgct gcatccattg cagctctgtt cctgaccact   1560
gaggctgtcg ttgctgacaa gccacagcct gcaggcgcag ctggcatgcc aggtgcagac   1620
gagatgggcg gcatgggcgg cttctaa                                       1647
```

<210> SEQ ID NO 16
<211> LENGTH: 1647
<212> TYPE: DNA
<213> ORGANISM: Corynebacterium glutamicum
<220> FEATURE:
<221> NAME/KEY: misc_feature
<222> LOCATION: (1)..(1647)
<223> OTHER INFORMATION: RNA degradation/processing gene groEL genbank
      CP012194 homolog

<400> SEQUENCE: 16

```
atggcaaaga tcatcgcctt tgatgaggaa gcacgtcgtg gcctagaaaa gggactgaac      60
accctgactg acgctgttaa ggttactttg ggaccaaagg ccgtaacgt cgttttggaa     120
aaggcttggg gcgccccaac cattaccaac gatggtgtca ccatcgcacg tgagatcgag     180
cttgaggatc cttacgagaa gatcggcgca gagctggtca aggaagttgc taagaagact     240
gatgacgtcg cgggcgatgg caccaccacc gctaccgtat tggcacaggc tctggttaag     300
gaaggcctgc gcaacgttgc tgctggttcc aacccaatgg gcatcaagcg tggcatcgag     360
aaggctgttg ctcaggtaac tgagaagctg ctcgaagctg cgaaggaagt tgagaccgag     420
gagcagatcg ctgctaccgc tggtatctcc gcagctgacc cagctatcgg cgcacagatt     480
gctaaggcaa tgtacgcagt tggcggtggc aagctgaaca aggattccgt catcactgtt     540
gaagagtcca acactttcgg tgttgagctc gaggttactg agggtatgcg ctttgataag     600
ggctacatct ccggttactt cgcaactgac atggagcgcc tcgaggctgt tctggaagat     660
ccttacatcc tgctggtttc cggcaagatc tccaacatca aggacctgct cccactgctg     720
gagaaggtca tgcagtccgg caagcctttg ctgatcatct ctgaggacgt cgagggcgag     780
gctctgtcca ccctggttgt caacaagatc cgtggcacct tcaagtctgt tgctgttaag     840
gctccaggct tcggcgaccg ccgtaaggct cagctgcaga acattgctgt tctgaccggt     900
ggccaggtca tttctgaaga ggttggcctc tccctcgaga ccgctgatct gccacttcta     960
ggccaggcac gcaaggttgt tgtcaccaag gatgacacca ctatcgttga tggcgcaggt    1020
tctgaggctc agatcgaggg tcgcgttaac cagatccgcg ttgagatcga gaactctgat    1080
tccgattacg accgtgagaa gctcaacgag cgcctggcta agcttgccgg cggcgttgca    1140
gttcttaagg ttggcgctgc aactgaggtt gagctcaagg agcgcaagca ccgcattgag    1200
gacgcagtcc gcaacgctaa ggcagctgtt gaagagggca tcgttgcagg cggtggcgtt    1260
gcgctgctgc aggctgctca cgtcctggac aacgatcttg agctttccgg cgacgaggca    1320
accggcgttc gcatcgtccg cgaggctctg actgctcctc tgaagcagat cgctgctaac    1380
gctggcctcg agccaggcgt tgttgctgac aaggtttccc agctcccaca gggcgagggc    1440
ctcaacgctg caaacggcga gtacgtcgac ctcatggctg cgggcatcaa cgacccagtt    1500
aaggtcaccc gctccgcact ccagaacgct gcatccattg cagctctgtt cctgaccact    1560
gaggctgtcg ttgctgacaa gccacagcct gcaggcgcag ctggcatgcc aggtgcagac    1620
gagatgggcg gcatgggcgg cttctaa                                        1647
```

<210> SEQ ID NO 17
<211> LENGTH: 1617
<212> TYPE: DNA
<213> ORGANISM: Corynebacterium glutamicum
<220> FEATURE:
<221> NAME/KEY: misc_feature
<222> LOCATION: (1)..(1617)
<223> OTHER INFORMATION: RNA degradation/processing gene groEL2

<400> SEQUENCE: 17

```
atggcaaagc tcattgcttt tgaccaggac gcccgcgaag gcattctccg gggcgttgac      60
gctctggcaa acgctgtcaa ggtaaccctc ggcccacgcg gccgtaacgt ggttcttgat     120
aaggcattcg gcggacctct ggtcaccaac gacggtgtca ccattgcccg cgacatcgac     180
cttgaggatc cttttgagaa cctcggtgca cagctggtga agtccgttgc tgttaagacc     240
aacgatatcg ctggcgacgg caccaccacc gcaactctgc ttgctcaggc actcattgct     300
gaaggcctac gcaacgttgc tgctggcgca aacccaatgg agctcaacaa gggtattgct     360
gcagctgcag aaaagaccct ggaagagctg aaggcacgcg caaccgaggt gtctgacacc     420
aaggaaatcg caaacgtcgc aaccgtttca tcccgcgatg aagttgtcgg cgaaattgtt     480
gctgcagcaa tggagaaggt tggcaaagac ggtgtcgtca ccgtcgagga gtcccagtcc     540
atcgagactg ctctcgaggt caccgaaggt atttccttcg caagggcta cctttcccct     600
tacttcatca cgacaacga cactcagcag gctgtcctgg acaaccctgc agtgctgctt     660
gttcgcaata agatttcttc cctcccagac ttcctcccac tgttggagaa ggttgtggag     720
tccaaccgtc ctttgctgat catcgcagaa gacgtcgagg gcgagccttt gcagaccctg     780
gttgtgaact ccatccgcaa gaccatcaag gtcgttgcag tgaagtctcc ttacttcggt     840
gaccgccgca aggcgttcat ggatgacctg gctattgtca ccaaggcaac tgtcgtggat     900
ccagaagtgg gcatcaacct caacgaagct ggcgaagaag ttttcggtac cgcacgccgc     960
atcaccgttt ccaaggacga aaccatcatc gttgatggtg caggttccgc agaagacgtt    1020
gaagcacgtc gcggccagat ccgtcgcgaa atcgccaaca ccgattccac ctgggatcgc    1080
gaaaaggcag aagagcgttt ggctaagctc tccggtggta ttgctgtcat ccgcgttggt    1140
gcagcaactg aaaccgaagt caacgaccgc aagctgcgtg tcgaagatgc catcaacgct    1200
gctcgcgcag cagcacaaga aggcgttatc gctggtggcg gttccgcttt ggttcagatc    1260
gctgagactc tgaaggctta cgccgaagaa ttcgaaggcg accagaaggt cggcgttcgc    1320
gcactggcta ctgctttggg caagccagcg tactggatcg cctccaacgc aggccttgac    1380
ggctctgttg ttgttgcacg cactgctgct ctgccaaacg gcgagggctt caacgctgca    1440
actttggaat acggaaacct gatcaacgac ggtgtcatcg acccagtcaa ggtcacccat    1500
tccgcagtag tgaatgcaac ctctgttgca cgcatggttc tgaccactga gcttctgtt    1560
gttgagaagc ctgcagaaga agcagccgat gcacatgcag acatcatca ccactaa      1617
```

<210> SEQ ID NO 18
<211> LENGTH: 810
<212> TYPE: DNA
<213> ORGANISM: Corynebacterium glutamicum
<220> FEATURE:
<221> NAME/KEY: misc_feature
<222> LOCATION: (1)..(810)
<223> OTHER INFORMATION: RNA degradation/processing gene mutM2

<400> SEQUENCE: 18

```
atgcctgaag gacacgtgat tcatcgacta gctggggaac tcaccaagaa ttttggcgat      60
accatttgg acgccacttc acctcaagga cgctttgctt ctgaagcggc gatcatcaac     120
ggtcaccgca tcgcggttgc ggaggcttac ggcaagcacc tgttcgtcga gttcgatgcg     180
gatcaccctg agcacatttt gtatatccat ttgggtctaa ttggcacgtt gcagtttgaa     240
cctgcgaag aaacccgcgg gcagattcgc ctgcaccttt ccgacgggga gatcgcagct     300
aatttgcgcg gaccccaatg ggtgcaggttg atcaccgatg cagagcacac ccaggccatt     360
```

```
ggaaaattgg gcgctgatcc gattcgcgat gatgccgatc cggaaccaat tcggattaag    420
gtgcagcgct cagggcgaag cattggttcg ttgttgatgg atcagaagct tttcgcaggt    480
gtgggaaata tctaccgtgc ggagacactt ttccgactgg ggatttcacc gttcaccatt    540
ggaaaagaca tcaccacggc acagttccga tccatttggg cggatcttgt tgggttgatg    600
aaagacggtg ttgtggctgg tcggattgat actgtgcgcc cggaacacac accggaggcg    660
atgggtaggc caccgcggaa agatgatcac ggcggtgagg tttacaccta tcggcgaacc    720
ggtcaagagt gctttctgtg cgcaactccc atcaaggagc aggtcatgga gggtcgcaac    780
ttattttggt gtcccggctg ccaacgctag                                    810

<210> SEQ ID NO 19
<211> LENGTH: 1275
<212> TYPE: DNA
<213> ORGANISM: Corynebacterium glutamicum
<220> FEATURE:
<221> NAME/KEY: misc_feature
<222> LOCATION: (1)..(1275)
<223> OTHER INFORMATION: RNA degradation/processing gene rhlE

<400> SEQUENCE: 19
gtgtcttctg aaagccccag acctacgttc acagagctcg gcgttgcggt ggaaatcacc     60
gacgcactcg aagccctcgg catcaaccga actttcgcga tccaggagta cacacttccc    120
atcgcgctcg acgccacga cttcatcggc caagcccgca ccggcatggg caaaacctac    180
ggattcggtg tcccactcct cgatagagtc ttcgactcag ccgacgtcgc agcaaccgac    240
ggaacccccc gagccctcgt catcgtgccc acccgagaac tcgcagtcca agtcggcgac    300
gacctccaac gcgcagcaac caacctgccg ctaaagatct tcaccttcta cggcggcaca    360
ccctacgaag aacagatcga cgcactcaaa gtcggcgtcg acgttgtcgt aggcacaccc    420
ggacgactac tcgacctgca caaacgaggc gcgctatcgc tcgacaaagt agcgatccta    480
gtcctcgatg aagccgacga aatgctcgat ctgggctttc tgcccgacat cgaaaaaatc    540
ctccgtgccc tcacccacca gcatcaaacc atgctgttct ctgccacgat gcccggcgcg    600
atcctcacac tcgcacgcag cttcctgaac aaaccagtgc acatccgagc cgagacatcg    660
gacgcctcag caacacacaa accaccagac aagtggtttt tcaggcaca caaaatggac    720 aaggaagcca tcaccgcgaa aatcctgcaa gcgaaagatc gcggcaaaac gatcatcttc    780
gcccgcacga acgcaccgc agcgcaagtt gccgaagacc tagcctccag aggattctcc    840
gtcggatcag tgcacggcga tatgggccaa ccagcccgcg agaaatcact caacgcattc    900
cgcacaggaa aaattgacat ccttgtagcc acagacgtag ccgcccgagg catcgatgtt    960
gatgacgtca cccacgtcat caactaccaa acccccgacg atcctatgac ctacgtccat   1020
cgtatcggac gcacgggacg cgcagggcac aacggaacag ccgtcactct tgtcggctac   1080
gacgaaaccc tcaaatggac cgtcatcgac aacgaactcg aactcggcca accaaaccca   1140
ccacaatggt tctccaccctc accagagctg cttgaagcac tcgacatccc agaaggtgtc   1200
accgaacgag tcggaccacc aaccaaagtt ctaggcggaa cagccccacg accaccacgc   1260
cgcacccgga aataa                                                   1275

<210> SEQ ID NO 20
<211> LENGTH: 2433
<212> TYPE: DNA
<213> ORGANISM: Corynebacterium glutamicum
```

<220> FEATURE:
<221> NAME/KEY: misc_feature
<222> LOCATION: (1)..(2433)
<223> OTHER INFORMATION: RNA degradation/processing gene rho

<400> SEQUENCE: 20

| | | | | | | |
|---|---|---|---|---|---|---|
| gtgacaacca | cagacaacac | cgcagcgaat | cagggtgaac | tgaccgccct | ccgactgccg | 60 |
| gatctgcgca | aaattgccgc | cgaccttggg | ctcaagggaa | cctcggcatt | gcgtaagggc | 120 |
| gatctgatca | acgccatctc | tgcagcccgc | gagggtaagc | caaccgcagc | tgcgaagaag | 180 |
| acttccccac | gcaaggcccc | atcacgcacc | cgtgcgacac | agccttccgc | accggttgag | 240 |
| caagcacaag | aagctcccgc | gcaaacttca | actgcacctg | cttcagcacc | atctgaagag | 300 |
| actcccgcag | ctcccgctcg | tcgtggacgt | cgccgtgtaa | ccaccaccgc | gaccacccca | 360 |
| gagccagcag | cgcctgcaca | atcccagcct | gcagaagctc | aaccagcaca | gactcaggct | 420 |
| gcacagcaag | aagaacttcc | tgttgcagcg | aaggagtccg | caccagctac | agaaaacact | 480 |
| cagggccaat | cccagggcca | agctcagggc | gatgagcacg | atgatcgctt | tgagtcccgt | 540 |
| tctgctgcac | gccgagcacg | ccgcaaccgt | cagcgccaga | tccaccgcga | tggcgatgac | 600 |
| aatgcgaatg | caaacacaga | gtctgagcag | aacacccctg | cccagaatgc | aaccgcacag | 660 |
| gctgagtctg | agcagactgc | agctcctgca | caggctgaag | cagctgagca | gaaccagaac | 720 |
| gataacagcg | agtcctccga | gaaccgcagc | gataactacc | gcaacaacaa | tcgtcgttcc | 780 |
| cgcaacaacc | ggaacaatcg | caattaccgc | gataacaacg | agtcctctga | taatgcagga | 840 |
| cagtccagca | atgatgatgc | cgacaacaat | caggcacggt | ctgaggacaa | taacgacgat | 900 |
| cgccgttctc | gtaataaccg | taacaacgac | cgcaatgatc | gtaacaatcg | caattaccgc | 960 |
| gataacaacg | agtcctctga | taatgcagga | cagtccagca | atgatgatgc | cgacaacaat | 1020 |
| caggcacggt | ctgaggacaa | taacgacgat | cgccgttctc | gtaataaccg | taacaacgac | 1080 |
| cgcaatgatc | gtaacgatcg | caattaccgc | gacaaccaca | acgacgacaa | cgatgatcgc | 1140 |
| cgcaaccgtc | gcggacgccg | caaccgccgt | ggacgcaacg | accgtaacga | tcgcgataac | 1200 |
| cgggataacc | gggataaccg | cgacaacagc | aacgatggcg | acaacaacca | gcaagatgag | 1260 |
| ctgcagcagg | tagcaggcat | cctggacatc | gtggaccata | acgtcgcatt | cgtgcgcacc | 1320 |
| accggttacc | atgctgcacc | ttctgacgtg | tttgtcagca | ccagctgat | ccgccgtatg | 1380 |
| ggtcttcgtt | ccggtgacgc | cattgaaggt | caggttcgca | tgaaccaggg | tggtggcaac | 1440 |
| cacaacaacc | atggtcgcaa | ccgtcagaag | tacaacaact | tggtgcgcgt | ggagatggtt | 1500 |
| aacggtcttc | ctgctgaaga | gactcgcaac | cgtcctgagt | tcggcaagct | gactcctctg | 1560 |
| tacccgaacc | agcgtctgca | tttggaaact | gagcagaaga | ttcttaccac | tcgtgtgatc | 1620 |
| gacttgatca | tgcctattgg | taagggacag | cgtgctttga | ttgtgtcgcc | acctaaggct | 1680 |
| ggtaagacca | cgatcctgca | gaacattgcg | aacgctattt | ccaccaacaa | cccagagtgc | 1740 |
| tacctcatgg | ttgtttttggt | tgatgagcgt | ccggaagaag | ttactgatat | gcagcgctcc | 1800 |
| gtcaacggcg | aagtgattgc | ttctactttt | gatcgtccac | catcagagca | cactgcggtt | 1860 |
| gctgagctgg | cgattgagcg | tgcgaagcgc | ctggtggagc | agggccagga | cgtcgttgtt | 1920 |
| ctgcttgact | ccattactcg | tttgggccgt | gcgtacaaca | acagctcacc | tgcatcggga | 1980 |
| cgtattttgt | ccggtggtgt | ggattccaat | gcactgtacc | cgccgaagcg | tttcttgggt | 2040 |
| gctgctcgaa | acatcgaaaa | tggtggatct | ttgaccatca | tcgcaactgc | catggtggaa | 2100 |
| accggctctg | ctggtgacac | cgtgatcttc | gaggagttca | agggcactgg | taacgctgag | 2160 |

```
ctgaagctgg atcgtaagat ctctgagcgc cgcgttttcc cagctgtgga tgttaatcct      2220
tctggtactc gtaaggacga gctgttgctc aacccggacg aggctcgcat tatgcacaag      2280
ctgcgtcgta ttctgtctgc acttgataat cagcaagcca ttgatctgtt gatcaagcag      2340
ctgaagaaga ccaagtccaa tgcggaattc ctcatgcagg ttgcttccag cgctccaatg      2400
gcaggcacag aaaaagagga ggattactcc taa                                  2433
```

<210> SEQ ID NO 21
<211> LENGTH: 3066
<212> TYPE: DNA
<213> ORGANISM: Corynebacterium glutamicum
<220> FEATURE:
<221> NAME/KEY: misc_feature
<222> LOCATION: (1)..(3066)
<223> OTHER INFORMATION: RNA degradation/processing gene rne

<400> SEQUENCE: 21

```
gtgccaaata acaaggcagt agaagcagaa atctctccct cggctgtgct ggccgcggaa        60
tttgatcgag attcattgag cgaaaaaact cgcgtacatc aactggccaa acgacttgga       120 atggttttcca aggacgtcgt tgttgcgctc gatggcatcg gcctggtcaa ggttgcgcag      180
tcaaacctga gcaaagaaga agtagaaaag cttctcgacg ccctgtctca gcccgtactc       240
aacgctgccc cagctgccgt ccccgacgtt gaaccggtgg agaagattcg tcgacgcgtt       300
gagaagaatg tggaaaatga aatccaccaa atcgaagaaa agtagagcg cgaactcgcg        360 gcagtcgcgc aacctaccga cttcgaggcg gcagcccgcg aagaagtcac tgcagaactg       420
ctggaagata tcgtcccaga gatcaccccg gcgccggtgg aagcacctgt gtacacaccg       480
atctttgtgg cacctgcagt tgtacctact gaaaacgtcc aacacaccga cgatgaacag       540
gcccgcgaac gcacggcgag gaagcgccgt gggcgtcgtg gcaccggccg cggacgtgga       600
gctgaagctg aaaccgtcac cgaagtgagt gaggaggcgt cgacaagcga gtagaagag       660 gtaaacgagc caatcggaat taagggctcc actcgcttgg aggcgcaacg ccgccgtcgc       720
acggaaatgc gcgaagaaaa caaaaagcgc cgccatgtgg tgagcaccca ggagttcatg       780
gaacgccgtg aatcgatgga acgtcgcatg attgtgcgcg agcgccaacg ccacgatcac       840
ccaggtctgg tcactcaggt tggtgtgctg gaagacgatc agctggttga gcagtttgtt       900
acctctgatg cgcagatgtc catggtgggc aatatttatc tggggcgcgt tcaaaatgtg       960
ctgccaagca tggaagctgc cttcattgac attggaaaag gtcgcaacgg tgtgttgtat      1020
gccggcgaag ttgactggaa agctgctgga cttggcggac gtggacgtcg cattgagcag      1080
gcgctgaaag ccggcgacca ggttctcgtc caggtctcca aggatccatt gggccataag      1140
ggtgcgcgtt tgaccacccca aatttccctg gcgggacgtt acctggtgta cgttccaggt      1200
ggtcgcagcg ctggcatttc ccgcaaactg cctggacctg agcgcaagcg tctgaaggaa      1260
atccttggcc gcgttgtccc agcgcagggt ggaaccatca tccgaactgc tgctgaaggt      1320
gtgtcggaag aaaacatcgc agctgacgtg aaccgtctgc acaccctgtg ggagcagatc      1380
aaggaacgca ctgcgaagga aaagaagtcc cgcggttcca agccgatcac catgtatgaa      1440
gagccagaca tgctggtgaa ggtgatccgt gacctcttca atgaagattt cacctcactg      1500
atcgttgacg gcgaccgtgc ctggaacacc gtgcgtgcct acatccaatc agtcgctcct      1560
gatttggtgt cccgcgtgga acacttcgat cgcgcagact ttgacggcaa ggatgctttc      1620
gaagcattcg acctgaacac ccagcttgag gaagcgctgt cccgaaaggt gaacctgcca      1680
tcgggtggat cgctgatcat cgaccgcacc gaagccatga cggtgatcga tgtgaacacc      1740
```

```
ggacgctaca ccggcaaggg tggtggcaac ttggaagaaa ccgtcacgct caacaacatt    1800
gaagctgccg aagaaatcgt gcgccaaatg cgcctgcgtg atctcggtgg catgatcgtt    1860
gtcgacttca tcgatatggt gctgccagaa accaagaat tggtcctgcg ccgactcaat     1920
gaagcgctag aaaacgatcg cacccgccac caagtctctg aggtaacctc actgggactt    1980
gttcagatga cccgcaaacg catcggcgcg ggcctgctgg aaaccttctc ttcaccgtgt    2040
gagcactgtg aaggccgagg catcatcgtt catgttgatc cagtagacac cgttgacgag    2100
cgcgttgagg cgaaagcgga agagcgtagc cgtcgtcacc agcgttccaa tagcactgag    2160
aaggcagctg cggagcaccc gatggttgtt gccatgcgtg atctcgtgga aagcgatgaa    2220
cacgatctgg atcaagaatt tgaggaactc gctgcatcag tgatcgtcct cgatgactcc    2280
gatctagatg atgtggtcaa cgacaagctc gacgagcctg agcgcattct tgctgaatcc    2340
accgtggaac cagaggaagg accacgcagg agggcccgcc gtcaacgtca ggaatctgct    2400
gcggatgata ttgccgcgat tgcagctgct gccgtggaca ttgcttctga agaagaccct    2460
gatgagcctt cgggatcgtc gtatgtgtct gaccttgagg cagagcctat tgcacctgta    2520
gttgagaagg ctgctgaacc tgtggctgag ccaaccgctg attatgaaaa ggcacgtgcc    2580
gaatttgagg caagcccacg caggcgccgc aagactcgtg gcaattcacg ttcggatcat    2640
gctccaaagc cagaggattt cgcacctgtg gttgaagagg ttgctgagac tccagtgaag    2700
acacctgcgc ggaaggctcc acgccgtaac cgtccaagtg agctcagttc cggtgcgccg    2760
tcctctgcac cattgaccag gaaccgtcgc cgcgcagtgc gccgtcaact ggtggaagct    2820
cctgagaccg tcgttgagat agcacctgaa gcagcaccag aacaggttgc agagcctcag    2880
gttgaattcg accagccaga caaccgccga aagcgtcgtc gtgctgtgcg cgtgacagcg    2940
gcgccggtgg agaagaaggt ggcgtcgaca agcaatgcgc gggcgccgaa gaaggaacct    3000
caggcggcga gcaccaccaa cccaggccgc cgtaggcggg ctacccgacg aggcccacga    3060
agctag                                                              3066

<210> SEQ ID NO 22
<211> LENGTH: 2157
<212> TYPE: DNA
<213> ORGANISM: Corynebacterium glutamicum
<220> FEATURE:
<221> NAME/KEY: misc_feature
<222> LOCATION: (1)..(2157)
<223> OTHER INFORMATION: RNA degradation/processing gene cg2160/ RNAse J

<400> SEQUENCE: 22
atgaatgatt cccgaaatcg cggccggaag gttacccgca aggcgggccc accagaagct      60
ggtcaggaaa accatctgga taccctgtc tttcaggcac cagatgcttc ctctaaccag       120
agcgctgtaa aagctgagac cgccggaaac gacaatcggg atgctgcgca aggtgctcaa      180
ggatcccaag attctcaggg ttcccagaac gctcaaggtt cccagaaccg cgagtccgga      240
aataacaacc gcaaccgttc caacaacaac cgtcgcggtg tcgtggacg tcgtggatcc       300 ggaaacgcca atgagggcgc gaacaacaac agtggtaacc agaaccgtca gggcggaaac      360
cgtggcaacc gcgtggcgg acgccgaaac gttgttaagt cgatgcaggg tgcggatctg      420
acccagcgcc tgccagagcc accaaaggca ccggcaaacg gtctgcgtat ttacgcactt      480
ggtggcattt ccgaaatcgg tcgcaacatg accgtgtttg agtacaacaa ccgtctgctc      540
atcgtggact gtggtgtgct cttcccatct tcaggtgagc caggcgttga cctgattctt      600
cctgacttcg gcccaattga ggatcacctg caccgcgtcg atgcattggt ggttactcac      660
```

```
ggacacgaag accacattgg tgctattccc tggctgctga agctgcgcaa cgatatccca    720
attttggcat cccgtttcac cttggctctg attgcagcta agtgtaagga acaccgtcag    780
cgtccgaagc tgatcgaggt caacgagcag tccaatgagg accgcggacc gttcaacatt    840
cgcttctggg ctgttaacca ctccatccca gactgccttg gtcttgctat caagactcct    900
gctggtttgg tcatccacac cggtgacatc aagctggatc agactcctcc tgatggacgc    960
ccaactgacc tgcctgcatt gtcccgtttc ggtgacgagg cgtggacttg atgctgtgt    1020 gactccacca acgccaccac ccctggtgtt tctggatctg aagctgatgt tgctccaacc   1080
ctgaagcgtt tggtcggcga tgctaagcag cgcgtcattt tggcgtcgtt tgcttccaac   1140
gtgtaccgcg ttcaggcagc tgtggatgct gctgttgcgt ccaaccgtaa ggttgcattc   1200
aacggtcgtt ccatgattcg caacatggag atcgcggaga agcttggtta cctgaaggca   1260
cctcgcggaa ccattatttc catggatgat gcttctcgta tggctcctca caaggtcatg   1320
ctgattacca ctggtactca gggtgagcct atggctgcgc tgtctcgcat ggcgcgtcgt   1380
gagcaccgac agatcactgt ccgtgatgga gacttgatta tcctttcttc ctccctggtt   1440
ccaggtaacg aagaagcagt gttcggtgtc atcaacatgc tggctcagat cggtgcaact   1500
gttgttaccg gtcgcgacgc caaggtgcac acctcgggcc acggctactc cggagagctg   1560
ttgttcttgt acaacgccgc tcgtccgaag aacgctatgc ctgtccacgg cgagtggcgc   1620
cacctgcgcg ccaacaagga actggctatc tccactggtg ttaaccgcga caacgttgtg   1680
cttgcacaaa acgtgttgt ggttgatatg gtcaacggtc gcgcacaggt tgttggtcag   1740
attccagttg gtaaccttta cgtcgacggt gtcaccatgg gtgatattga gcggacatc    1800 cttgcagacc gtacctcgct tggtgagggt ggcttgatct cgatcactgc tgtcatcgac   1860
aaccgcactg gccgtctgtt ggagcgccca accgttcaga ccagcggttt ctctgaggat   1920
gcaaagtcca tgatgggtga ggtcactgag ctgtccgaaa ccaccatgaa tgatcttgca   1980
gctgaaggtg aaaacgatcc ttaccgcatg gttcagcagc tgcgccgcaa gctctctcgc   2040
ttcgtcgagc agaagtggaa cgccagccg gtcatcatgc caaccgtcat tccgatgact   2100
gcggaaacca cgcacatcgg tgacgatgag gttcgcgctt cacgcgagtc cctgtaa      2157
```

<210> SEQ ID NO 23
<211> LENGTH: 101
<212> TYPE: DNA
<213> ORGANISM: Corynebacterium glutamicum
<220> FEATURE:
<221> NAME/KEY: Native promoter sequence for cg1144
<222> LOCATION: (1)..(101)

<400> SEQUENCE: 23

```
tagcatagat gacttgacac tgttgcagca ggcggttttc acctggcctc ttaggatttg     60
gtcaaatggt tgcaacgacg ccagggaagg aggcgcaccc c                         101
```

<210> SEQ ID NO 24
<211> LENGTH: 61
<212> TYPE: DNA
<213> ORGANISM: Corynebacterium glutamicum
<220> FEATURE:
<221> NAME/KEY: Native promoter sequence for cg2453
<222> LOCATION: (1)..(61)

<400> SEQUENCE: 24

```
tgtgcccaag gaaactcaac acccctgcat atactttcc gctgtggaac aatgggagcg      60
c                                                                     61
```

<210> SEQ ID NO 25
<211> LENGTH: 62
<212> TYPE: DNA
<213> ORGANISM: Corynebacterium glutamicum
<220> FEATURE:
<221> NAME/KEY: Native promoter sequence for cshA
<222> LOCATION: (1)..(62)

<400> SEQUENCE: 25
ccgcggcgga agtggaattg catatggagt tttgatgata tttagcgtaa cttaaaggaa    60
ca                                                                  62

<210> SEQ ID NO 26
<211> LENGTH: 179
<212> TYPE: DNA
<213> ORGANISM: Corynebacterium glutamicum
<220> FEATURE:
<221> NAME/KEY: Native promoter sequence for dnak
<222> LOCATION: (1)..(179)

<400> SEQUENCE: 26
aaattaagaa agttgagtct agtgggaaca actttgtggc atttaccgtt gccatatatg    60
taagcttgag tcaggcaggc tcaatgagga gttttttctta ccggcgaaag tcggtgggaa  120
gcaagtcaaa gctcaagccg tggacaatac taaaatcacc taaaacagga ggcaccatt   179

<210> SEQ ID NO 27
<211> LENGTH: 129
<212> TYPE: DNA
<213> ORGANISM: Corynebacterium glutamicum
<220> FEATURE:
<221> NAME/KEY: Native promoter sequence for eno
<222> LOCATION: (1)..(129)

<400> SEQUENCE: 27
tcgccactaa tttcaactga ttgcctcatc gaaacaagat tcgtgcaaca attgggtgta    60
gacgtgattg aagacatttg atcacgtgaa taattctagt tagctcccaa gttggcatag   120
gaggccaca                                                           129

<210> SEQ ID NO 28
<211> LENGTH: 154
<212> TYPE: DNA
<213> ORGANISM: Corynebacterium glutamicum
<220> FEATURE:
<221> NAME/KEY: Native promoter sequence for gpsI
<222> LOCATION: (1)..(154)

<400> SEQUENCE: 28
tggtgaataa aactcgtgtc gagtagcgct aaaactgata gtggggaaaa ctggagagaa    60
ctggtaaggt ttttaccgtt ctagaccgca gaaatcttcg cggcgacacc gatgatcgcc   120
gagcagaact aaacatgagg agacctactc gcat                               154

<210> SEQ ID NO 29
<211> LENGTH: 205
<212> TYPE: DNA
<213> ORGANISM: Corynebacterium glutamicum
<220> FEATURE:
<221> NAME/KEY: Native promoter sequence for groEL
<222> LOCATION: (1)..(205)

<400> SEQUENCE: 29
agagcatttg aagctataaa atcttgcact cacacccctt gagtgctaga aaagtagtta    60
gcactcaact aatcagagtg ccaatattga tcatcaactg cttggtgggt gaggttggtc   120
cacactcact aaccgtgccg tcgcgggcgc ctaccgggca gaagacgtga gtgtcgtcct    180
acaaatattt caggagcaca aacac                                          205

<210> SEQ ID NO 30
<211> LENGTH: 59
<212> TYPE: DNA
<213> ORGANISM: Corynebacterium glutamicum
<220> FEATURE:
<221> NAME/KEY: Native promoter sequence for mutM2
<222> LOCATION: (1)..(59)

<400> SEQUENCE: 30
ccgcaggcca cgcttagttt tttatcaaat cggcacaccg gctactaagg ttggtgatt     59

<210> SEQ ID NO 31
<211> LENGTH: 59
<212> TYPE: DNA
<213> ORGANISM: Corynebacterium glutamicum
<220> FEATURE:
<221> NAME/KEY: Native promoter sequence for rhlE
<222> LOCATION: (1)..(59)

<400> SEQUENCE: 31
aaaagaatcg ttgtattgga atgaccctat tgtaaccgtg caacgatagt atctaagtt     59

<210> SEQ ID NO 32
<211> LENGTH: 101
<212> TYPE: DNA
<213> ORGANISM: Corynebacterium glutamicum
<220> FEATURE:
<221> NAME/KEY: Native promoter sequence for rho
<222> LOCATION: (1)..(101)

<400> SEQUENCE: 32
ttcaattaca cagaagccga gttcagccat attttcgcc cgtgatatga aaaacgggta    60
catcaccgca gcttggtctg aactgcaatg aaaggaaatc t                        101

<210> SEQ ID NO 33
<211> LENGTH: 140
<212> TYPE: DNA
<213> ORGANISM: Corynebacterium glutamicum
<220> FEATURE:
<221> NAME/KEY: Native promoter sequence for rne
<222> LOCATION: (1)..(140)

<400> SEQUENCE: 33
tatatttgtg ggtcggaaaa tttagacaat acagttttag attggcgcac gtacctgcgc    60
ggcggcggta ggagatcttg tccctaccag cgcccgggtg cactgctcaa tcgtggagat   120
aagaaaatag gagtgtcgct                                               140

<210> SEQ ID NO 34
<211> LENGTH: 414
<212> TYPE: PRT
<213> ORGANISM: Corynebacterium glutamicum
<220> FEATURE:
<221> NAME/KEY: MISC_FEATURE
<222> LOCATION: (1)..(414)
<223> OTHER INFORMATION: Translated Polypeptide for RNA
      degradation/processing gene cg1144

<400> SEQUENCE: 34

```
Met Ala Phe Gly Phe Ser Arg Arg Lys Lys Asn Lys Asp Lys
1               5                   10                  15

Asn Pro Asn Glu Asn Ser Ala Val Pro Ala His Ser Glu Asp Ser Pro
            20                  25                  30

Gln Glu Val Phe Glu Gly Asn Arg Gln Val Gly Asp Pro Ile Glu
            35                  40                  45

Gln Gln Val Asp Arg Asp Ala Lys Gly Arg Leu Thr Ala Ala Asp Phe
    50                  55                  60

Leu Pro Asp Ala Asp Leu Pro Gln Leu Asn Arg Ser Arg Ala Asn Met
65                  70                  75                  80

Leu Arg Arg Glu Leu Glu Tyr Arg Phe Ser Leu Gln Asn Ala His Ile
                85                  90                  95

Asn Ile Asp Gly Asn Thr Ala Met Ile Gln Arg Ser Asp Gly Gly Ala
            100                 105                 110

Ala His Val Ser Leu Arg Thr Leu Ala Met Asn Ala Ala Gly Leu Asp
            115                 120                 125

Asn Phe Asp Gln Leu Pro Glu Leu Val Glu Ser Phe Val His Gly Thr
    130                 135                 140

Leu Ala Asp Ala Thr Leu Asn Asp Leu Ser Thr Ala Asp Leu Tyr Lys
145                 150                 155                 160

Ala Leu Arg Leu Arg Leu Leu Pro Thr Pro Gly Glu Gly Asp Asp Leu
                165                 170                 175

Val Glu His Gly Leu Asp Arg Glu Ser Gln Ile Arg Asp Asp Ser Ile
            180                 185                 190

Leu Arg Thr Phe Thr Ser Asp Met Ser Ile Ala Leu Val Leu Asp Thr
    195                 200                 205

Glu His Ala Ile Arg Ile Gln Pro Leu Lys Glu Leu Glu Glu Phe Asp
210                 215                 220

Asp Leu Ser Ala Leu Glu Arg Ala Ala Asp Arg Asn Thr Trp Gln Glu
225                 230                 235                 240

Leu Tyr Asp Ala Asn Val Asp Ala Ser Phe Val Asp Ala Glu Ser Asp
                245                 250                 255

Ser Glu Gly Ser Ser Phe Trp Ala Phe Glu Ser Asn Ser Tyr Tyr Leu
            260                 265                 270

Gly Ser Ala Pro Leu Phe Leu Asn Asp Leu Leu Ala Lys Trp Ala Pro
    275                 280                 285

Asp Leu Asp Gln Ser Asp Gly Val Ile Phe Ala Val Pro Asp Arg Asp
290                 295                 300

Leu Leu Ile Ala Arg Pro Val Thr Thr Gly Glu Asp Leu Met Asn Gly
305                 310                 315                 320

Ile Thr Ala Met Val Arg Ile Ala Met Arg Phe Gly Leu Gly Asn Pro
                325                 330                 335

Thr Ser Ile Ser Pro Arg Leu His Leu Leu Arg Asp Asn Gln Val Thr
            340                 345                 350

Thr Phe Thr Asp Phe Arg Val Val Ser Pro Glu Met Glu Ala Glu Trp
    355                 360                 365

Glu Asp Ser Ala Phe Asp Ala Pro Pro Ala Gly Ala Ile Gly Ile Glu
370                 375                 380

Val Arg Pro Asp Pro Tyr Leu Met Glu Arg Leu Gln Gln Gly Gly Phe
385                 390                 395                 400

Gly Asp Phe Gly Asp Phe Gly Lys Pro Arg Asp Leu Asp Met
                405                 410
```

-continued

```
<210> SEQ ID NO 35
<211> LENGTH: 469
<212> TYPE: PRT
<213> ORGANISM: Corynebacterium glutamicum
<220> FEATURE:
<221> NAME/KEY: MISC_FEATURE
<222> LOCATION: (1)..(469)
<223> OTHER INFORMATION: Translated Polypeptide for RNA
      degradation/processing gene cg2453

<400> SEQUENCE: 35

Met Lys Leu Tyr Ala Ala Val Leu Asp Phe Glu Pro Val Ala Gln Glu
1               5                   10                  15

Phe Gly Val Glu Arg Gly Phe Asp Pro His Ile His Asp Glu Ala Ala
            20                  25                  30

Ser Ser Val Asp Arg Tyr Ala Gln Glu Arg Glu Asp Leu Leu His Met
        35                  40                  45

Pro Phe Val Thr Ile Asp Pro Val Gly Ser Arg Asp Leu Asp Gln Ala
    50                  55                  60

Val Leu Ile Glu Glu Ile Asp Ser Gly Phe Arg Val His Tyr Ala Ile
65                  70                  75                  80

Ala Asp Val Ala Ala Phe Val Glu Pro Gly Ser Glu Leu Glu Lys Ile
                85                  90                  95

Ser Leu His Arg Gly Gln Thr Ile Tyr Leu Pro Asp Ser Pro Ala Arg
            100                 105                 110

Leu His Pro Glu Glu Leu Ser Glu Asp Ala Ala Ser Leu Leu Glu Gly
        115                 120                 125

Gln Thr Arg Pro Ala Val Val Trp Ser Ile Asp Leu Asp Glu Arg Gly
    130                 135                 140

Glu Val Thr Ala Thr Lys Val Arg Arg Gly Leu Val Lys Ser Arg Ala
145                 150                 155                 160

Arg Leu Asp Tyr Asp Gln Ala Gln Ile Asp Ala Glu Asn Gly Arg Leu
                165                 170                 175

His Pro Ser Ile Ser Leu Leu Pro Lys Val Gly Gln Leu Arg Gln Glu
            180                 185                 190

Ser Ala Leu Arg Arg Glu Ala Val Asn Leu Ser Ile Pro Ser Gln Arg
        195                 200                 205

Val Val Lys Val Pro Asn Asp Asp Ala Gly Glu His Tyr Glu Ile Val
    210                 215                 220

Ile Glu Pro Arg Pro His Ile Met Asp Tyr Asn Ser Glu Ile Ser Leu
225                 230                 235                 240

Leu Thr Gly Met Val Ala Gly Glu Met Met Val Lys Ala Gly His Gly
                245                 250                 255

Leu Leu Arg Thr Leu Ala Pro Ala Thr Lys Glu Ser Glu Ala Thr Phe
            260                 265                 270

Arg Ser Glu Ala Gln Ala Leu Gly Phe Glu Ile Ala Pro Glu Gln Pro
        275                 280                 285

Ile Gly Glu Phe Leu Gln Ser Val Asp Pro Asn Thr Pro Lys Gly Met
    290                 295                 300

Ala Ile Gln Arg Glu Ala Gln Lys Leu Leu Arg Gly Ser Gly Tyr Ala
305                 310                 315                 320

Ser Val Lys Asn Gly Asp Ser Glu Val His Ser Gly Val Gly Tyr
                325                 330                 335

Tyr Ala His Val Thr Ala Pro Leu Arg Arg Leu Ile Asp Arg Phe Ala
            340                 345                 350
```

```
Thr Glu His Cys Leu Ala Ile Ala Ser Gly Thr Asp Val Pro Glu Trp
        355                 360                 365

Val Thr Arg Val Glu Glu Gln Val Leu Asp Thr Met Lys Tyr Ser Ser
    370                 375                 380

Ile Leu Ala Ser Gln Val Asp Asn Ala Cys Leu Asp Leu Thr Glu Ala
385                 390                 395                 400

Thr Val Leu Lys Tyr Trp Glu Gly Gln Asn Phe Asn Ala Val Val Val
                405                 410                 415

Ala Ser Glu Pro Glu Lys Asn Ser Ala Arg Leu Phe Val Tyr Lys Pro
                420                 425                 430

Pro Val Leu Ala Lys Cys Ile Gly Ala Pro Glu Gln Gly Thr Asn Gln
            435                 440                 445

Glu Val Thr Leu Val Thr Ala Asn Leu Lys Lys Arg Glu Val Leu Phe
    450                 455                 460

Ala Trp Pro Ala Asp
465

<210> SEQ ID NO 36
<211> LENGTH: 732
<212> TYPE: PRT
<213> ORGANISM: Corynebacterium glutamicum
<220> FEATURE:
<221> NAME/KEY: MISC_FEATURE
<222> LOCATION: (1)..(732)
<223> OTHER INFORMATION: Translated Polypeptide for RNA
      degradation/processing gene cshA

<400> SEQUENCE: 36

Met Ser Asn Thr Glu Asn Val Asn Gly Asp Val Glu Gln Pro Asn Asn
1               5                   10                  15

Val Ile Ser Ser Glu Ser Gln Glu Thr Pro Gln Gly Asp Ser Ala Ser
            20                  25                  30

Ala Asp Phe Ala Leu Glu Thr Pro Thr Asn Thr Val Glu Asp Ala Pro
        35                  40                  45

Ala Ser Glu Gly Ser Glu Glu Ile Thr Arg Val Ala Asp Thr Ser Glu
    50                  55                  60

Asp Ala Asp Ser Ala Asp Ala Asp Asn Ala Ser Asn Val Ile Asn Glu
65                  70                  75                  80

Asn Glu Asp Ser Ser Glu Gly Ala Asn Gln Pro Ser Asn Glu Ser Ser
                85                  90                  95

Ser Thr Glu Ala Lys Ser Gly Phe Asp Ala Leu Gly Leu Pro Glu Arg
            100                 105                 110

Val Leu Asp Ala Val Arg Lys Val Gly Tyr Glu Thr Pro Ser Pro Ile
        115                 120                 125

Gln Ala Gln Thr Ile Pro Ile Leu Met Glu Gly Gln Asp Val Val Gly
    130                 135                 140

Leu Ala Gln Thr Gly Thr Gly Lys Thr Ala Ala Phe Ala Leu Pro Ile
145                 150                 155                 160

Leu Ser Arg Ile Asp Lys Ser Val Arg Ser Pro Gln Ala Leu Val Leu
                165                 170                 175

Ala Pro Thr Arg Glu Leu Ala Leu Gln Val Ala Asp Ser Phe Gln Ser
            180                 185                 190

Phe Ala Asp His Val Gly Gly Leu Asn Val Leu Pro Ile Tyr Gly Gly
        195                 200                 205

Gln Ala Tyr Gly Ile Gln Leu Ser Gly Leu Arg Arg Gly Ala His Ile
    210                 215                 220
```

```
Val Val Gly Thr Pro Gly Arg Ile Ile Asp His Leu Glu Lys Gly Ser
225                 230                 235                 240

Leu Asp Ile Ser Gly Leu Arg Phe Leu Val Leu Asp Glu Ala Asp Glu
            245                 250                 255

Met Leu Asn Met Gly Phe Gln Glu Asp Val Glu Arg Ile Leu Glu Asp
            260                 265                 270

Thr Pro Asp Glu Lys Gln Val Ala Leu Phe Ser Ala Thr Met Pro Asn
        275                 280                 285

Gly Ile Arg Arg Leu Ser Lys Gln Tyr Leu Asn Asn Pro Ala Glu Ile
    290                 295                 300

Thr Val Lys Ser Glu Thr Arg Thr Asn Thr Asn Ile Thr Gln Arg Phe
305                 310                 315                 320

Leu Asn Val Ala His Arg Asn Lys Met Asp Ala Leu Thr Arg Ile Leu
            325                 330                 335

Glu Val Thr Glu Phe Glu Ala Met Ile Met Phe Val Arg Thr Lys His
            340                 345                 350

Glu Thr Glu Glu Val Ala Glu Lys Leu Arg Ala Arg Gly Phe Ser Ala
    355                 360                 365

Ala Ala Ile Asn Gly Asp Ile Ala Gln Ala Gln Arg Glu Arg Thr Val
370                 375                 380

Asp Gln Leu Lys Asp Gly Arg Leu Asp Ile Leu Val Ala Thr Asp Val
385                 390                 395                 400

Ala Ala Arg Gly Leu Asp Val Glu Arg Ile Ser His Val Leu Asn Phe
            405                 410                 415

Asp Ile Pro Asn Asp Thr Glu Ser Tyr Val His Arg Ile Gly Arg Thr
            420                 425                 430

Gly Arg Ala Gly Arg Thr Gly Glu Ala Ile Leu Phe Val Thr Pro Arg
    435                 440                 445

Glu Arg Arg Met Leu Arg Ser Ile Glu Arg Ala Thr Asn Ala Pro Leu
450                 455                 460

His Glu Met Glu Leu Pro Thr Val Asp Gln Val Asn Asp Phe Arg Lys
465                 470                 475                 480

Val Lys Phe Ala Asp Ser Ile Thr Lys Ser Leu Glu Asp Lys Gln Met
            485                 490                 495

Asp Leu Phe Arg Thr Leu Val Lys Glu Tyr Ser Gln Ala Asn Asp Val
            500                 505                 510

Pro Leu Glu Asp Ile Ala Ala Ala Leu Ala Thr Gln Ala Gln Ser Gly
        515                 520                 525

Asp Phe Leu Leu Lys Glu Leu Pro Pro Glu Arg Arg Glu Arg Asn Asp
    530                 535                 540

Arg Arg Arg Asp Arg Asp Phe Asp Asp Arg Gly Gly Arg Gly Arg Asp
545                 550                 555                 560

Arg Asp Arg Gly Asp Arg Gly Asp Arg Gly Ser Arg Phe Asp Arg Asp
            565                 570                 575

Asp Glu Asn Leu Ala Thr Tyr Arg Leu Ala Val Gly Lys Arg Gln His
            580                 585                 590

Ile Arg Pro Gly Ala Ile Gly Ala Leu Ala Asn Glu Gly Gly Leu
    595                 600                 605

Asn Ser Lys Asp Phe Gly Arg Ile Thr Ile Ala Ala Asp His Thr Leu
    610                 615                 620

Val Glu Leu Pro Lys Asp Leu Pro Gln Ser Val Leu Asp Asn Leu Arg
625                 630                 635                 640
```

Asp Thr Arg Ile Ser Gly Gln Leu Ile Asn Ile Glu Arg Asp Ser Gly
            645                 650                 655

Gly Arg Pro Pro Arg Arg Phe Glu Arg Asp Asp Arg Gly Gly Arg Gly
        660                 665                 670

Gly Phe Arg Gly Asp Arg Asp Asp Arg Gly Gly Arg Gly Arg Asp Arg
        675                 680                 685

Asp Asp Arg Gly Ser Arg Gly Gly Phe Arg Gly Gly Arg Asp Arg Asp
        690                 695                 700

Asp Arg Gly Gly Arg Gly Gly Phe Arg Gly Arg Asp Asp Arg Gly Asp
705                 710                 715                 720

Arg Gly Gly Arg Gly Gly Tyr Arg Gly Gly Arg Asp
                725                 730

<210> SEQ ID NO 37
<211> LENGTH: 618
<212> TYPE: PRT
<213> ORGANISM: Corynebacterium glutamicum
<220> FEATURE:
<221> NAME/KEY: MISC_FEATURE
<222> LOCATION: (1)..(618)
<223> OTHER INFORMATION: Translated Polypeptide for RNA
      degradation/processing gene dnaK

<400> SEQUENCE: 37

Met Gly Arg Ala Val Gly Ile Asp Leu Gly Thr Thr Asn Ser Val Val
1               5                   10                  15

Ser Val Leu Glu Gly Gly Glu Pro Val Val Ile Ala Asn Ala Glu Gly
            20                  25                  30

Ser Arg Thr Thr Pro Ser Val Val Ala Phe Ala Lys Asn Gly Glu Val
        35                  40                  45

Leu Val Gly Gln Ser Ala Lys Asn Gln Ala Val Thr Asn Val Asp Arg
    50                  55                  60

Thr Ile Arg Ser Val Lys Arg His Ile Gly Thr Asp Trp Ser Val Ala
65                  70                  75                  80

Ile Asp Asp Lys Asn Tyr Thr Ser Gln Glu Ile Ser Ala Arg Thr Leu
                85                  90                  95

Met Lys Leu Lys Arg Asp Ala Glu Ala Tyr Leu Gly Glu Asp Val Thr
            100                 105                 110

Asp Ala Val Ile Thr Val Pro Ala Tyr Phe Glu Asp Ser Gln Arg Gln
        115                 120                 125

Ala Thr Lys Glu Ala Gly Gln Ile Ala Gly Leu Asn Val Leu Arg Ile
    130                 135                 140

Val Asn Glu Pro Thr Ala Ala Ala Leu Ala Tyr Gly Leu Glu Lys Gly
145                 150                 155                 160

Glu Gln Glu Gln Thr Ile Leu Val Phe Asp Leu Gly Gly Gly Thr Phe
                165                 170                 175

Asp Val Ser Leu Leu Glu Ile Gly Asp Gly Val Val Glu Val Arg Ala
            180                 185                 190

Thr Ser Gly Asp Asn Glu Leu Gly Gly Asp Asp Trp Asp Gln Arg Ile
        195                 200                 205

Val Asp Trp Leu Val Glu Lys Phe Gln Ser Ser Asn Gly Ile Asp Leu
    210                 215                 220

Thr Lys Asp Lys Met Ala Leu Gln Arg Leu Arg Glu Ala Ala Glu Lys
225                 230                 235                 240

Ala Lys Ile Glu Leu Ser Ser Ser Gln Ser Ala Asn Ile Asn Leu Pro
                245                 250                 255

Tyr Ile Thr Val Asp Ala Asp Lys Asn Pro Leu Phe Leu Asp Glu Thr
                260                 265                 270

Leu Ser Arg Ala Glu Phe Gln Arg Ile Thr Gln Asp Leu Leu Ala Arg
        275                 280                 285

Thr Lys Thr Pro Phe Asn Gln Val Val Lys Asp Ala Gly Val Ser Val
    290                 295                 300

Ser Glu Ile Asp His Val Val Leu Val Gly Ser Thr Arg Met Pro
305                 310                 315                 320

Ala Val Thr Glu Leu Val Lys Glu Leu Thr Gly Gly Arg Glu Pro Asn
                325                 330                 335

Lys Gly Val Asn Pro Asp Glu Val Ala Val Gly Ala Ala Leu Gln
                340                 345                 350

Ala Gly Val Leu Arg Gly Glu Val Lys Asp Val Leu Leu Asp Val
                355                 360                 365

Thr Pro Leu Ser Leu Gly Ile Glu Thr Lys Gly Gly Val Met Thr Lys
    370                 375                 380

Leu Ile Glu Arg Asn Thr Thr Ile Pro Thr Lys Arg Ser Glu Thr Phe
385                 390                 395                 400

Thr Thr Ala Glu Asp Asn Gln Pro Ser Val Gln Ile Gln Val Phe Gln
                405                 410                 415

Gly Glu Arg Glu Ile Ala Thr Ala Asn Lys Leu Leu Gly Ser Phe Glu
                420                 425                 430

Leu Gly Gly Ile Ala Pro Ala Pro Arg Gly Val Pro Gln Ile Glu Val
                435                 440                 445

Thr Phe Asp Ile Asp Ala Asn Gly Ile Val His Val Thr Ala Lys Asp
    450                 455                 460

Lys Gly Thr Gly Lys Glu Asn Thr Ile Thr Ile Gln Asp Gly Ser Gly
465                 470                 475                 480

Leu Ser Gln Asp Glu Ile Asp Arg Met Ile Lys Asp Ala Glu Ala His
                485                 490                 495

Ala Asp Glu Asp Lys Lys Arg Arg Glu Glu Gln Glu Val Arg Asn Asn
                500                 505                 510

Ala Glu Ser Leu Val Tyr Gln Thr Arg Lys Phe Val Glu Glu Asn Ser
                515                 520                 525

Glu Lys Val Ser Glu Asp Leu Lys Ala Lys Val Glu Glu Ala Ala Lys
530                 535                 540

Gly Val Glu Glu Ala Leu Lys Gly Glu Asp Leu Glu Ala Ile Lys Ala
545                 550                 555                 560

Ala Val Glu Lys Leu Asn Thr Glu Ser Gln Glu Met Gly Lys Ala Ile
                565                 570                 575

Tyr Glu Ala Asp Ala Ala Ala Gly Ala Thr Gln Ala Asp Ala Gly Ala
                580                 585                 590

Glu Gly Ala Ala Asp Asp Asp Val Val Asp Ala Glu Val Val Glu Asp
                595                 600                 605

Asp Ala Ala Asp Asn Gly Glu Asp Lys Lys
                610                 615

<210> SEQ ID NO 38
<211> LENGTH: 425
<212> TYPE: PRT
<213> ORGANISM: Corynebacterium glutamicum
<220> FEATURE:
<221> NAME/KEY: MISC_FEATURE
<222> LOCATION: (1)..(425)
<223> OTHER INFORMATION: Translated Polypeptide for RNA
    degradation/processing gene eno

```
<400> SEQUENCE: 38

Val Ala Glu Ile Met His Val Phe Ala Arg Glu Ile Leu Asp Ser Arg
1               5                   10                  15

Gly Asn Pro Thr Val Glu Ala Glu Val Phe Leu Asp Asp Gly Ser His
            20                  25                  30

Gly Val Ala Gly Val Pro Ser Gly Ala Ser Thr Gly Val His Glu Ala
        35                  40                  45

His Glu Leu Arg Asp Gly Gly Asp Arg Tyr Leu Gly Lys Gly Val Leu
    50                  55                  60

Lys Ala Val Glu Asn Val Asn Glu Glu Ile Gly Asp Glu Leu Ala Gly
65                  70                  75                  80

Leu Glu Ala Asp Asp Gln Arg Leu Ile Asp Glu Ala Met Ile Lys Leu
                85                  90                  95

Asp Gly Thr Ala Asn Lys Ser Arg Leu Gly Ala Asn Ala Ile Leu Gly
            100                 105                 110

Val Ser Met Ala Val Ala Lys Ala Ala Ala Asp Ser Ala Gly Leu Pro
        115                 120                 125

Leu Phe Arg Tyr Ile Gly Gly Pro Asn Ala His Val Leu Pro Val Pro
    130                 135                 140

Met Met Asn Ile Ile Asn Gly Gly Ala His Ala Asp Ser Gly Val Asp
145                 150                 155                 160

Val Gln Glu Phe Met Ile Ala Pro Ile Gly Ala Glu Thr Phe Ser Glu
                165                 170                 175

Ala Leu Arg Asn Gly Ala Glu Val Tyr His Ala Leu Lys Ser Val Ile
            180                 185                 190

Lys Glu Lys Gly Leu Ser Thr Gly Leu Gly Asp Glu Gly Gly Phe Ala
        195                 200                 205

Pro Ser Val Gly Ser Thr Arg Glu Ala Leu Asp Leu Ile Val Glu Ala
    210                 215                 220

Ile Glu Lys Ala Gly Phe Thr Pro Gly Lys Asp Ile Ala Leu Ala Leu
225                 230                 235                 240

Asp Val Ala Ser Ser Glu Phe Phe Lys Asp Gly Thr Tyr His Phe Glu
                245                 250                 255

Gly Gly Gln His Ser Ala Ala Glu Met Ala Asn Val Tyr Ala Glu Leu
            260                 265                 270

Val Asp Ala Tyr Pro Ile Val Ser Ile Glu Asp Pro Leu Gln Glu Asp
        275                 280                 285

Asp Trp Glu Gly Tyr Thr Asn Leu Thr Ala Thr Ile Gly Asp Lys Val
    290                 295                 300

Gln Ile Val Gly Asp Asp Phe Phe Val Thr Asn Pro Glu Arg Leu Lys
305                 310                 315                 320

Glu Gly Ile Ala Lys Lys Ala Ala Asn Ser Ile Leu Val Lys Val Asn
                325                 330                 335

Gln Ile Gly Thr Leu Thr Glu Thr Phe Asp Ala Val Asp Met Ala His
            340                 345                 350

Arg Ala Gly Tyr Thr Ser Met Met Ser His Arg Ser Gly Glu Thr Glu
        355                 360                 365

Asp Thr Thr Ile Ala Asp Leu Ala Val Ala Leu Asn Cys Gly Gln Ile
    370                 375                 380

Lys Thr Gly Ala Pro Ala Arg Ser Asp Arg Val Ala Lys Tyr Asn Gln
385                 390                 395                 400
```

-continued

Leu Leu Arg Ile Glu Gln Leu Leu Gly Asp Ala Gly Val Tyr Ala Gly
              405                 410                 415

Arg Ser Ala Phe Pro Arg Phe Gln Gly
            420                 425

<210> SEQ ID NO 39
<211> LENGTH: 753
<212> TYPE: PRT
<213> ORGANISM: Corynebacterium glutamicum
<220> FEATURE:
<221> NAME/KEY: MISC_FEATURE
<222> LOCATION: (1)..(753)
<223> OTHER INFORMATION: Translated Polypeptide for RNA
      degradation/processing gene gpsI

<400> SEQUENCE: 39

Met Ser Asp Val Lys Tyr Phe Glu Asp Thr Glu Phe Gly Leu Ile Glu
1               5                   10                  15

Ala Val Ala Thr Ile Asp Asn Gly Asp Phe Gly Thr Arg Thr Ile Arg
            20                  25                  30

Phe Glu Thr Gly Gln Leu Ala Arg Gln Ala Asp Gly Ala Val Thr Thr
        35                  40                  45

Tyr Leu Asp Asp Asp Thr Met Leu Leu Ala Thr Thr Ala Ser Asn
    50                  55                  60

Gln Pro Arg Glu Gly Phe Asp Phe Phe Pro Leu Thr Val Asp Val Glu
65                  70                  75                  80

Glu Arg Met Tyr Ala Ala Gly Arg Ile Pro Gly Ser Phe Phe Arg Arg
                85                  90                  95

Glu Gly Arg Pro Ser Thr Glu Ala Ile Leu Ala Cys Arg Leu Ile Asp
            100                 105                 110

Arg Pro Leu Arg Pro Thr Phe Val Lys Gly Leu Arg Asn Glu Val Gln
        115                 120                 125

Ile Val Val Thr Val Met Ser Met Asn Pro Glu Asp Tyr Tyr Asp Val
    130                 135                 140

Val Ala Ile Asn Gly Ala Ser Ala Ala Thr Arg Ile Ser Gly Leu Pro
145                 150                 155                 160

Val Ser Gly Ala Val Gly Gly Val Arg Met Ala Leu Val Val Asp Glu
                165                 170                 175

Lys His Pro Glu Gly Gln Trp Val Ala Phe Pro Thr His Ala Gln His
            180                 185                 190

Glu Gln Ser Val Phe Glu Ile Val Val Ala Gly Arg Leu Val Glu Arg
        195                 200                 205

Lys Arg Gly Asn Lys Thr Phe Ser Asp Val Ala Val Met Met Val Glu
    210                 215                 220

Ala Gly Ala Ser Glu Asn Val Val Asn Arg Val Lys Asp Gly Ala Pro
225                 230                 235                 240

Ala Pro Thr Glu Lys Ile Val Ser Asp Gly Leu Glu Ala Ala Lys Pro
                245                 250                 255

Phe Ile Asp Ile Leu Cys Arg Ala Gln Glu Gly Leu Ala Gln Arg Val
            260                 265                 270

Gly Asn Ala Ala Lys Glu Phe Pro Leu Phe Pro Pro Tyr Thr Asp Glu
        275                 280                 285

Val Tyr Ser Ala Val Glu Arg Lys Val Ser Lys Leu Ala Ser Leu
    290                 295                 300

Leu Thr Leu Lys Ala Lys Gln Glu Arg Asp Asp Ala Thr Asn Ala Tyr
305                 310                 315                 320

```
Met Glu Glu Ile Glu Ala Glu Leu Leu Pro Lys Phe Glu Ala Ser Tyr
                325                 330                 335
Ser Ser Ala Ala Glu Ala Ser Lys Glu Ile Arg Ala Ala Tyr Asn Ala
            340                 345                 350
Val Met Lys Ala Ile Val Arg Arg Met Ile Leu Thr Asp His Phe Arg
        355                 360                 365
Ile Asp Gly Arg Gly Val Thr Asp Ile Arg Asp Leu Ala Val Glu Val
    370                 375                 380
Glu Leu Ile Pro Arg Ala His Gly Ser Ser Leu Phe Glu Arg Gly Glu
385                 390                 395                 400
Thr Gln Ile Leu Gly Val Thr Thr Leu Asp Met Leu Lys Met Glu Gln
                405                 410                 415
Gln Ile Asp Ser Leu Ala Pro Gly Asp Ala Lys Arg Tyr Met His His
            420                 425                 430
Tyr Asn Phe Pro Pro Tyr Ser Thr Gly Glu Thr Gly Arg Val Gly Ser
        435                 440                 445
Pro Lys Arg Arg Glu Ile Gly His Gly Ala Leu Ala Glu Arg Ala Val
    450                 455                 460
Leu Pro Val Ile Pro Ser Arg Glu Glu Phe Pro Tyr Ala Ile Arg Gln
465                 470                 475                 480
Val Ser Glu Ala Leu Gly Ser Asn Gly Ser Thr Ser Met Gly Ser Val
                485                 490                 495
Cys Ala Ser Thr Leu Ser Leu Tyr Asn Ala Gly Val Pro Leu Lys Ala
            500                 505                 510
Pro Val Ala Gly Ile Ala Met Gly Leu Val Ser Gly Glu Ile Asp Gly
        515                 520                 525
Lys Thr Glu Tyr Val Ala Leu Thr Asp Ile Leu Gly Ala Glu Asp Ala
    530                 535                 540
Phe Gly Asp Met Asp Phe Lys Val Ala Gly Thr Ala Asp Phe Ile Thr
545                 550                 555                 560
Ala Leu Gln Leu Asp Thr Lys Leu Asp Gly Ile Pro Ser Lys Val Leu
                565                 570                 575
Ser Asp Ala Leu Glu Gln Ala Arg Asp Ala Arg Leu Thr Ile Leu Asn
            580                 585                 590
Thr Met Ala Asp Val Ile Asn Gly Ala Asp Glu Met Ser Lys Phe Ala
        595                 600                 605
Pro Arg Ile Thr Thr Val Lys Ile Pro Val Ala Lys Ile Gly Glu Leu
    610                 615                 620
Ile Gly Pro Lys Gly Lys Asn Ile Asn Ala Leu Thr Glu Glu Thr Gly
625                 630                 635                 640
Ala Asn Ile Ser Ile Glu Asp Asp Gly Thr Val Phe Ile Ser Ala Ala
                645                 650                 655
Asp Gly Ala Ser Ala Glu Ala Ala Ile Glu Lys Ile Asn Ala Leu Ala
            660                 665                 670
Asn Pro Gln Leu Pro Lys Val Gly Glu Arg Phe Leu Gly Thr Val Val
        675                 680                 685
Lys Thr Thr Ala Phe Gly Ala Phe Val Ser Leu Pro Gly Arg Asp
    690                 695                 700
Gly Leu Val His Ile Ser Lys Leu Gly Asn Gly Lys Arg Val Glu Lys
705                 710                 715                 720
Val Asp Asp Val Val Lys Val Gly Glu Lys Ile Gln Val Glu Ile Ala
                725                 730                 735
```

```
Asp Ile Asp Asn Arg Gly Lys Ile Ser Leu Val Pro Val Glu Glu
            740                 745                 750

Asp

<210> SEQ ID NO 40
<211> LENGTH: 548
<212> TYPE: PRT
<213> ORGANISM: Corynebacterium glutamicum
<220> FEATURE:
<221> NAME/KEY: MISC_FEATURE
<222> LOCATION: (1)..(548)
<223> OTHER INFORMATION: Translated Polypeptide for RNA
      degradation/processing gene groEL

<400> SEQUENCE: 40

Met Ala Lys Ile Ile Ala Phe Asp Glu Glu Ala Arg Arg Gly Leu Glu
1               5                   10                  15

Lys Gly Leu Asn Thr Leu Ala Asp Ala Val Lys Val Thr Leu Gly Pro
            20                  25                  30

Lys Gly Arg Asn Val Val Leu Glu Lys Ala Trp Gly Ala Pro Thr Ile
        35                  40                  45

Thr Asn Asp Gly Val Thr Ile Ala Arg Glu Ile Glu Leu Glu Asp Pro
    50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Lys Glu Gly Leu Arg Asn Val Ala Ala Gly Ser Asn Pro
            100                 105                 110

Met Gly Ile Lys Arg Gly Ile Glu Lys Ala Val Ala Gln Val Thr Glu
        115                 120                 125

Lys Leu Leu Glu Ala Ala Lys Glu Val Glu Thr Glu Glu Gln Ile Ala
    130                 135                 140

Ala Thr Ala Gly Ile Ser Ala Ala Asp Pro Ala Ile Gly Ala Gln Ile
145                 150                 155                 160

Ala Lys Ala Met Tyr Ala Val Gly Gly Gly Lys Leu Asn Lys Asp Ser
                165                 170                 175

Val Ile Thr Val Glu Glu Ser Asn Thr Phe Gly Val Glu Leu Glu Val
            180                 185                 190

Thr Glu Gly Met Arg Phe Asp Lys Gly Tyr Ile Ser Gly Tyr Phe Ala
        195                 200                 205

Thr Asp Met Glu Arg Leu Glu Ala Val Leu Glu Asp Pro Tyr Ile Leu
    210                 215                 220

Leu Val Ser Gly Lys Ile Ser Asn Ile Lys Asp Leu Leu Pro Leu Leu
225                 230                 235                 240

Glu Lys Val Met Gln Ser Gly Lys Pro Leu Leu Ile Ile Ser Glu Asp
                245                 250                 255

Val Glu Gly Glu Ala Leu Ser Thr Leu Val Val Asn Lys Ile Arg Gly
            260                 265                 270

Thr Phe Lys Ser Val Ala Val Lys Ala Pro Gly Phe Gly Asp Arg Arg
        275                 280                 285

Lys Ala Gln Leu Gln Asp Ile Ala Val Leu Thr Gly Gly Gln Val Ile
    290                 295                 300

Ser Glu Glu Val Gly Leu Ser Leu Glu Thr Ala Asp Leu Pro Leu Leu
305                 310                 315                 320
```

```
Gly Gln Ala Arg Lys Val Val Thr Lys Asp Asp Thr Thr Ile Val
            325                 330                 335

Asp Gly Ala Gly Ser Glu Ala Gln Ile Glu Gly Arg Val Asn Gln Ile
        340                 345                 350

Arg Val Glu Ile Glu Asn Ser Asp Ser Asp Tyr Asp Arg Glu Lys Leu
            355                 360                 365

Asn Glu Arg Leu Ala Lys Leu Ala Gly Gly Val Ala Val Leu Lys Val
370                 375                 380

Gly Ala Ala Thr Glu Val Glu Leu Lys Glu Arg Lys His Arg Ile Glu
385                 390                 395                 400

Asp Ala Val Arg Asn Ala Lys Ala Ala Val Glu Glu Gly Ile Val Ala
            405                 410                 415

Gly Gly Gly Val Ala Leu Leu Gln Ala Ala His Val Leu Asp Asn Asp
            420                 425                 430

Leu Glu Leu Ser Gly Asp Glu Ala Thr Gly Val Arg Ile Val Arg Glu
            435                 440                 445

Ala Leu Thr Ala Pro Leu Lys Gln Ile Ala Ala Asn Ala Gly Leu Glu
    450                 455                 460

Pro Gly Val Val Ala Asp Lys Val Ser Gln Leu Pro Gln Gly Glu Gly
465                 470                 475                 480

Leu Asn Ala Ala Asn Gly Glu Tyr Val Asp Leu Met Ala Ala Gly Ile
            485                 490                 495

Asn Asp Pro Val Lys Val Thr Arg Ser Ala Leu Gln Asn Ala Ala Ser
            500                 505                 510

Ile Ala Ala Leu Phe Leu Thr Thr Glu Ala Val Val Ala Asp Lys Pro
    515                 520                 525

Gln Pro Ala Gly Ala Ala Gly Met Pro Gly Ala Asp Glu Met Gly Gly
    530                 535                 540

Met Gly Gly Phe
545

<210> SEQ ID NO 41
<211> LENGTH: 548
<212> TYPE: PRT
<213> ORGANISM: Corynebacterium glutamicum
<220> FEATURE:
<221> NAME/KEY: MISC_FEATURE
<222> LOCATION: (1)..(109)
<223> OTHER INFORMATION: Translated Polypeptide for RNA
      degradation/processing gene groEL CP012194 homolog

<400> SEQUENCE: 41

Met Ala Lys Ile Ile Ala Phe Asp Glu Glu Ala Arg Arg Gly Leu Glu
1               5                   10                  15

Lys Gly Leu Asn Thr Leu Thr Asp Ala Val Lys Val Thr Leu Gly Pro
            20                  25                  30

Lys Gly Arg Asn Val Val Leu Glu Lys Ala Trp Gly Ala Pro Thr Ile
        35                  40                  45

Thr Asn Asp Gly Val Thr Ile Ala Arg Glu Ile Glu Leu Glu Asp Pro
    50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
            85                  90                  95

Ala Leu Val Lys Glu Gly Leu Arg Asn Val Ala Ala Gly Ser Asn Pro
            100                 105                 110
```

```
Met Gly Ile Lys Arg Gly Ile Glu Lys Ala Val Ala Gln Val Thr Glu
            115                 120                 125
Lys Leu Leu Glu Ala Ala Lys Glu Val Glu Thr Glu Glu Gln Ile Ala
        130                 135                 140
Ala Thr Ala Gly Ile Ser Ala Ala Asp Pro Ala Ile Gly Ala Gln Ile
145                 150                 155                 160
Ala Lys Ala Met Tyr Ala Val Gly Gly Lys Leu Asn Lys Asp Ser
                165                 170                 175
Val Ile Thr Val Glu Glu Ser Asn Thr Phe Gly Val Glu Leu Glu Val
            180                 185                 190
Thr Glu Gly Met Arg Phe Asp Lys Gly Tyr Ile Ser Gly Tyr Phe Ala
        195                 200                 205
Thr Asp Met Glu Arg Leu Glu Ala Val Leu Glu Asp Pro Tyr Ile Leu
        210                 215                 220
Leu Val Ser Gly Lys Ile Ser Asn Ile Lys Asp Leu Leu Pro Leu Leu
225                 230                 235                 240
Glu Lys Val Met Gln Ser Gly Lys Pro Leu Leu Ile Ile Ser Glu Asp
                245                 250                 255
Val Glu Gly Glu Ala Leu Ser Thr Leu Val Val Asn Lys Ile Arg Gly
            260                 265                 270
Thr Phe Lys Ser Val Ala Val Lys Ala Pro Gly Phe Gly Asp Arg Arg
        275                 280                 285
Lys Ala Gln Leu Gln Asn Ile Ala Val Leu Thr Gly Gly Gln Val Ile
        290                 295                 300
Ser Glu Glu Val Gly Leu Ser Leu Glu Thr Ala Asp Leu Pro Leu Leu
305                 310                 315                 320
Gly Gln Ala Arg Lys Val Val Thr Lys Asp Thr Thr Ile Val
                325                 330                 335
Asp Gly Ala Gly Ser Glu Ala Gln Ile Glu Gly Arg Val Asn Gln Ile
            340                 345                 350
Arg Val Glu Ile Glu Asn Ser Asp Ser Asp Tyr Asp Arg Glu Lys Leu
        355                 360                 365
Asn Glu Arg Leu Ala Lys Leu Ala Gly Gly Val Ala Val Leu Lys Val
        370                 375                 380
Gly Ala Ala Thr Glu Val Glu Leu Lys Glu Arg Lys His Arg Ile Glu
385                 390                 395                 400
Asp Ala Val Arg Asn Ala Lys Ala Val Glu Glu Gly Ile Val Ala
                405                 410                 415
Gly Gly Gly Val Ala Leu Leu Gln Ala Ala His Val Leu Asp Asn Asp
            420                 425                 430
Leu Glu Leu Ser Gly Asp Glu Ala Thr Gly Val Arg Ile Val Arg Glu
        435                 440                 445
Ala Leu Thr Ala Pro Leu Lys Gln Ile Ala Ala Asn Ala Gly Leu Glu
        450                 455                 460
Pro Gly Val Val Ala Asp Lys Val Ser Gln Leu Pro Gln Gly Glu Gly
465                 470                 475                 480
Leu Asn Ala Ala Asn Gly Glu Tyr Val Asp Leu Met Ala Ala Gly Ile
                485                 490                 495
Asn Asp Pro Val Lys Val Thr Arg Ser Ala Leu Gln Asn Ala Ala Ser
            500                 505                 510
Ile Ala Ala Leu Phe Leu Thr Thr Glu Ala Val Val Ala Asp Lys Pro
        515                 520                 525
```

Gln Pro Ala Gly Ala Ala Gly Met Pro Gly Ala Asp Glu Met Gly Gly
    530                 535                 540

Met Gly Gly Phe
545

<210> SEQ ID NO 42
<211> LENGTH: 538
<212> TYPE: PRT
<213> ORGANISM: Corynebacterium glutamicum
<220> FEATURE:
<221> NAME/KEY: MISC_FEATURE
<222> LOCATION: (1)..(538)
<223> OTHER INFORMATION: Translated Polypeptide for RNA
      degradation/processing gene groEL2

<400> SEQUENCE: 42

Met Ala Lys Leu Ile Ala Phe Asp Gln Asp Ala Arg Glu Gly Ile Leu
1               5                   10                  15

Arg Gly Val Asp Ala Leu Ala Asn Ala Val Lys Val Thr Leu Gly Pro
            20                  25                  30

Arg Gly Arg Asn Val Val Leu Asp Lys Ala Phe Gly Gly Pro Leu Val
        35                  40                  45

Thr Asn Asp Gly Val Thr Ile Ala Arg Asp Ile Asp Leu Glu Asp Pro
    50                  55                  60

Phe Glu Asn Leu Gly Ala Gln Leu Val Lys Ser Val Ala Val Lys Thr
65                  70                  75                  80

Asn Asp Ile Ala Gly Asp Gly Thr Thr Thr Ala Thr Leu Leu Ala Gln
                85                  90                  95

Ala Leu Ile Ala Glu Gly Leu Arg Asn Val Ala Ala Gly Ala Asn Pro
            100                 105                 110

Met Glu Leu Asn Lys Gly Ile Ala Ala Ala Glu Lys Thr Leu Glu
        115                 120                 125

Glu Leu Lys Ala Arg Ala Thr Glu Val Ser Asp Thr Lys Glu Ile Ala
    130                 135                 140

Asn Val Ala Thr Val Ser Ser Arg Asp Glu Val Val Gly Glu Ile Val
145                 150                 155                 160

Ala Ala Ala Met Glu Lys Val Gly Lys Asp Gly Val Val Thr Val Glu
                165                 170                 175

Glu Ser Gln Ser Ile Glu Thr Ala Leu Glu Val Thr Glu Gly Ile Ser
            180                 185                 190

Phe Asp Lys Gly Tyr Leu Ser Pro Tyr Phe Ile Asn Asp Asn Asp Thr
        195                 200                 205

Gln Gln Ala Val Leu Asp Asn Pro Ala Val Leu Leu Val Arg Asn Lys
    210                 215                 220

Ile Ser Ser Leu Pro Asp Phe Leu Pro Leu Leu Glu Lys Val Val Glu
225                 230                 235                 240

Ser Asn Arg Pro Leu Leu Ile Ile Ala Glu Asp Val Glu Gly Glu Pro
                245                 250                 255

Leu Gln Thr Leu Val Val Asn Ser Ile Arg Lys Thr Ile Lys Val Val
            260                 265                 270

Ala Val Lys Ser Pro Tyr Phe Gly Asp Arg Arg Lys Ala Phe Met Asp
        275                 280                 285

Asp Leu Ala Ile Val Thr Lys Ala Thr Val Val Asp Pro Glu Val Gly
    290                 295                 300

Ile Asn Leu Asn Glu Ala Gly Glu Glu Val Phe Gly Thr Ala Arg Arg
305                 310                 315                 320

```
Ile Thr Val Ser Lys Asp Glu Thr Ile Ile Val Asp Gly Ala Gly Ser
            325                 330                 335

Ala Glu Asp Val Glu Ala Arg Arg Gly Gln Ile Arg Arg Glu Ile Ala
        340                 345                 350

Asn Thr Asp Ser Thr Trp Asp Arg Glu Lys Ala Glu Glu Arg Leu Ala
        355                 360                 365

Lys Leu Ser Gly Gly Ile Ala Val Ile Arg Val Gly Ala Ala Thr Glu
    370                 375                 380

Thr Glu Val Asn Asp Arg Lys Leu Arg Val Glu Asp Ala Ile Asn Ala
385                 390                 395                 400

Ala Arg Ala Ala Gln Glu Gly Val Ile Ala Gly Gly Ser Ala
                405                 410                 415

Leu Val Gln Ile Ala Glu Thr Leu Lys Ala Tyr Ala Glu Glu Phe Glu
                420                 425                 430

Gly Asp Gln Lys Val Gly Val Arg Ala Leu Ala Thr Ala Leu Gly Lys
            435                 440                 445

Pro Ala Tyr Trp Ile Ala Ser Asn Ala Gly Leu Asp Gly Ser Val Val
        450                 455                 460

Val Ala Arg Thr Ala Ala Leu Pro Asn Gly Glu Gly Phe Asn Ala Ala
465                 470                 475                 480

Thr Leu Glu Tyr Gly Asn Leu Ile Asn Asp Gly Val Ile Asp Pro Val
                485                 490                 495

Lys Val Thr His Ser Ala Val Val Asn Ala Thr Ser Val Ala Arg Met
                500                 505                 510

Val Leu Thr Thr Glu Ala Ser Val Val Glu Lys Pro Ala Glu Glu Ala
            515                 520                 525

Ala Asp Ala His Ala Gly His His His His
    530                 535
```

<210> SEQ ID NO 43
<211> LENGTH: 269
<212> TYPE: PRT
<213> ORGANISM: Corynebacterium glutamicum
<220> FEATURE:
<221> NAME/KEY: MISC_FEATURE
<222> LOCATION: (1)..(269)
<223> OTHER INFORMATION: Translated Polypeptide for RNA
      degradation/processing gene mutM2

<400> SEQUENCE: 43

```
Met Pro Glu Gly His Val Ile His Arg Leu Ala Gly Glu Leu Thr Lys
1               5                   10                  15

Asn Phe Gly Asp Thr Ile Leu Asp Ala Thr Ser Pro Gln Gly Arg Phe
            20                  25                  30

Ala Ser Glu Ala Ala Ile Ile Asn Gly His Arg Ile Ala Val Ala Glu
        35                  40                  45

Ala Tyr Gly Lys His Leu Phe Val Glu Phe Asp Ala Asp His Pro Glu
    50                  55                  60

His Ile Leu Tyr Ile His Leu Gly Leu Ile Gly Thr Leu Gln Phe Glu
65                  70                  75                  80

Pro Ala Glu Glu Thr Arg Gly Gln Ile Arg Leu His Leu Ser Asp Gly
                85                  90                  95

Glu Ile Ala Ala Asn Leu Arg Gly Pro Gln Trp Cys Arg Leu Ile Thr
            100                 105                 110

Asp Ala Glu His Thr Gln Ala Ile Gly Lys Leu Gly Ala Asp Pro Ile
        115                 120                 125
```

```
Arg Asp Asp Ala Asp Pro Glu Pro Ile Arg Ile Lys Val Gln Arg Ser
    130                 135                 140

Gly Arg Ser Ile Gly Ser Leu Leu Met Asp Gln Lys Leu Phe Ala Gly
145                 150                 155                 160

Val Gly Asn Ile Tyr Arg Ala Glu Thr Leu Phe Arg Leu Gly Ile Ser
                165                 170                 175

Pro Phe Thr Ile Gly Lys Asp Ile Thr Thr Ala Gln Phe Arg Ser Ile
                180                 185                 190

Trp Ala Asp Leu Val Gly Leu Met Lys Asp Gly Val Val Ala Gly Arg
                195                 200                 205

Ile Asp Thr Val Arg Pro Glu His Thr Pro Glu Ala Met Gly Arg Pro
    210                 215                 220

Pro Arg Lys Asp Asp His Gly Gly Glu Val Tyr Thr Tyr Arg Arg Thr
225                 230                 235                 240

Gly Gln Glu Cys Phe Leu Cys Ala Thr Pro Ile Lys Glu Gln Val Met
                245                 250                 255

Glu Gly Arg Asn Leu Phe Trp Cys Pro Gly Cys Gln Arg
                260                 265
```

<210> SEQ ID NO 44
<211> LENGTH: 424
<212> TYPE: PRT
<213> ORGANISM: Corynebacterium glutamicum
<220> FEATURE:
<221> NAME/KEY: MISC_FEATURE
<222> LOCATION: (1)..(424)
<223> OTHER INFORMATION: Translated Polypeptide for RNA
      degradation/processing gene rhlE

<400> SEQUENCE: 44

```
Val Ser Ser Glu Ser Pro Arg Pro Thr Phe Thr Glu Leu Gly Val Ala
1               5                   10                  15

Val Glu Ile Thr Asp Ala Leu Glu Ala Leu Gly Ile Asn Arg Thr Phe
                20                  25                  30

Ala Ile Gln Glu Tyr Thr Leu Pro Ile Ala Leu Asp Gly His Asp Phe
            35                  40                  45

Ile Gly Gln Ala Arg Thr Gly Met Gly Lys Thr Tyr Gly Phe Gly Val
    50                  55                  60

Pro Leu Leu Asp Arg Val Phe Asp Ser Ala Asp Val Ala Ala Thr Asp
65                  70                  75                  80

Gly Thr Pro Arg Ala Leu Val Ile Val Pro Thr Arg Glu Leu Ala Val
                85                  90                  95

Gln Val Gly Asp Asp Leu Gln Arg Ala Ala Thr Asn Leu Pro Leu Lys
                100                 105                 110

Ile Phe Thr Phe Tyr Gly Gly Thr Pro Tyr Glu Glu Gln Ile Asp Ala
            115                 120                 125

Leu Lys Val Gly Val Asp Val Val Gly Thr Pro Gly Arg Leu Leu
    130                 135                 140

Asp Leu His Lys Arg Gly Ala Leu Ser Leu Asp Lys Val Ala Ile Leu
145                 150                 155                 160

Val Leu Asp Glu Ala Asp Glu Met Leu Asp Leu Gly Phe Leu Pro Asp
                165                 170                 175

Ile Glu Lys Ile Leu Arg Ala Leu Thr His Gln His Gln Thr Met Leu
            180                 185                 190

Phe Ser Ala Thr Met Pro Gly Ala Ile Leu Thr Leu Ala Arg Ser Phe
        195                 200                 205
```

```
Leu Asn Lys Pro Val His Ile Arg Ala Glu Thr Ser Asp Ala Ser Ala
210                 215                 220

Thr His Lys Thr Thr Arg Gln Val Val Phe Gln Ala His Lys Met Asp
225                 230                 235                 240

Lys Glu Ala Ile Thr Ala Lys Ile Leu Gln Ala Lys Asp Arg Gly Lys
            245                 250                 255

Thr Ile Ile Phe Ala Arg Thr Lys Arg Thr Ala Ala Gln Val Ala Glu
            260                 265                 270

Asp Leu Ala Ser Arg Gly Phe Ser Val Gly Ser Val His Gly Asp Met
            275                 280                 285

Gly Gln Pro Ala Arg Glu Lys Ser Leu Asn Ala Phe Arg Thr Gly Lys
            290                 295                 300

Ile Asp Ile Leu Val Ala Thr Asp Val Ala Ala Arg Gly Ile Asp Val
305                 310                 315                 320

Asp Asp Val Thr His Val Ile Asn Tyr Gln Thr Pro Asp Asp Pro Met
                325                 330                 335

Thr Tyr Val His Arg Ile Gly Arg Thr Gly Arg Ala Gly His Asn Gly
            340                 345                 350

Thr Ala Val Thr Leu Val Gly Tyr Asp Glu Thr Leu Lys Trp Thr Val
            355                 360                 365

Ile Asp Asn Glu Leu Glu Leu Gly Gln Pro Asn Pro Pro Gln Trp Phe
370                 375                 380

Ser Thr Ser Pro Glu Leu Leu Glu Ala Leu Asp Ile Pro Glu Gly Val
385                 390                 395                 400

Thr Glu Arg Val Gly Pro Pro Thr Lys Val Leu Gly Gly Thr Ala Pro
                405                 410                 415

Arg Pro Pro Arg Arg Thr Arg Lys
            420

<210> SEQ ID NO 45
<211> LENGTH: 810
<212> TYPE: PRT
<213> ORGANISM: Corynebacterium glutamicum
<220> FEATURE:
<221> NAME/KEY: MISC_FEATURE
<222> LOCATION: (1)..(810)
<223> OTHER INFORMATION: Translated Polypeptide for RNA
      degradation/processing gene rho

<400> SEQUENCE: 45

Val Thr Thr Thr Asp Asn Thr Ala Ala Asn Gln Gly Glu Leu Thr Ala
1               5                   10                  15

Leu Arg Leu Pro Asp Leu Arg Lys Ile Ala Ala Asp Leu Gly Leu Lys
            20                  25                  30

Gly Thr Ser Ala Leu Arg Lys Gly Asp Leu Ile Asn Ala Ile Ser Ala
            35                  40                  45

Ala Arg Glu Gly Lys Pro Thr Ala Ala Lys Lys Thr Ser Pro Arg
50                  55                  60

Lys Ala Pro Ser Arg Thr Arg Ala Thr Gln Pro Ser Ala Pro Val Glu
65                  70                  75                  80

Gln Ala Gln Glu Ala Pro Ala Gln Thr Ser Thr Ala Pro Ala Ser Ala
            85                  90                  95

Pro Ser Glu Glu Thr Pro Ala Ala Pro Ala Arg Arg Gly Arg Arg Arg
            100                 105                 110

Val Thr Thr Thr Ala Thr Thr Pro Glu Pro Ala Ala Pro Ala Gln Ser
            115                 120                 125
```

-continued

```
Gln Pro Ala Glu Ala Gln Pro Ala Gln Thr Gln Ala Gln Gln Glu
    130                 135                 140
Glu Leu Pro Val Ala Ala Lys Glu Ser Ala Pro Ala Thr Glu Asn Thr
145                 150                 155                 160
Gln Gly Gln Ser Gln Gly Gln Ala Gln Gly Asp Glu His Asp Asp Arg
                165                 170                 175
Phe Glu Ser Arg Ser Ala Ala Arg Arg Ala Arg Arg Asn Arg Gln Arg
                180                 185                 190
Gln Ile His Arg Asp Gly Asp Asp Asn Ala Asn Ala Asn Thr Glu Ser
                195                 200                 205
Glu Gln Asn Thr Pro Ala Gln Asn Ala Thr Ala Gln Ala Glu Ser Glu
    210                 215                 220
Gln Thr Ala Ala Pro Ala Gln Ala Glu Ala Ala Glu Gln Asn Gln Asn
225                 230                 235                 240
Asp Asn Ser Glu Ser Ser Glu Asn Arg Ser Asp Asn Tyr Arg Asn Asn
                245                 250                 255
Asn Arg Arg Ser Arg Asn Asn Arg Asn Asn Arg Asn Tyr Arg Asp Asn
                260                 265                 270
Asn Glu Ser Ser Asp Asn Ala Gly Gln Ser Ser Asn Asp Asp Ala Asp
                275                 280                 285
Asn Asn Gln Ala Arg Ser Glu Asp Asn Asn Asp Arg Arg Ser Arg
                290                 295                 300
Asn Asn Arg Asn Asn Asp Arg Asn Asp Arg Asn Asp Arg Asn Tyr Arg
305                 310                 315                 320
Asp Asn Asn Glu Ser Ser Asp Asn Ala Gly Gln Ser Ser Asn Asp Asp
                325                 330                 335
Ala Asp Asn Asn Gln Ala Arg Ser Glu Asp Asn Asn Asp Arg Arg
                340                 345                 350
Ser Arg Asn Asn Arg Asn Asn Asp Arg Asn Asp Arg Asn Asp Arg Asn
                355                 360                 365
Tyr Arg Asp Asn His Asn Asp Asp Asn Asp Arg Arg Asn Arg Arg
                370                 375                 380
Gly Arg Arg Asn Arg Arg Gly Arg Asn Asp Arg Asn Asp Arg Asp Asn
385                 390                 395                 400
Arg Asp Asn Arg Asp Asn Arg Asp Asn Ser Asn Asp Gly Asp Asn Asn
                405                 410                 415
Gln Gln Asp Glu Leu Gln Val Ala Gly Ile Leu Asp Ile Val Asp
                420                 425                 430
His Asn Val Ala Phe Val Arg Thr Thr Gly Tyr His Ala Ala Pro Ser
                435                 440                 445
Asp Val Phe Val Ser Asn Gln Leu Ile Arg Arg Met Gly Leu Arg Ser
    450                 455                 460
Gly Asp Ala Ile Glu Gly Gln Val Arg Met Asn Gln Gly Gly Gly Asn
465                 470                 475                 480
His Asn Asn His Gly Arg Asn Arg Gln Lys Tyr Asn Asn Leu Val Arg
                485                 490                 495
Val Glu Met Val Asn Gly Leu Pro Ala Glu Glu Thr Arg Asn Arg Pro
                500                 505                 510
Glu Phe Gly Lys Leu Thr Pro Leu Tyr Pro Asn Gln Arg Leu His Leu
                515                 520                 525
Glu Thr Glu Gln Lys Ile Leu Thr Thr Arg Val Ile Asp Leu Ile Met
                530                 535                 540
```

```
Pro Ile Gly Lys Gly Gln Arg Ala Leu Ile Val Ser Pro Pro Lys Ala
545                 550                 555                 560

Gly Lys Thr Thr Ile Leu Gln Asn Ile Ala Asn Ala Ile Ser Thr Asn
                565                 570                 575

Asn Pro Glu Cys Tyr Leu Met Val Val Leu Val Asp Glu Arg Pro Glu
            580                 585                 590

Glu Val Thr Asp Met Gln Arg Ser Val Asn Gly Glu Val Ile Ala Ser
        595                 600                 605

Thr Phe Asp Arg Pro Pro Ser Glu His Thr Ala Val Ala Glu Leu Ala
    610                 615                 620

Ile Glu Arg Ala Lys Arg Leu Val Glu Gln Gly Gln Asp Val Val Val
625                 630                 635                 640

Leu Leu Asp Ser Ile Thr Arg Leu Gly Arg Ala Tyr Asn Asn Ser Ser
                645                 650                 655

Pro Ala Ser Gly Arg Ile Leu Ser Gly Gly Val Asp Ser Asn Ala Leu
            660                 665                 670

Tyr Pro Pro Lys Arg Phe Leu Gly Ala Ala Arg Asn Ile Glu Asn Gly
        675                 680                 685

Gly Ser Leu Thr Ile Ile Ala Thr Ala Met Val Glu Thr Gly Ser Ala
    690                 695                 700

Gly Asp Thr Val Ile Phe Glu Glu Phe Lys Gly Thr Gly Asn Ala Glu
705                 710                 715                 720

Leu Lys Leu Asp Arg Lys Ile Ser Glu Arg Val Phe Pro Ala Val
                725                 730                 735

Asp Val Asn Pro Ser Gly Thr Arg Lys Asp Glu Leu Leu Leu Asn Pro
            740                 745                 750

Asp Glu Ala Arg Ile Met His Lys Leu Arg Arg Ile Leu Ser Ala Leu
        755                 760                 765

Asp Asn Gln Gln Ala Ile Asp Leu Leu Ile Lys Gln Leu Lys Lys Thr
    770                 775                 780

Lys Ser Asn Ala Glu Phe Leu Met Gln Val Ala Ser Ser Ala Pro Met
785                 790                 795                 800

Ala Gly Thr Glu Lys Glu Glu Asp Tyr Ser
                805                 810

<210> SEQ ID NO 46
<211> LENGTH: 1021
<212> TYPE: PRT
<213> ORGANISM: Corynebacterium glutamicum
<220> FEATURE:
<221> NAME/KEY: MISC_FEATURE
<222> LOCATION: (1)..(1021)
<223> OTHER INFORMATION: Translated Polypeptide for RNA
      degradation/processing gene rne

<400> SEQUENCE: 46

Val Pro Asn Asn Lys Ala Val Glu Ala Glu Ile Ser Pro Ser Ala Val
1               5                   10                  15

Leu Ala Ala Glu Phe Asp Arg Asp Ser Leu Ser Glu Lys Thr Arg Val
                20                  25                  30

His Gln Leu Ala Lys Arg Leu Gly Met Val Ser Lys Asp Val Val Val
            35                  40                  45

Ala Leu Asp Gly Ile Gly Leu Val Lys Val Ala Gln Ser Asn Leu Ser
        50                  55                  60

Lys Glu Glu Val Glu Lys Leu Leu Asp Ala Leu Ser Gln Pro Val Leu
65                  70                  75                  80
```

```
Asn Ala Ala Pro Ala Val Pro Asp Val Glu Pro Val Glu Lys Ile
             85                  90                  95
Arg Arg Arg Val Glu Lys Asn Val Glu Asn Glu Ile His Gln Ile Glu
            100                 105                 110
Glu Lys Val Glu Arg Glu Leu Ala Ala Val Ala Gln Pro Thr Asp Phe
        115                 120                 125
Glu Ala Ala Arg Glu Glu Val Thr Ala Glu Leu Leu Glu Asp Ile
    130                 135                 140
Val Pro Glu Ile Thr Pro Ala Pro Val Glu Ala Pro Val Tyr Thr Pro
145                 150                 155                 160
Ile Phe Val Ala Pro Ala Val Val Pro Thr Glu Asn Val Gln His Thr
                165                 170                 175
Asp Asp Glu Gln Ala Arg Glu Arg Thr Ala Arg Lys Arg Arg Gly Arg
            180                 185                 190
Arg Gly Thr Gly Arg Gly Arg Gly Ala Glu Ala Glu Thr Val Thr Glu
        195                 200                 205
Val Ser Glu Glu Ala Ser Thr Ser Glu Val Glu Val Asn Glu Pro
    210                 215                 220
Ile Gly Ile Lys Gly Ser Thr Arg Leu Glu Ala Gln Arg Arg Arg
225                 230                 235                 240
Thr Glu Met Arg Glu Glu Asn Lys Lys Arg Arg His Val Val Ser Thr
                245                 250                 255
Gln Glu Phe Met Glu Arg Arg Glu Ser Met Glu Arg Arg Met Ile Val
            260                 265                 270
Arg Glu Arg Gln Arg His Asp His Pro Gly Leu Val Thr Gln Val Gly
        275                 280                 285
Val Leu Glu Asp Asp Gln Leu Val Glu Gln Phe Val Thr Ser Asp Ala
    290                 295                 300
Gln Met Ser Met Val Gly Asn Ile Tyr Leu Gly Arg Val Gln Asn Val
305                 310                 315                 320
Leu Pro Ser Met Glu Ala Ala Phe Ile Asp Ile Gly Lys Gly Arg Asn
                325                 330                 335
Gly Val Leu Tyr Ala Gly Glu Val Asp Trp Lys Ala Ala Gly Leu Gly
            340                 345                 350
Gly Arg Gly Arg Arg Ile Glu Gln Ala Leu Lys Ala Gly Asp Gln Val
        355                 360                 365
Leu Val Gln Val Ser Lys Asp Pro Leu Gly His Lys Gly Ala Arg Leu
    370                 375                 380
Thr Thr Gln Ile Ser Leu Ala Gly Arg Tyr Leu Val Tyr Val Pro Gly
385                 390                 395                 400
Gly Arg Ser Ala Gly Ile Ser Arg Lys Leu Pro Gly Pro Glu Arg Lys
                405                 410                 415
Arg Leu Lys Glu Ile Leu Gly Arg Val Val Pro Ala Gln Gly Gly Thr
            420                 425                 430
Ile Ile Arg Thr Ala Ala Glu Gly Val Ser Glu Glu Asn Ile Ala Ala
        435                 440                 445
Asp Val Asn Arg Leu His Thr Leu Trp Glu Gln Ile Lys Glu Arg Thr
    450                 455                 460
Ala Lys Glu Lys Lys Ser Arg Gly Ser Lys Pro Ile Thr Met Tyr Glu
465                 470                 475                 480
Glu Pro Asp Met Leu Val Lys Val Ile Arg Asp Leu Phe Asn Glu Asp
                485                 490                 495
```

-continued

```
Phe Thr Ser Leu Ile Val Asp Gly Asp Arg Ala Trp Asn Thr Val Arg
            500                 505                 510
Ala Tyr Ile Gln Ser Val Ala Pro Asp Leu Val Ser Arg Val Glu His
        515                 520                 525
Phe Asp Arg Ala Asp Phe Asp Gly Lys Asp Ala Phe Glu Ala Phe Asp
    530                 535                 540
Leu Asn Thr Gln Leu Glu Glu Ala Leu Ser Arg Lys Val Asn Leu Pro
545                 550                 555                 560
Ser Gly Gly Ser Leu Ile Ile Asp Arg Thr Glu Ala Met Thr Val Ile
            565                 570                 575
Asp Val Asn Thr Gly Arg Tyr Thr Gly Lys Gly Gly Asn Leu Glu
        580                 585                 590
Glu Thr Val Thr Leu Asn Asn Ile Glu Ala Ala Glu Ile Val Arg
    595                 600                 605
Gln Met Arg Leu Arg Asp Leu Gly Gly Met Ile Val Val Asp Phe Ile
    610                 615                 620
Asp Met Val Leu Pro Glu Asn Gln Glu Leu Val Leu Arg Arg Leu Asn
625                 630                 635                 640
Glu Ala Leu Glu Asn Asp Arg Thr Arg His Gln Val Ser Glu Val Thr
            645                 650                 655
Ser Leu Gly Leu Val Gln Met Thr Arg Lys Arg Ile Gly Ala Gly Leu
            660                 665                 670
Leu Glu Thr Phe Ser Ser Pro Cys Glu His Cys Glu Gly Arg Gly Ile
            675                 680                 685
Ile Val His Val Asp Pro Val Asp Thr Val Asp Glu Arg Val Glu Ala
        690                 695                 700
Lys Ala Glu Glu Arg Ser Arg Arg His Gln Arg Ser Asn Ser Thr Glu
705                 710                 715                 720
Lys Ala Ala Ala Glu His Pro Met Val Val Ala Met Arg Asp Leu Val
            725                 730                 735
Glu Ser Asp Glu His Asp Leu Asp Gln Glu Phe Glu Glu Leu Ala Ala
            740                 745                 750
Ser Val Ile Val Leu Asp Asp Ser Asp Leu Asp Asp Val Val Asn Asp
        755                 760                 765
Lys Leu Asp Glu Pro Glu Arg Ile Leu Ala Glu Ser Thr Val Glu Pro
770                 775                 780
Glu Glu Gly Pro Arg Arg Arg Ala Arg Gln Arg Gln Glu Ser Ala
785                 790                 795                 800
Ala Asp Asp Ile Ala Ala Ile Ala Ala Ala Val Asp Ile Ala Ser
            805                 810                 815
Glu Glu Asp Pro Asp Glu Pro Ser Gly Ser Ser Tyr Val Ser Asp Leu
            820                 825                 830
Glu Ala Glu Pro Ile Ala Pro Val Val Glu Lys Ala Ala Glu Pro Val
        835                 840                 845
Ala Glu Pro Thr Ala Asp Tyr Glu Lys Ala Arg Ala Glu Phe Glu Ala
    850                 855                 860
Ser Pro Arg Arg Arg Lys Thr Arg Gly Asn Ser Arg Ser Asp His
865                 870                 875                 880
Ala Pro Lys Pro Glu Asp Phe Ala Pro Val Val Glu Glu Val Ala Glu
            885                 890                 895
Thr Pro Val Lys Thr Pro Ala Arg Lys Ala Pro Arg Arg Asn Arg Pro
            900                 905                 910
```

```
Ser Glu Leu Ser Ser Gly Ala Pro Ser Ser Ala Pro Leu Thr Arg Asn
            915                 920                 925

Arg Arg Arg Ala Val Arg Gln Leu Val Glu Ala Pro Glu Thr Val
930                 935                 940

Val Glu Ile Ala Pro Glu Ala Pro Glu Gln Val Ala Glu Pro Gln
945                 950                 955                 960

Val Glu Phe Asp Gln Pro Asp Asn Arg Lys Arg Arg Ala Val
                965                 970                 975

Arg Val Thr Ala Ala Pro Val Glu Lys Lys Val Ala Ser Thr Ser Asn
            980                 985                 990

Ala Arg Ala Pro Lys Lys Glu Pro Gln Ala Ala Ser Thr Thr Asn Pro
            995                 1000                1005

Gly Arg Arg Arg Arg Ala Thr Arg Arg Gly Pro Arg Ser
        1010                1015                1020

<210> SEQ ID NO 47
<211> LENGTH: 718
<212> TYPE: PRT
<213> ORGANISM: Corynebacterium glutamicum
<220> FEATURE:
<221> NAME/KEY: MISC_FEATURE
<222> LOCATION: (1)..(718)
<223> OTHER INFORMATION: Translated Polypeptide for RNA
      degradation/processing gene cg2160/ RNAse J

<400> SEQUENCE: 47

Met Asn Asp Ser Arg Asn Arg Gly Arg Lys Val Thr Arg Lys Ala Gly
1               5                   10                  15

Pro Pro Glu Ala Gly Gln Glu Asn His Leu Asp Thr Pro Val Phe Gln
            20                  25                  30

Ala Pro Asp Ala Ser Ser Asn Gln Ser Ala Val Lys Ala Glu Thr Ala
        35                  40                  45

Gly Asn Asp Asn Arg Asp Ala Ala Gln Gly Ala Gln Gly Ser Gln Asp
    50                  55                  60

Ser Gln Gly Ser Gln Asn Ala Gln Gly Ser Gln Asn Arg Glu Ser Gly
65                  70                  75                  80

Asn Asn Asn Arg Asn Arg Ser Asn Asn Asn Arg Arg Gly Gly Arg Gly
                85                  90                  95

Arg Arg Gly Ser Gly Asn Ala Asn Glu Gly Ala Asn Asn Asn Ser Gly
            100                 105                 110

Asn Gln Asn Arg Gln Gly Gly Asn Arg Gly Asn Arg Gly Gly Arg
        115                 120                 125

Arg Asn Val Val Lys Ser Met Gln Gly Ala Asp Leu Thr Gln Arg Leu
130                 135                 140

Pro Glu Pro Pro Lys Ala Pro Ala Asn Gly Leu Arg Ile Tyr Ala Leu
145                 150                 155                 160

Gly Gly Ile Ser Glu Ile Gly Arg Asn Met Thr Val Phe Glu Tyr Asn
                165                 170                 175

Asn Arg Leu Leu Ile Val Asp Cys Gly Val Leu Phe Pro Ser Ser Gly
            180                 185                 190

Glu Pro Gly Val Asp Leu Ile Leu Pro Asp Phe Gly Pro Ile Glu Asp
        195                 200                 205

His Leu His Arg Val Asp Ala Leu Val Val Thr His Gly His Glu Asp
    210                 215                 220

His Ile Gly Ala Ile Pro Trp Leu Leu Lys Leu Arg Asn Asp Ile Pro
225                 230                 235                 240
```

```
Ile Leu Ala Ser Arg Phe Thr Leu Ala Leu Ile Ala Ala Lys Cys Lys
                245                 250                 255

Glu His Arg Gln Arg Pro Lys Leu Ile Glu Val Asn Glu Gln Ser Asn
            260                 265                 270

Glu Asp Arg Gly Pro Phe Asn Ile Arg Phe Trp Ala Val Asn His Ser
        275                 280                 285

Ile Pro Asp Cys Leu Gly Leu Ala Ile Lys Thr Pro Ala Gly Leu Val
    290                 295                 300

Ile His Thr Gly Asp Ile Lys Leu Asp Gln Thr Pro Pro Asp Gly Arg
305                 310                 315                 320

Pro Thr Asp Leu Pro Ala Leu Ser Arg Phe Gly Asp Glu Gly Val Asp
                325                 330                 335

Leu Met Leu Cys Asp Ser Thr Asn Ala Thr Thr Pro Gly Val Ser Gly
            340                 345                 350

Ser Glu Ala Asp Val Ala Pro Thr Leu Lys Arg Leu Val Gly Asp Ala
        355                 360                 365

Lys Gln Arg Val Ile Leu Ala Ser Phe Ala Ser Asn Val Tyr Arg Val
    370                 375                 380

Gln Ala Ala Val Asp Ala Ala Val Ala Ser Asn Arg Lys Val Ala Phe
385                 390                 395                 400

Asn Gly Arg Ser Met Ile Arg Asn Met Glu Ile Ala Glu Lys Leu Gly
                405                 410                 415

Tyr Leu Lys Ala Pro Arg Gly Thr Ile Ile Ser Met Asp Asp Ala Ser
            420                 425                 430

Arg Met Ala Pro His Lys Val Met Leu Ile Thr Thr Gly Thr Gln Gly
        435                 440                 445

Glu Pro Met Ala Ala Leu Ser Arg Met Ala Arg Glu His Arg Gln
    450                 455                 460

Ile Thr Val Arg Asp Gly Asp Leu Ile Ile Leu Ser Ser Ser Leu Val
465                 470                 475                 480

Pro Gly Asn Glu Glu Ala Val Phe Gly Val Ile Asn Met Leu Ala Gln
                485                 490                 495

Ile Gly Ala Thr Val Val Thr Gly Arg Asp Ala Lys Val His Thr Ser
            500                 505                 510

Gly His Gly Tyr Ser Gly Glu Leu Leu Phe Leu Tyr Asn Ala Ala Arg
        515                 520                 525

Pro Lys Asn Ala Met Pro Val His Gly Glu Trp Arg His Leu Arg Ala
    530                 535                 540

Asn Lys Glu Leu Ala Ile Ser Thr Gly Val Asn Arg Asp Asn Val Val
545                 550                 555                 560

Leu Ala Gln Asn Gly Val Val Asp Met Val Asn Gly Arg Ala Gln
                565                 570                 575

Val Val Gly Gln Ile Pro Val Gly Asn Leu Tyr Val Asp Gly Val Thr
            580                 585                 590

Met Gly Asp Ile Asp Ala Asp Ile Leu Ala Asp Arg Thr Ser Leu Gly
        595                 600                 605

Glu Gly Gly Leu Ile Ser Ile Thr Ala Val Ile Asp Asn Arg Thr Gly
    610                 615                 620

Arg Leu Leu Glu Arg Pro Thr Val Gln Thr Ser Gly Phe Ser Glu Asp
625                 630                 635                 640

Ala Lys Ser Met Met Gly Glu Val Thr Glu Leu Ser Glu Thr Thr Met
                645                 650                 655
```

-continued

```
Asn Asp Leu Ala Ala Glu Gly Glu Asn Asp Pro Tyr Arg Met Val Gln
            660                 665                 670

Gln Leu Arg Arg Lys Leu Ser Arg Phe Val Glu Gln Lys Trp Lys Arg
        675                 680                 685

Gln Pro Val Ile Met Pro Thr Val Ile Pro Met Thr Ala Glu Thr Thr
    690                 695                 700

His Ile Gly Asp Asp Glu Val Arg Ala Ser Arg Glu Ser Leu
705                 710                 715
```